(12) United States Patent
Collins et al.

(10) Patent No.: US 7,282,513 B2
(45) Date of Patent: Oct. 16, 2007

(54) HETEROARYL SUBSTITUTED SPIROCYCLIC SULFAMIDES FOR INHIBITION OF GAMMA SECRETASE

(75) Inventors: Ian James Collins, Redhill (GB); Laura Catherine Cooper, Puckeridge (GB); Timothy Harrison, Great Dunmow (GB); Linda Elizabeth Keown, Great Dunmow (GB); Andrew Madin, Sawbridgeworth (GB); Mark Peter Ridgill, Watton-At-Stone (GB)

(73) Assignee: Merck Sharp & Dohme Limited, Hoddesdon, Hertfordshire (GB)

(*) Notice: Subject to any disclaimer, the term of this patent is extended or adjusted under 35 U.S.C. 154(b) by 0 days.

(21) Appl. No.: 11/366,866

(22) Filed: Mar. 2, 2006

(65) Prior Publication Data

US 2006/0173054 A1    Aug. 3, 2006

Related U.S. Application Data

(63) Continuation of application No. 10/512,810, filed as application No. PCT/GB03/01763 on Apr. 24, 2003, now Pat. No. 7,041,689.

(60) Provisional application No. 60/424,608, filed on Nov. 7, 2002.

(30) Foreign Application Priority Data

May 1, 2002    (GB) ................... 0209996.8
Oct. 14, 2002    (GB) ................... 0223873.1

(51) Int. Cl.
*A61K 31/433*    (2006.01)
*C07D 417/02*    (2006.01)

(52) U.S. Cl. ..................... 514/362; 548/126
(58) Field of Classification Search ............... 514/362; 548/126
See application file for complete search history.

(56) References Cited

U.S. PATENT DOCUMENTS

| 3,406,184 | A | 10/1968 | Raasch |
| 3,715,362 | A | 2/1973 | Dominianni |
| 5,703,129 | A | 12/1997 | Felsenstein et al. |
| 2004/0029862 | A1 | 2/2004 | Belanger et al. |
| 2004/0049038 | A1 | 3/2004 | Collins et al. |
| 2005/0182111 | A1 | 8/2005 | Pineiro et al. |
| 2005/0215602 | A1 | 9/2005 | Campbell et al. |

FOREIGN PATENT DOCUMENTS

| WO | WO98/38156 | 9/1998 |
| WO | WO 01/70677 | 9/2001 |
| WO | WO 02/36555 | 5/2002 |
| WO | WO 03/093251 | 11/2003 |
| WO | WO 03/093253 | 11/2003 |

OTHER PUBLICATIONS

J. E. Franz, et al.: Journal of Organic Chemistry, vol. 29, No. 10, Oct. 1964, pp. 2922-2927.
R. Huisgen, et al.: Chemische Berichte, vol. 98, No. 12, Dec. 1965, pp. 3992-4013.
S. Itsuno, et al.: Journal of the Chemical Society, Perkin Transactions 1, No. 10, Jul. 15, 1999, pp. 2011-2016.
M. Narisada, et al.: Journal of Medicinal Chemistry, vol. 31, No. 9, Sep. 1988, pp. 1847-1854.
K. B. Sharpless, et al.: Journal of Organic Chemistry, vol. 41, No. 1, Jan. 9, 1976, pp. 176-177.
Y. Yamaguchi, et al.: Xenobiotica, vol. 26, No. 6, Jun. 1996, pp. 613-626.
L. H. Zalkow, et al.: Journal of the American Chemical Society, vo. 86, No. 19, pp. 4208-4209, Oct. 5, 1964.
L. H. Zalkow, et al.: Journal of Organic Chemistry, vol. 28, No. 12, Dec. 1963, pp. 3303-3309.
J. L. Castro et al., "Synthesis and Biological Activity of . . . ," J. Med. Chem., vol. 37(19), pp. 3023-3032, (1994).
P. Aeberli et al., "Neuropharmacological Investigation of N-Benzylsulfamides," J. Med. Chem., vol. 10(4), pp. 636-642, (1967).
A. C. Oehlshlager et al., "Bridged Ring Compounds . . . ," J. Med. Chem., vol. 31, pp. 1682-1688, (1965).
G. M. Rishton et al., "Fenchylamine Sulfonamide Inhibitors of Amyloid Beta Peptide Production by the Gamma-Secretase Proteolytic Pathway . . . ", J. Med. Chem, vol. 43, pp. 2297-2299 (2000).

*Primary Examiner*—Kamal A. Saeed
(74) *Attorney, Agent, or Firm*—William Krovatin; John C. Todaro

(57) ABSTRACT

Compounds of formula I are disclosed:

in which X is a 5-membered heteroaryl ring and R is as defined herein. The compounds are inhibitors of the processing of APP by gamma-secretase, and hence are useful in the treatment or prevention of Alzheimer's disease.

10 Claims, No Drawings

HETEROARYL SUBSTITUTED SPIROCYCLIC SULFAMIDES FOR INHIBITION OF GAMMA SECRETASE

CROSS REFERENCE TO RELATED APPLICATIONS

This application is a continuation of U.S. patent application Ser. No. 10/512,810 filed Oct. 25, 2004 now U.S. Pat. No. 7,041,689, which is a U.S. National Phase application under 35 U.S.C. § 371 of PCT Application No. PCT/GB2003/001763, filed Apr. 24, 2003, which claims priority under 35 U.S.C. § 119(e) from U.S. Provisional Application Ser. No. 60/424,608, filed Nov. 7, 2002 and claims priority under 35 U.S.C. § 119(a) from Great Britain Application No. 0209996.8, filed May 1, 2002 and Great Britain Application No. 0223873.1, filed Oct. 14, 2002.

BACKGROUND OF THE INVENTION

The present invention relates to a novel class of compounds, their salts, pharmaceutical compositions comprising them, processes for making them and their use in therapy of the human body. In particular, the invention relates to compounds which modulate the processing of APP by γ-secretase, and hence are useful in the treatment or prevention of Alzheimer's disease.

Alzheimer's disease (AD) is the most prevalent form of dementia. Although primarily a disease of the elderly, affecting up to 10% of the population over the age of 65, AD also affects significant numbers of younger patients with a genetic predisposition. It is a neurodegenerative disorder, clinically characterized by progressive loss of memory and cognitive function, and pathologically characterized by the deposition of extracellular proteinaceous plaques in the cortical and associative brain regions of sufferers. These plaques mainly comprise fibrillar aggregates of β-amyloid peptide (Aβ), and although the exact role of the plaques in the onset and progress of AD is not fully understood, it is generally accepted that suppressing or attenuating the secretion of Aβ is a likely means of alleviating or preventing the condition. (See, for example, ID research alert 1996 1(2): 1-7; ID research alert 1997 2(1):1-8; Current Opinion in CPNS Investigational Drugs 1999 1(3):327-332; and Chemistry in Britain, Jan. 2000, 28-31.)

Aβ is a peptide comprising 39-43 amino acid residues, formed by proteolysis of the much larger amyloid precursor protein. The amyloid precursor protein (APP or AβPP) has a receptor-like structure with a large ectodomain, a membrane spanning region and a short cytoplasmic tail. Different isoforms of APP result from the alternative splicing of three exons in a single gene and have 695, 751 and 770 amino acids respectively.

The Aβ domain encompasses parts of both extra-cellular and transmembrane domains of APP, thus its release implies the existence of two distinct proteolytic events to generate its $NH_2$- and COOH-termini. At least two secretory mechanisms exist which release APP from the membrane and generate the soluble, COOH-truncated forms of APP ($APP_s$). Proteases which release APP and its fragments from the membrane are termed "secretases". Most $APP_s$ is released by a putative α-secretase which cleaves within the Aβ domain (between residues $Lys^{16}$ and $Leu^{17}$) to release α-$APP_s$ and precludes the release of intact Aβ. A minor portion of $APP_s$ is released by a β-secretase, which cleaves near the $NH_2$-terminus of Aβ and produces COOH-terminal fragments (CTFs) which contain the whole Aβ domain. Finding these fragments in the extracellular compartment suggests that another proteolytic activity (γ-secretase) exists under normal conditions which can generate the COOH-terminus of Aβ.

It is believed that γ-secretase itself depends for its activity on the presence of presenilin-1. In a manner that is not fully understood presenilin-1 appears to undergo autocleavage.

There are relatively few reports in the literature of compounds with inhibitory activity towards β- or γ-secretase, as measured in cell-based assays. These are reviewed in the articles referenced above. Many of the relevant compounds are peptides or peptide derivatives.

WO 01/70677 discloses certain sulphonamido-substituted bridged bicycloalkyl derivatives which are useful in the treatment of Alzheimer's disease, but neither discloses nor suggests the compounds of the present invention.

The present invention provides a novel class of non-peptidic compounds which are useful in the treatment or prevention of AD by modulating the processing of APP by the putative γ-secretase, thus arresting the production of Aβ and preventing the formation of insoluble plaques.

According to the invention there is provided a compound of formula I:

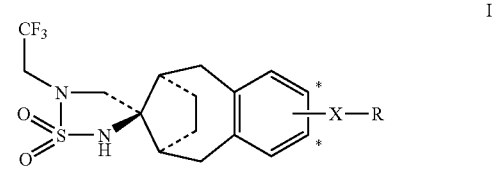

wherein the moiety X—R is attached at one of the positions indicated by an asterisk;

X is a bivalent pyrazole, imidazole, triazole, oxazole, isoxazole, thiazole, isothiazole, thiadiazole or 1,3,4-oxadiazole residue optionally bearing a hydrocarbon substituent comprising 1-5 carbon atoms which is optionally substituted with up to 3 halogen atoms; and R is selected from:

(i) $CF_3$ or a non-aromatic hydrocarbon group of up to 10 carbon atoms, optionally substituted with halogen, $CF_3$, $CHF_2$, CN, OH, $CO_2H$, $C_{2-6}$acyl, $C_{1-4}$alkoxy or $C_{1-4}$alkoxycarbonyl;

(ii) a non-aromatic heterocyclic group comprising up to 7 ring atoms of which up to 3 are chosen from N, O and S and the remainder are carbon, bearing 0-3 substituents independently selected from oxo, halogen, CN, $C_{1-6}$alkyl, OH, $CF_3$, $CHF_2$, $CH_2F$, $C_{2-6}$acyl, $CO_2H$, $C_{1-4}$alkoxy and $C_{1-4}$alkoxycarbonyl;

(iii) phenyl or 6-membered heteroaryl, either of which bears 0-3 substituents independently selected from halogen, $CF_3$, $CHF_2$, $CH_2F$, $NO_2$, CN, $OCF_3$, $C_{1-6}$alkyl and $C_{1-6}$alkoxy; and (iv) $N(R^a)_2$ where each $R^a$ independently represents H or $C_{1-6}$alkyl which is optionally substituted with halogen, $CF_3$, $CHF_2$, CN, OH, $CO_2H$, $C_{2-6}$acyl, $C_{1-4}$alkoxy or $C_{1-4}$alkoxycarbonyl;

or a pharmaceutically acceptable salt thereof.

In a subset of the compounds of formula I, X is a bivalent pyrazole, imidazole, triazole, oxazole, isoxazole, thiazole, isothiazole, thiadiazole or 1,3,4-oxadiazole residue wherein, in the case of pyrazole, imidazole and triazole, one of the ring nitrogen atoms optionally bears a hydrocarbon substituent comprising 1-5 carbon atoms which is optionally substituted with up to 3 halogen atoms; and R is selected from:

(i) a non-aromatic hydrocarbon group of up to 10 carbon atoms, optionally substituted with halogen, $CF_3$, $CHF_2$, CN, OH, $CO_2H$, $C_{2-6}$acyl, $C_{1-4}$alkoxy or $C_{1-4}$alkoxycarbonyl;

(ii) a non-aromatic heterocyclic group comprising up to 7 ring atoms of which up to 3 are chosen from N, O and S and the remainder are carbon, bearing 0-3 substituents independently selected from oxo, halogen, CN, $C_{1-6}$alkyl, OH, $CF_3$, $CHF_2$, $CH_2F$, $C_{2-6}$acyl, $CO_2H$, $C_{1-4}$alkoxy and $C_{1-4}$alkoxycarbonyl;

(iii) phenyl or 6-membered heteroaryl, either of which bears 0-3 substituents independently selected from halogen, $CF_3$, $CHF_2$, $CH_2F$, $NO_2$, CN, $OCF_3$, $C_{1-6}$alkyl and $C_{1-6}$alkoxy; and (iv) $N(R^a)_2$ where each $R^a$ independently represents H or $C_{1-6}$alkyl which is optionally substituted with halogen, $CF_3$, $CHF_2$, CN, OH, $CO_2H$, $C_{2-6}$acyl, $C_{1-4}$alkoxy or $C_{1-4}$alkoxycarbonyl.

It will be readily apparent to those skilled in the art that the compounds of formula I exist in two enantiomeric forms, depending on which of the ring positions indicated by an asterisk is bonded to the moiety —X—R. Attachment at the position indicated by the upper asterisk in formula I gives rise to a 2-substituted-[6S,9R,11R] 2',3',4',5,5',6,7,8,9,10-decahydro-5'-(2,2,2-trifluoroethyl)-spiro[6,9-methanobenzocyclooctene-11,3'-[1,2,5]thiadiazole] 1',1'-dioxide. Conversely, attachment at the position indicated by the lower asterisk in formula I gives rise to a 2-substituted-[6R,9S,11S]2',3',4',5,5',6,7,8,9,10-decahydro-5'-(2,2,2-trifluoroethyl)-spiro[6,9-methanobenzocyclooctene-11,3'-[1,2,5]thiadiazole] 1',1'-dioxide. It is to be emphasised that the invention, for each identity of —X—R, encompasses both enantiomers, either as homochiral compounds or as mixtures of enantiomers in any proportion. Furthermore, structural formulae depicting attachment of —X—R or a synthetic precursor thereof at one of the said ring positions shall hereinafter be indicative of attachment at either of said ring positions, unless expressly stated otherwise.

Where a variable occurs more than once in formula I or in a substituent thereof, the individual occurrences of that variable are independent of each other, unless otherwise specified.

As used herein, the expression "$C_{1-x}$alkyl" where x is an integer greater than 1 refers to straight-chained and branched alkyl groups wherein the number of constituent carbon atoms is in the range 1 to x. Particular alkyl groups are methyl, ethyl, n-propyl, isopropyl and t-butyl. Derived expressions such as "$C_{2-6}$alkenyl", "hydroxy$C_{1-6}$alkyl", "heteroaryl$C_{1-6}$alkyl", "$C_{2-6}$alkynyl" and "$C_{1-6}$alkoxy" are to be construed in an analogous manner. Most suitably, the number of carbon atoms in such groups is not more than 4.

The expression "$C_{3-6}$cycloalkyl" as used herein refers to nonaromatic monocyclic hydrocarbon ring systems comprising from 3 to 6 ring atoms. Examples include cyclopropyl, cyclobutyl, cyclopentyl, cyclohexyl and cyclohexenyl.

The expression "$C_{3-6}$ cycloalkyl($C_{1-6}$)alkyl" as used herein includes cyclopropylmethyl, cyclobutylmethyl, cyclopentylmethyl and cyclohexylmethyl.

The expression "$C_{2-6}$acyl" as used herein refers to ($C_{1-5}$alkyl)carbonyl groups, such as acetyl, propanoyl and butanoyl, including cycloalkyl derivatives such as cyclopentanecarbonyl and cyclobutanecarbonyl, and fluorinated derivatives such as trifluoroacetyl.

The term "halogen" as used herein includes fluorine, chlorine, bromine and iodine, of which fluorine and chlorine are preferred.

For use in medicine, the compounds of formula I may be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, benzenesulphonic acid, fumaric acid, maleic acid, succinic acid, acetic acid, benzoic acid, oxalic acid, citric acid, tartaric acid, carbonic acid or phosphoric acid. Alternatively, where the compound of the invention carries an acidic moiety, a pharmaceutically acceptable salt may be formed by neutralisation of said acidic moiety with a suitable base. Examples of pharmaceutically acceptable salts thus formed include alkali metal salts such as sodium or potassium salts; ammonium salts; alkaline earth metal salts such as calcium or magnesium salts; and salts formed with suitable organic bases, such as amine salts (including pyridinium salts) and quaternary ammonium salts.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

In the compounds of formula I, X is a bivalent pyrazole, imidazole, triazole, oxazole, isoxazole, thiazole, isothiazole, thiadiazole or 1,3,4-oxadiazole residue, optionally bearing a hydrocarbon substituent as defined previously. X may be bonded to R and to the fused benzene ring via any of the available ring positions of X. Typically, X is bonded both to R and to the fused benzene ring via carbon atoms, but when X is a pyrazole, imidazole or triazole residue, one of the points of attachment may be a nitrogen atom. Preferably, the points of attachment do not occupy adjacent ring atoms of X.

The ring represented by X optionally bears a hydrocarbon substituent comprising 1 to 5 carbon atoms, optionally substituted with up to 3 halogen atoms. Said optional hydrocarbon substituent may be attached to one of the ring carbon atoms of X, or when X is a pyrazole, imidazole or triazole residue and both of its points of attachment are carbon atoms, it may be attached to one of the ring nitrogen atoms of X. In either case, the optional hydrocarbon substituent may comprise cyclic or acyclic hydrocarbon residues or combinations thereof, saturated or unsaturated, up to a maximum of 5 carbon atoms in total. The optional hydrocarbon substituent is preferably unsubstituted or is substituted with up to 3 fluorine atoms Examples include methyl, ethyl, n-propyl, isopropyl, n-butyl, sec-butyl, t-butyl, fluoromethyl, difluoromethyl, trifluoromethyl, 2,2,2-trifluoroethyl, cyclopropyl, cyclopropylmethyl and allyl. A preferred example is methyl.

When X is a triazole or thiadiazole residue, both of the possible isomeric forms are within the scope of the invention. Thus, the definition of X encompasses both 1,2,3- and 1,2,4-triazole residues, and both 1,2,4- and 1,3,4-thiadiazole residues.

Suitable identities for X include 1,3,4-oxadiazol-2-yl, 1,3,4-thiadiazol-2-yl, 1,3,4-triazol-2-yl, 1,2,3-triazol-4-yl, 1,2,3-triazol-1-yl, 1,2,4-triazol-3-yl, 1-methyl-1,2,4-triazol- 3-yl, oxazol-2-yl, pyrazol-3-yl, 1-methylpyrazol-3-yl, 1-methylpyrazol-5-yl, 1-ethylpyrazol-3-yl, 1-(2,2,2-trifluoroethyl)pyrazol-3-yl, thiazol-2-yl, 4-methylthiazol-2-yl, isoxazol-5-yl, isoxazol-3-yl, imidazol-2-yl, imidazol-4-yl and imidazol-1-yl, wherein the numbering indicates the ring atom of X which is attached to the fused benzene ring in formula I.

Preferred identities for X include 1-methyl-1,2,4-triazol-3-yl, 1-methylpyrazol-3-yl, 1-ethylpyrazol-3-yl, oxazol-2-yl, thiazol-2-yl and 4-methylthiazol-2-yl, in which R is attached to the 5-position of X. A further preferred identity for X is imidazol-4-yl in which R is attached to the 1-position of X. Another preferred identity for X is 1,2,4-triazol-3-yl in which R is attached to the 1-position of X.

A particularly preferred identity for X is 1-methylpyrazol-3-yl in which R is attached to the 5-position.

In one embodiment, R is $CF_3$ or a non-aromatic hydrocarbon group of up to 10 carbon atoms, optionally substituted with halogen, $CF_3$, $CHF_2$, CN, OH, $CO_2H$, $C_{2-6}$acyl, $C_{1-4}$alkoxy or $C_{1-4}$alkoxycarbonyl. Within this definition, R may comprise cyclic or acyclic hydrocarbon residues or combinations thereof, saturated or unsaturated, up to a maximum of 10 carbon atoms in total, and may bear a substituent as detailed above. Within this embodiment, R typically contains up to 6 carbon atoms. Suitable examples include alkyl groups such as methyl, ethyl, n-propyl, isopropyl, n-butyl, sec-butyl, t-butyl and 2-methylpropyl, cycloalkyl groups such as cyclopropyl, cyclobutyl, cyclopentyl and cyclohexyl, cycloalkylalkyl groups such as cyclopropylmethyl and cyclopentylmethyl, alkenyl groups such as allyl, cyclopentenyl and cyclohexenyl, and alkynyl groups such as propargyl. Within this embodiment, R very aptly represents $CF_3$ or t-butyl or isopropyl.

In a second embodiment, R represents a non-aromatic heterocyclic group comprising up to 7 ring atoms of which up to 3 are chosen from N, O and S and the remainder are carbon, bearing 0-3 substituents independently selected from oxo, halogen, CN, $C_{1-6}$alkyl, OH, $CF_3$, $CHF_2$, $CH_2F$, $C_{2-6}$acyl, $CO_2H$, $C_{1-4}$alkoxy and $C_{1-4}$alkoxycarbonyl. Suitable heterocyclic groups include azetidine, pyrrolidine, piperidine, tetrahydropyridine, piperazine, morpholine, thiomorpholine, thiomorpholine-1,1-dioxide, pyran and thiopyran. Heterocyclic groups containing one or more nitrogen atoms may be bonded to X via carbon or via nitrogen. Within this embodiment, R very aptly represents piperidin-1-yl, 4-trifluoromethylpiperidin-1-yl, 4,4-difluoropiperidin-1-yl, 3,3-difluoropiperidin-1-yl, 3,3-difluoroazetidin-1-yl, morpholin-4-yl, 1-acetylpiperidin-4-yl, 1-trifluoroacetylpiperidin-4-yl, 1,2,3,6-tetrahydropyridin-4-yl, 1-trifluoroacetyl-1,2,3,6-tetrahydropyridin-4-yl or 1-(t-butoxycarbonyl)-1,2,3,6-tetrahydropyridin-4-yl. In a particular embodiment, when R represents an N-heterocyclyl group, X is an oxazole or thiazole residue, preferably thiazol-2-yl in which R is attached to the 5-position.

In a third embodiment, R represents phenyl or 6-membered heteroaryl, either of which bears 0-3 substituents independently selected from halogen, $CF_3$, $CHF_2$, $CH_2F$, $NO_2$, CN, $OCF_3$, $C_{1-6}$alkyl and $C_{1-6}$alkoxy. Examples of suitable 6-membered heteroaryl groups represented by R include pyridyl, pyrazinyl, pyrimidinyl, pyridazinyl and triazinyl. Preferably, the phenyl or heteroaryl ring bears 0 to 2 substituents. Phenyl groups represented by R preferably bear at least one substituent. Preferred substituents include halogen (especially chlorine and fluorine), CN, $C_{1-6}$alkyl (especially methyl), $C_{1-6}$alkoxy (especially methoxy), $OCF_3$ and $CF_3$. If two or more substituents are present, preferably not more than one of them is other than halogen or alkyl.

Within this embodiment, examples of groups represented by R include phenyl, monohalophenyl, dihalophenyl, trihalophenyl, cyanophenyl, methylphenyl, methoxyphenyl, trifluoromethylphenyl, trifluoromethoxyphenyl, pyridyl, monohalopyridyl and trifluoromethylpyridyl, wherein "halo" refers to fluoro or chloro. Suitable specific values for R include 2-fluorophenyl, 2-chlorophenyl, 3-fluorophenyl, 4-fluorophenyl, 4-chlorophenyl, 2,4-difluorophenyl, 2,4-dichlorophenyl, 3,4-difluorophenyl, 3,4-dichlorophenyl, 3-chloro-4-fluorophenyl, 3,4,5-trifluorophenyl, 4-cyanophenyl, 4-methylphenyl, 4-methoxyphenyl, 2-(trifluoromethyl)phenyl, 4-(trifluoromethyl)phenyl, 4-(trifluoromethoxy)phenyl, pyridin-2-yl, pyridin-3-yl, pyridin-4-yl, pyrazin-2-yl, 5-methylpyridin-2-yl, 5-fluoropyridin-2-yl, 5-chloropyridin-2-yl, 5-(trifluoromethyl)pyridin-2-yl and 6-(trifluoromethyl)pyridin-3-yl. Preferred examples include 2-fluorophenyl, 2-chlorophenyl, 3-fluorophenyl, 4-fluorophenyl, 4-chlorophenyl, 2,4-difluorophenyl, 2,4-dichlorophenyl, 3,4-difluorophenyl, 3,4-dichlorophenyl, 3-chloro-4-fluorophenyl, 4-(trifluoromethyl)phenyl, pyridin-2-yl, pyridin-3-yl and pyridin-4-yl.

In a fourth embodiment, R represents $N(R^a)_2$ where each $R^a$ independently represents H or $C_{1-6}$alkyl which is optionally substituted as defined previously. $R^a$ aptly represents H, unsubstituted alkyl such as methyl, ethyl, propyl or butyl, or haloalkyl such as mono-, di- or trifluoroethyl. Within this embodiment, R very aptly represents dimethylamino. In a particular embodiment, when R represents $N(R^a)_2$, X is an oxazole or thiazole residue, preferably thiazol-2-yl wherein R is attached to the 5-position.

In one preferred embodiment of the invention, X represents a bivalent pyrazole residue and R represents phenyl or 6-membered heteroaryl which is optionally substituted as defined above.

Representative compounds in accordance with the invention include those in which the moiety —X—R is selected from:

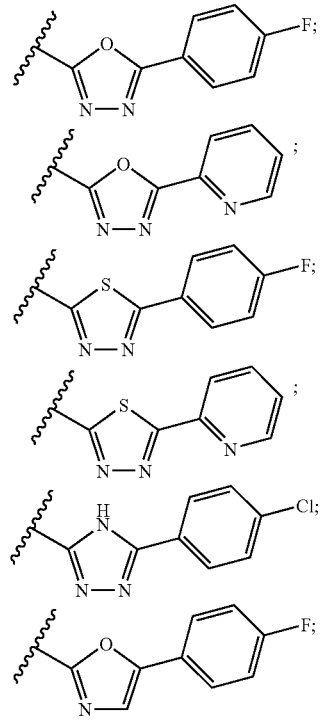

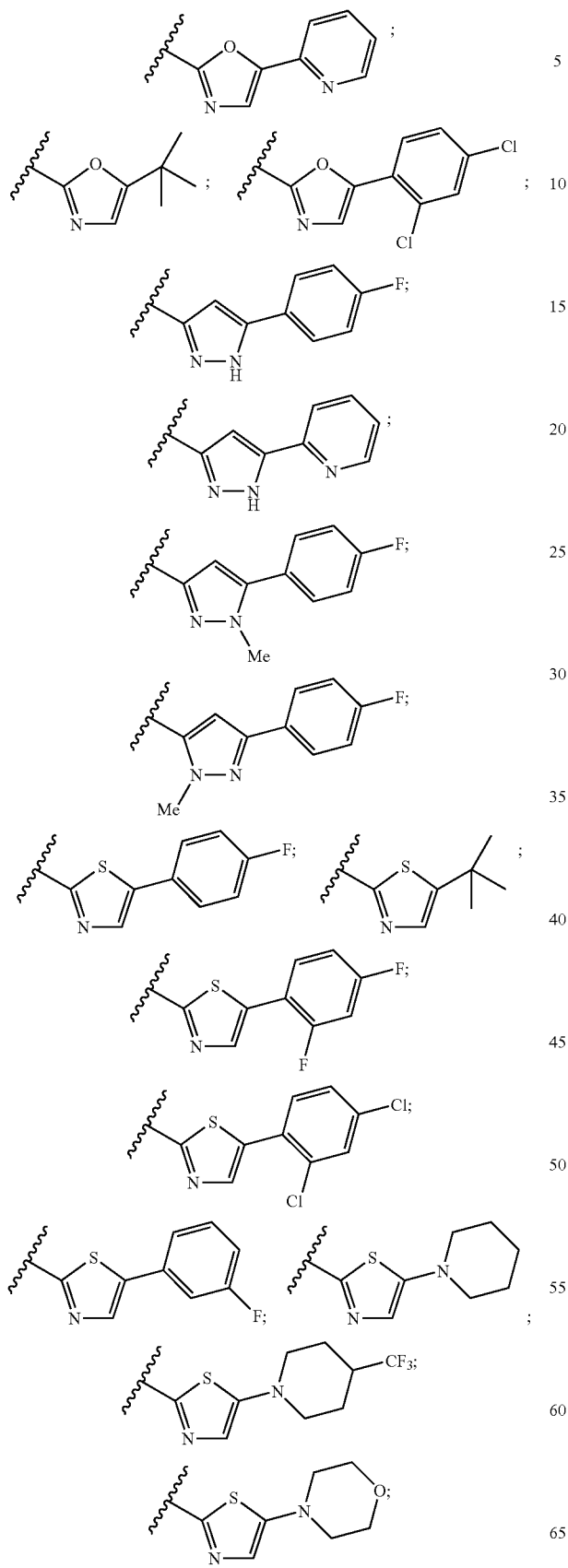
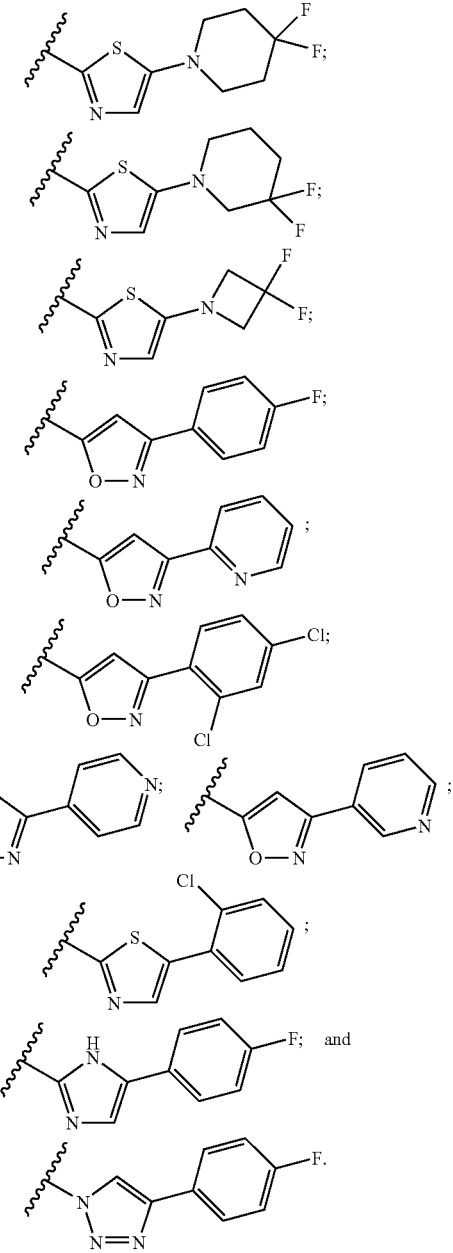
Further specific combinations of X and R are disclosed in the compounds described in the Examples section appended hereto.
A preferred subclass of the compounds of the invention are the 2-substituted-[6S,9R,11R] 2',3',4',5,5',6,7,8,9,10-decahydro-5'-(2,2,2-trifluoroethyl)-spiro[6,9-methanobenzocyclooctene-11,3'-[1,2,5]thiadiazole] 1',1'-dioxides of formula I(a):
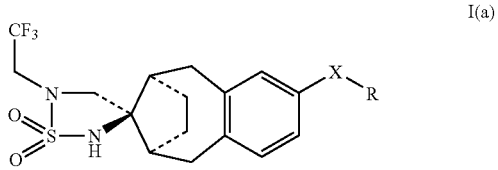
I(a)

wherein R and X have the same meanings and preferred identities as before;

and pharmaceutically acceptable salts thereof.

Within this subclass, X is very aptly 5-substituted-thiazol-2-yl, 5-substituted-4-methylthiazol-2-yl, 5-substituted-1-methylpyrazol-3-yl, 1-substituted-imidazol-4-yl or 1-substituted-1,2,4-triazol-3-yl.

Preferably, R represents optionally-substituted phenyl or heteroaryl as described previously.

Particularly preferred identities of R—X— include 5-(4-fluorophenyl)-1-methylpyrazol-3-yl and 1-(4-fluorophenyl) imidazol-4-yl.

The compounds of the present invention have an activity as inhibitors of γ secretase.

The invention also provides pharmaceutical compositions comprising one or more compounds of this invention and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. The principal active ingredient is mixed with a pharmaceutical carrier, e.g. conventional tableting ingredients such as corn starch, lactose, sucrose, sorbitol, talc, stearic acid, magnesium stearate and dicalcium phosphate, or gums or surfactants such as sorbitan monooleate, poly (ethylene glycol), and other pharmaceutical diluents, e.g. water, to form a homogeneous preformulation composition containing a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. Tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, liquid- or gel-filled capsules, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous solutions, gels or suspensions include synthetic and natural gums such as tragacanth, acacia, alginate, dextran, sodium carboxymethylcellulose, methylcellulose, poly(ethylene glycol), poly(vinylpyrrolidone) or gelatin.

The present invention also provides a compound of the invention or a pharmaceutically acceptable salt thereof for use in a method of treatment of the human body. Preferably the treatment is for a condition associated with the deposition of β-amyloid. Preferably the condition is a neurological disease having associated β-amyloid deposition such as Alzheimer's disease.

The present invention further provides the use of a compound of the present invention or a pharmaceutically acceptable salt thereof in the manufacture of a medicament for treating or preventing Alzheimer's disease.

Also disclosed is a method of treatment of a subject suffering from or prone to Alzheimer's disease which comprises administering to that subject an effective amount of a compound according to the present invention or a pharmaceutically acceptable salt thereof.

For treating or preventing Alzheimer's Disease, a suitable dosage level is about 0.01 to 250 mg/kg per day, preferably about 0.01 to 100 mg/kg per day, more preferably about 0.05 to 50 mg/kg of body weight per day, and for the most preferred compounds, about 0.1 to 10 mg/kg of body weight per day. The compounds may be administered on a regimen of 1 to 4 times per day. In some cases, however, a dosage outside these limits may be used.

The compounds of the invention are particularly suitable for oral administration.

Suitable starting materials for the preparation of the compounds of formula I are the ketones II:

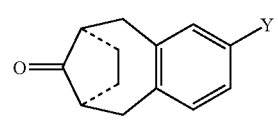

wherein Y represents alkoxycarbonyl (especially $CO_2Me$ or $CO_2Et$), nitro or benzyloxy. Treatment of the ketones II with t-butylsulphonamide in the presence of $TiCl_4$ and triethylamine in refluxing dichloroethane provides the sulphonylimines III(a):

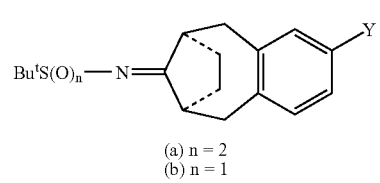

(a) n = 2
(b) n = 1 where Y has the same meaning as before. Alternatively, treatment of the ketones II with t-butylsulphinamide in the presence of $Ti(OEt)_4$ in refluxing tetrahydrofuran provides the sulphinylimines III(b).

Both types of imine III react with trimethylsulphoxonium iodide to provide aziridines IV:

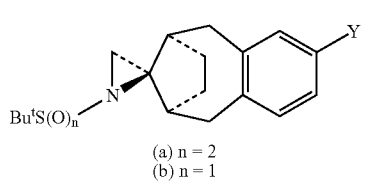

(a) n = 2
(b) n = 1 where Y has the same meaning as before. The reaction takes place in the presence of sodium hydride at ambient temperature in a THF-DMSO mixture or at 0° C. in DMSO.

Reaction of sulphonamides IV(a) with CF$_3$CH$_2$NH$_2$, followed by cleavage of the t-butylsulphonyl group, provides diamines V:

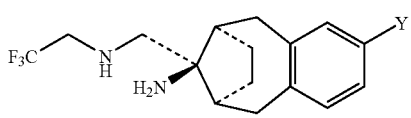

V where Y has the same meaning as before. Ring-opening of the aziridine is typically effected by heating with CF$_3$CH$_2$NH$_2$ at 100° C. in DMF or DMSO in a sealed tube, while cleavage of the t-butylsulphonyl group may be effected by treatment with trifluoromethanesulphonic acid at 0-20° C.

Alternatively, the diamines V may be formed directly by reaction of the sulphinamides IV(b) with CF$_3$CH$_2$NH$_2$ in the presence of zinc iodide in dichloroethane at 75° C.

Reaction of diamines V with sulphamide (H$_2$NSO$_2$NH$_2$) in refluxing anhydrous pyridine provides the cyclic sulphamides VI(a)-(c):

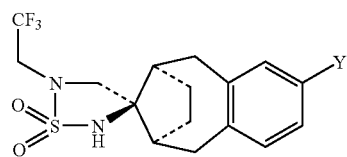

VI (a) Y = alkoxycarbonyl
(b) Y = nitro
(c) Y = benzyloxy

Compounds VI(a)-(c) are key intermediates for the preparation of compounds of formula I since the substituent Y may be transformed into the moiety —X—R by various standard synthetic techniques.

Hydrolysis of the esters VI(a) (for example, using sodium hydroxide in aqueous THF at 60° C.) provides the acid VII which serves as the precursor for a variety of heteroaryl structures.

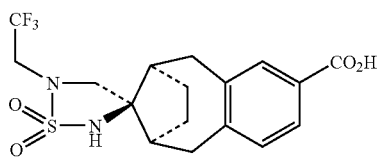

VII

In one process, the acid VII is coupled with a hydrazide R—CO—NHNH$_2$ and then reacted (a) with Burgess reagent or (b) with diphosphorus pentasulphide or Lawesson's reagent to provide, respectively, a 1,3,4-oxadiazole derivative IX(a) or a 1,3,4-thiadiazole derivative IX(b):

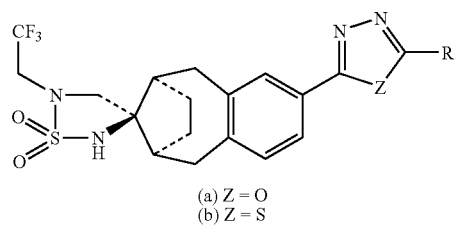

IX (a) Z = O
(b) Z = S where R has the same meaning as before. The initial coupling may be effected using HBTU in the presence of a tertiary amine in acetonitrile at 40° C. Treatment with Burgess reagent may be carried out in THF using microwave heating, and treatment with diphosphorus pentasulphide may be carried out in refluxing pyridine.

In another process, the acid VII is first reacted with carbonyldiimidazole and then with an anion derived from an acetyl derivative R—COCH$_3$. Treatment of the resulting □-diketone with R$^1$NHNH$_2$ then provides the preferred pyrazoles X(a) and X(b):

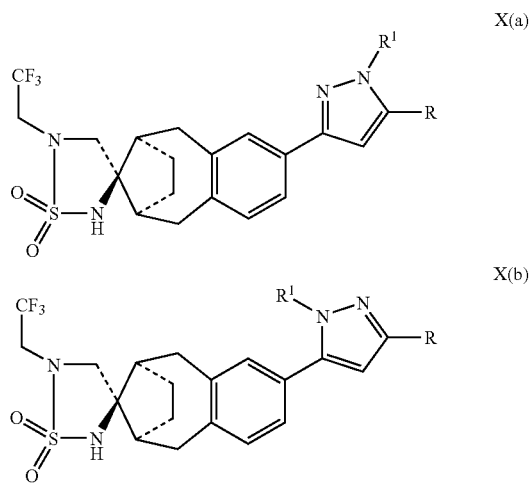

X(a)

X(b)

where R$^1$ is H or a hydrocarbon group of up to 5 carbon atoms optionally substituted with up to 3 halogen atoms (preferably methyl) and R has the same meaning as before (preferably substituted phenyl). The anion is typically generated by treatment of R—COCH$_3$ with lithium diisopropylamide in THF at −78° C. and reacted in situ. Reaction with the hydrazine is conveniently carried out in refluxing ethanol. When R$^1$ is other than H, the positional isomers X(a) and X(b) are formed in approximately equal proportions, and may be separated by preparative HPLC.

In another process, the acid VII is coupled with an amine R—COCH$_2$NH$_2$, then treated (a) with Burgess reagent or (b) with Lawesson's reagent to provide, respectively, an oxazole derivative XI(a) or a thiazole derivative XI(b):

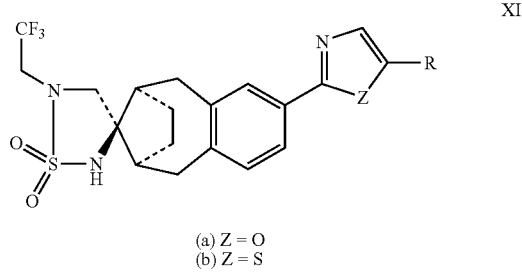

XI (a) Z = O
(b) Z = S where R has the same meaning as before. The initial coupling may be effected using HBTU in the presence of a tertiary amine in acetonitrile at 50° C. Treatment with Burgess reagent may be carried out in THF using microwave heating, and treatment with Lawesson's reagent may be carried out in refluxing toluene.

For the synthesis of oxazoles or thiazoles of formula XI in which R is N(R$^a$)$_2$ or N-heterocyclyl, it is advantageous to carry out the initial coupling of the acid VII with glycine ethyl ester, and to react the product with $(R^3)_2NH$, where the $R^3$ groups represent $R^a$ (as defined previously) or complete a heterocyclic ring within the definition of R. Treatment of the resulting bis-amides with Burgess reagent or Lawesson's reagent, as described above, then provides the desired oxazoles or thiazoles.

In another process, the acid VII is converted to the corresponding hydrazide, then reacted with a thioamide R—CS—$NH_2$ to form a 1,2,4-triazole derivative XII:

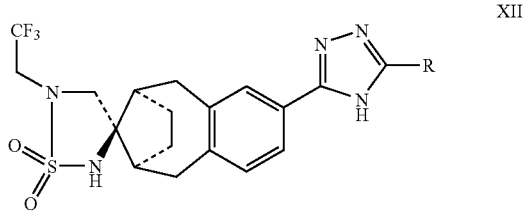

XII where R has the same meaning as before. Conversion of VII to the hydrazide is conveniently effected by treatment with BOC—$NHNH_2$ in the presence of HBTU and a tertiary amine in acetonitrile at 20° C., followed by cleavage of the BOC protecting group with HCl at ambient temperature in ethyl acetate. Reaction with R—CS—$NH_2$ is carried out at elevated temperature, e.g. 200° C.

Alternatively, the acid VII (or its ester precursor VI(a)) may be reduced to the corresponding aldehyde and treated with $R^1NHNH_2$ to provide the corresponding hydrazone, then reacted with a hydroximinoyl chloride R—C(Cl)=NOH to provide a 1,2,4-triazole XIII:

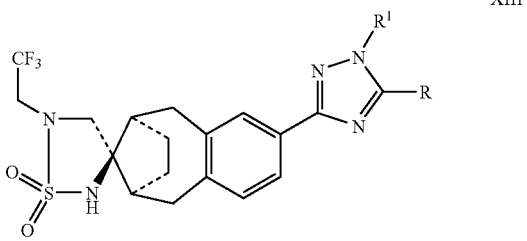

XIII where R and $R^1$ have the same meanings as before. The aldehyde is conveniently formed by reduction of VI(a) with diisobutylaluminium hydride at −78 to −10° C. in THF to provide the benzyl alcohol, which is then oxidised to the aldehyde using pyridinium dichromate in dichloromethane at room temperature. Formation of the hydrazone takes place in THF at room temperature, while the final step may be carried out in THF at −10 to 20° C. in the presence of triethylamine, followed by refluxing in acetic acid.

The nitro derivative VI(b) may be reduced (e.g. using zinc and acetic acid) to the aniline XV:

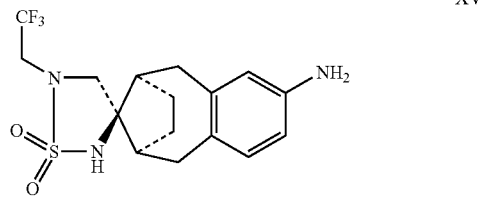

XV which is a precursor for certain compounds of formula I in which X is bonded through nitrogen. For example, diazotisation of XV followed by reaction with azide ion provides the corresponding azide, which may undergo cycloaddition with an alkyne R—C≡CH to form a 1,2,3-triazole XVI:

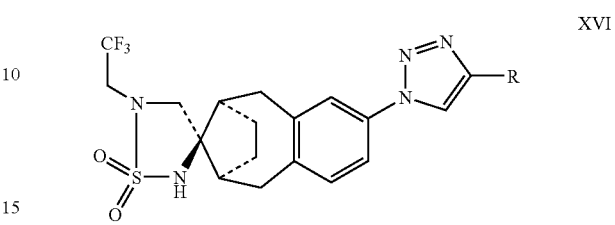

XVI where R has the same meaning as before. Diazotisation may be carried out under standard conditions (sodium nitrite in aqueous HCl at 0° C.), and reaction of the diazonium salt with azide ion is typically carried out in situ. Cycloaddition with R—C≡CH may be carried out by refluxing in xylene.

The benzyl ether VI(c) may be converted to the corresponding phenol by hydrogenation over Pd/C, and thence to the triflate XVII by treatment with triflic anhydride in the presence of pyridine in dichloromethane at 0-20° C.:

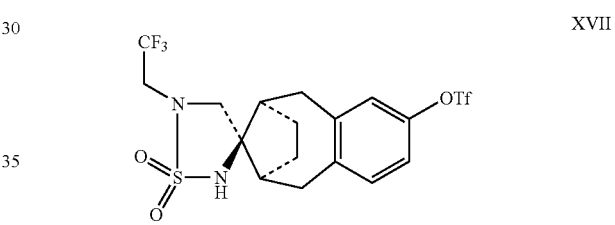

XVII where Tf represents triflyl (i.e. trifluoromethanesulphonyl). The triflate XVII is another precursor of compounds in accordance with formula I.

For example, treatment of XVII with trimethylsilylacetylene in the presence of a Pd(0) catalyst, CuI and an amine, followed by treatment with lithium hydroxide, provides the corresponding acetylene derivative, which undergoes cycloaddition with nitrile oxides R—C≡$N^+$—$O^-$ to provide isoxazoles XVIII:

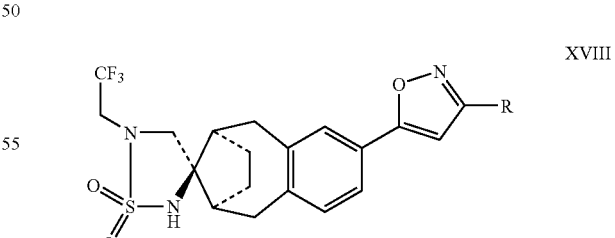

XVIII where R has the same meaning as before. Cycloaddition of R—$N_3$ to the aforesaid acetylene derivative (e.g. by refluxing in xylene) provides the 1-(R-substituted)-1,2,3-triazol-4-yl isomers of XVI, where R is preferably optionally-substituted hydrocarbon, C-heterocyclyl, phenyl or heteroaryl.

Alternatively, XVII may be converted to a boronic acid derivative XIX:

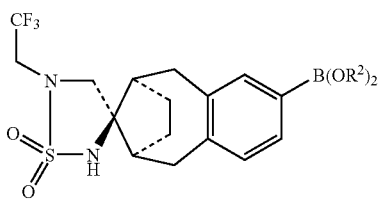

XIX where $R^2$ represents H or alkyl, or the two $OR^2$ groups complete a cyclic boronate ester such as the pinacolate or the neopentyl glycolate. The conversion may be achieved by conventional means using a suitable boron reagent, such as bis(pinacolato)diboron, in the presence of a Pd catalyst such as bis(diphenylphosphinoferrocene)dichloropalladium(II) or tetrakis(triphenylphosphine)palladium(0), typically in the presence of an inorganic base such as potassium acetate or sodium carbonate, in a solvent such as DMF or toluene at about 100° C.

Reaction of boronates XIX with R—X—L, where L is a suitable leaving group (such as halogen, especially bromine or iodine, triflate or nonaflate) and R and X have the same meanings as before, provides compounds of formula I directly. The reaction takes place under similar conditions in the presence of the same Pd catalysts as used in the preparation of XIX.

As an example of this strategy, boronate XIX may be reacted with a bromoimidazole XX:

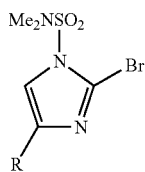

XX where R has the same meaning as before. Removal of the dimethylaminosulphonyl protecting group (e.g. by reflux in a mixture of THF and hydrochloric acid) then provides a compound of formula I in which R—X— represents a 4-substituted-1H-imidazol-2-yl moiety.

Other notable examples of compounds R—X—L which may similarly undergo coupling via boronates XIX include 4-bromo-1-(R-substituted) imidazoles and 3-bromo-1-(R-substituted)-1,2,4-triazoles, where R is preferably optionally-substituted hydrocarbon, C-heterocyclyl, phenyl or heteroaryl.

When the group X comprises an NH functionality in the ring (as in imidazole, for example), reaction of boronic acid XIX ($R^2$=H) with R—X—H provides compounds of formula I in which X is bonded to the fused benzene ring through nitrogen. The reaction takes place at ambient temperature in dichloromethane in the presence of di-µ-hydroxo-bis(N,N,N',N'-tetramethylethylenediamine)copper (II) chloride.

Alternatively, the R—X moiety may be assembled in a three-stage process in which firstly an HX— group is introduced by reaction of boronate XIX with HX—L, where L and X have the same meanings as before; secondly, the resulting product is brominated to convert the HX— group to Br—X—; and thirdly, reaction with R—B($OR^2$) provides a compound of formula I, where R and $R^2$ have the same meanings as before.

In another process, the triflate VI(c) is reacted with tributyl(1-ethoxyvinyl)tin to form the acetyl derivative XXI (a):

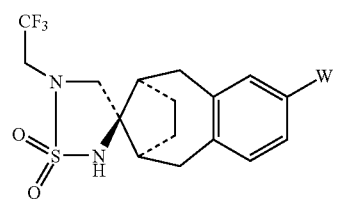

XXI (a) W = $COCH_3$
(b) W = $COCH_2CHOH$—R
(c) W = COCH=CH—R
(d) W = $COCH_2CO_2Et$

The reaction takes place in DMF in a sealed tube at 100° C. in the presence of LiCl, triphenylphosphine and Pd(II) acetate. Aldol condensation of XXI(a) with R—CHO provides the hydroxyketone XXI(b), which may be dehydrated to the enone XXI(c), where R has the same meaning as before. The aldol condensation takes place at low temperature (e.g. −78° C.) in THF in the presence of a strong base such as lithium bis(trimethylsilyl)amide. The dehydration may be effected by treatment with cerium(III) chloride and sodium iodide in refluxing acetonitrile.

Reaction of the enones XXI(c) with hydrazines $R^1NHNH_2$, where $R^1$ has the same meaning as before, followed by oxidation of the resulting adduct with DDQ, provides an alternative route to the pyrazoles X(a) and X(b), with X(a) as the major product. The reaction with the hydrazine takes place at ambient temperature in ethanol under nitrogen, while the oxidation may be carried out in THF at ambient temperature.

In another route to the pyrazoles X(a), the carboxylic acid VII is converted to the acid chloride, then added to a mixture of ethyl hydrogen malonate and isopropylmagnesium bromide at −78° C. in THF, followed by treatment with aqueous HCl, to form the β-ketoester XXI(d). Reaction of this intermediate with $R^1NHNH_2$ (e.g. in acetic acid at ambient temperature) provides pyrazolones XXII:

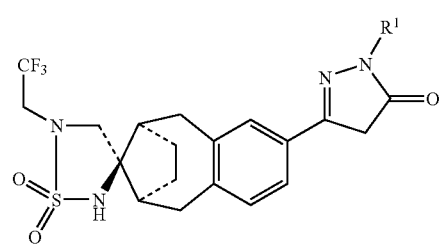

XXII where $R^1$ has the same meaning as before, which form the triflates XXIII by treatment with triflic anhydride and pyridine in dichloromethane at −78° C.:

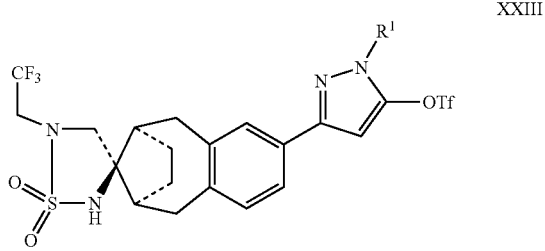

where R¹ has the same meaning as before. Triflates XXIII react with R—B(OR²)₂ as described previously to form pyrazoles X(a).

In another route to the pyrazoles X(a), boronic acid derivative XIX is reacted with a compound XXIV under the conditions described previously:

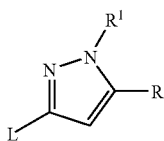

where L, R and R¹ have the same meanings as before. Compounds XXIV in which L is triflate or nonaflate are accessible from the reaction of alkynes R—C≡C—CO₂Me with R¹NHNH₂ and treatment of the resulting pyrazolones with triflic anhydride or nonafluorobutanesulfonyl fluoride respectively. Compounds XXIV in which L is Br are available by reaction of nonaflates XXV with RZnBr:

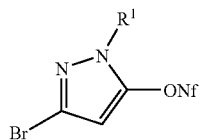

where Nf represents nonafluorobutanesulfonyl, and R and R¹ have the same meaning as before.

It will be apparent to those skilled in the art that in the above-described routes to compounds of formulae IX, X, XII, XIII, XVI and XVIII, or in the routes involving R—B(OR²)₂, R is most suitably an optionally-substituted hydrocarbon, C-heterocyclyl, phenyl or heteroaryl group, and in particular an optionally-substituted phenyl or heteroaryl group.

It is emphasised that the above formulae II-VII, IX-XIII, XV-XIX and XXI-XXIII represent both of the enantiomeric forms arising from the overall asymmetry of the molecules, either singly or in mixtures of any proportion.

It will be apparent to those skilled in the art that, in many cases, the steps in the synthetic schemes described above may be carried out in a different order. Thus, if desired, the group Y in ketones II may be converted to the moiety R—X— by one of the described routes prior to the construction of the spiro-linked sulphamide ring.

It will also be appreciated that where more than one isomer can be obtained from a reaction then the resulting mixture of isomers can be separated by conventional means.

Where the above-described process for the preparation of the compounds according to the invention gives rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The novel compounds may also be resolved by formation of diastereomeric esters or amides, followed by chromatographic separation and removal of the chiral auxiliary. Alternatively, such techniques may be carried out on racemic synthetic precursors of the compounds of interest.

In a preferred route to enantiomerically pure compounds of formula I, racemic intermediates VI(a) or VI(c) are subjected to preparative chiral HPLC to provide the corresponding homochiral intermediates, which are then converted to homochiral compounds of formula I by the routes indicated above.

Alternatively, intermediate II (Y=nitro) is reduced to the corresponding racemic aniline, and resolved via salt formation with (+) or (−) mandelic acid. The resulting homochiral aniline is converted to the corresponding phenol (via the corresponding diazonium salt) and thence to the homochiral benzyl ether II (Y=benzyloxy), which may then be converted to homochiral compounds of formula I by the methods outlined above.

Where they are not commercially available, the starting materials and reagents used in the above-described synthetic schemes may be prepared by conventional means. The ketones II may be prepared by the method described in *J. Org. Chem.*, 47, 4329-34, 1982.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

An assay which can be used to determine the level of activity of compounds of the present invention is described in WO01/70677. A preferred assay to determine such activity is as follows:

1) SH-SY5Y cells stably overexpressing the βAPP C-terminal fragment SPA4CT, are cultured at 50-70% confluency. 10 mM sodium butyrate is added 4 hours prior to plating.

2) Cells are plated in 96-well plates at 35,000 cells/well/100 μL in Dulbeccos minimal essential medium (DMEM) (phenol red-free)+10% foetal bovine serum (FBS), 50 mM HEPES buffer (pH7.3), 1% glutamine.

3) Make dilutions of the compound plate. Dilute stock solution 18.2x to 5.5% DMSO and 11x final compound concentration. Mix compounds vigorously and store at 4° C. until use.

4) Add 10 μL compound/well, gently mix and leave for 18 h at 37° C., 5% CO₂.

5) Prepare reagents necessary to determine amyloid peptide levels, for example by Homogeneous Time Resolved Fluorescence (HTRF) assay.

6) Plate 160 μL aliquots of HTRF reagent mixture to each well of a black 96-well HTRF plate.

7) Transfer 40 μL conditioned supernatant from cell plate to HTRF plate. Mix and store at 4° C. for 18 hours.

8) To determine if compounds are cytotoxic following compound administration, cell viability is assessed by the use of redox dye reduction. A typical example is a combination of redox dye MTS (Promega) and the electron coupling reagent PES. This mixture is made up according to the manufacturer's instructions and left at room temperature.

9) Add 10 μL/well MTS/PES solution to the cells; mix and leave at 37° C.

10) Read plate when the absorbance values are approximately 0.4-0.8. (Mix briefly before reading to disperse the reduced formazan product).

11) Quantitate amyloid beta 40 peptide using an HTRF plate reader.

Alternative assays are described in *Biochemistry*, 2000, 39(30), 8698-8704.

See also, *J. Neuroscience Methods*, 2000, 102, 61-68.

The compounds of the present invention show unexpectedly high affinities as measured by the above assays. Thus the following Examples all had an $ED_{50}$ of less than 50 nM, typically less than 10 nM, and frequently less than 1 nM in at least one of the above assays. In general, the compounds also exhibit good oral bioavailability and/or brain penetration, and are largely free from undesirable biological interactions likely to lead to toxic side effects.

The following examples illustrate the present invention.

EXAMPLES

Intermediate A [6S/R,9R/S,11R/S] 2',3',4',5,5',6,7,8,9,10-Decahydro-2-carboxy-5'-(2,2,2-trifluoroethyl)-spiro[6,9-methanobenzocyclooctene-11,3'-[1,2,5]thiadiazole] 1',1'-dioxide

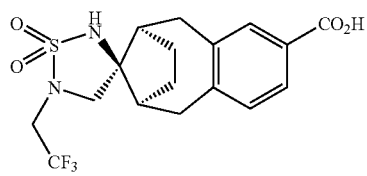

Step 1: Methyl 11-Oxo-5,6,7,8,9,10-hexahydro-6,9-methanobenzocyclooctene-2-carboxylate

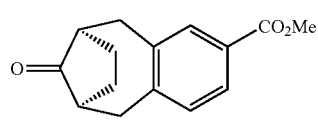

Prepared using the procedure described for 11-oxo-5,6,7,8,9,10-hexahydro-6,9-methanobenzocyclooctene (Justus Liebigs Ann. Chem. 1961, 650, 115) using methyl 3,4-bis(bromomethyl)benzoate in place of 1,2-bis(bromomethyl)benzene.

Step 2: Methyl 11-(2'-Methyl-propane-2'-sulfonylimino)-5,6,7,8,9,10-hexahydro-6,9-methanobenzocyclooctene-2-carboxylate

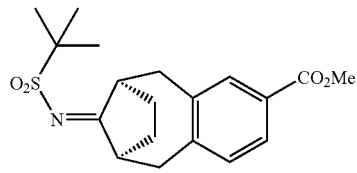

A solution of titanium (TV) chloride (25 mL, 1M in DCM) was added at r.t. to a stirred suspension of the ketone from Step 1 (10.0 g), tert-butyl sulfonamide (5.8 g) and triethylamine (11.6 mL) in 1,2-dichloroethane (100 mL). The yellow suspension was stirred under nitrogen for 30 minutes, then refluxed for 8 hours. The mixture was diluted with dichloromethane (400 mL) and saturated aqueous sodium hydrogencarbonate (400 mL) and filtered through a pad of Celite. The organic phase was dried ($Na_2SO_4$), filtered and concentrated to give the sulfonimine (15.5 g, quantitative) as a brown gum. δ ($^1$H, 360 MHz, $CDCl_3$) 1.20-1.40 (2H, m), 1.50 (9H, s), 1.75-2.00 (2H, m), 2.90-2.95 (2H, m), 3.05-3,20 (3H, m), 3.92 (3H, s), 3.95-4.05 (1H, m), 7.24-7.28 (1H, m), 7.84-7.87 (2H, m).

Step 3: Methyl [6S/R,9R/S,11R/S]-11-[(2'-Methyl-propane-2'-sulfonyl)-1'-aza-spirol[2,4]]-5,6,7,8,9,10-hexahydro-6,9-methanobenzocyclooctene-2-carboxylate

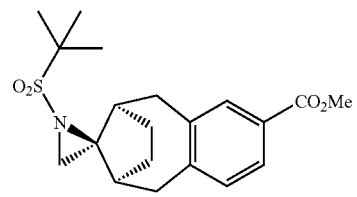

Sodium hydride (55%, 1.75 g) was added portionwise at room temperature to a stirred suspension of trimethylsulfoxonium iodide (8.8 g) in DMSO (70 mL) under nitrogen. After stirring for 2 hours, the solution was cooled in an ice-bath and a solution of the sulfonimine from Step 2 (10.0 g) in DMSO (80 mL) was added. The mixture was stirred at room temperature for 2.5 hours then poured onto ice (500 mL) and diluted with water (200 mL). The white solids were collected, rinsed with diethyl ether and dried under vacuum at room temperature to give the aziridine (8.16 g, 79%). MS (ES+) 400 ([MNa]$^+$).

Step 4: Methyl [6S/R,9R/S,11R/S]-11-(2'-Methyl-propane-2'-sulfonylamino)-11-(2,2,2-trifluoroethyl)aminomethyl-5,6,7,8,9,10-hexahydro-6,9-methanobenzocyclooctene-2-carboxylate

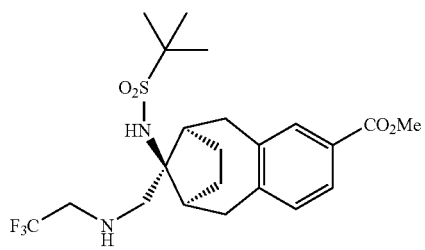

A solution of the aziridine from Step 3 (8.16 g) and 2,2,2-trifluoroethylamine (10.2 mL) in DMSO (45 mL) was divided into 3 equal portions and stirred at 100° C. in sealed tubes for 6 days. The cooled solutions were combined and poured into water (250 mL). The white crystalline solid was collected, rinsed with diethyl ether and dried under vacuum at room temperature to give the amine (7.43 g, 72%). MS (ES+) 477 ([MH]⁺).

Step 5: Methyl [6S/R,9R/S,11R/S] 11-Amino-11-(2,2,2-trifluoroethyl)aminomethyl-5,6,7,8,9,10-hexahydro-6,9-methanobenzocyclooctene-2-carboxylate

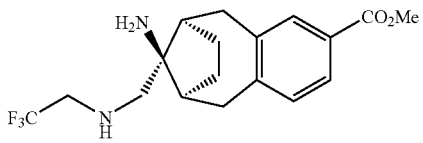

Trifluoromethanesulfonic acid (11 mL) was added dropwise at 0° C. to a stirred suspension of the sulfonamide from Step 4 (7.43 g) in dichloromethane (100 mL) under nitrogen. The mixture was stirred at 0° C. for 20 minutes, then at room temperature for 4 hours. The mixture was poured into saturated aqueous sodium hydrogencarbonate (600 mL) and extracted with 10% methanol-dichloromethane (2×300 mL). The extracts were washed with brine (100 mL), dried over $Na_2SO_4$, filtered and concentrated to give the diamine (6.5 g, quantitative) as a yellow oil. MS (ES+) 357 ([MH]⁺).

Step 6: [6S/R,9R/S,11R/S] 2',3',4',5,5',6,7,8,9,10-Decahydro-2-carbomethoxy-5'-(2,2,2-trifluoroethyl)-spiro[6,9-methanobenzocyclooctene-11,3'-[1,2,5]thiadiazole] 1',1'-dioxide

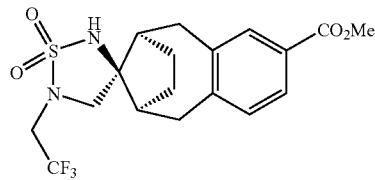

A solution of the diamine from Step 5 (6.5 g) and sulfamide (4.5 g) was refluxed in pyridine (120 mL) for 6 hours. Solvent was removed by evaporation. The residue was partitioned between 1M HCl (200 mL) and 10% methanol-dichloromethane (500 mL). The organic extract was washed with brine (100 mL), dried over $Na_2SO_4$, filtered and concentrated. The solid was rinsed with diethyl ether to give the cyclic sulfamide (5.26 g, 80%) as an off-white powder. δ (¹H, 360 MHz, CDCl₃) 1.26-1.30 (2H, m), 1.70-1.75 (2H, m), 2.47-2.50 (2H, m), 2.74-2.82 (2H, m), 3.21-3.29 (2H, m), 3.41-3.47 (2H, m), 3.68 (2H, q, J=9 Hz), 3.90 (3H, s), 4.78 (1H, s), 7.17 (1H, d, J=8 Hz), 7.78-7.80 (2H, m)

Step 7: [6S/R,9R/S,11R/S] 2',3',4',5,5',6,7,8,9,10-Decahydro-2-carboxy-5'-(2,2,2-trifluoroethyl)-spiro[6,9-methanobenzocyclooctene-11,3'-[1,2,5]thiadiazole] 1',1'-dioxide

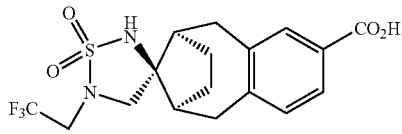

A mixture of 4M sodium hydroxide (3 mL) and the ester from Step 6 (2.33 g) in tetrahydrofuran (30 mL) was stirred at 60° C. for 3.5 hours. The mixture was diluted with 1M citric acid (10 mL) and 1M hydrochloric acid (20 mL) and extracted with dichloromethane (2×100 mL). The extracts were washed with water (100 mL), brine (100 mL), dried over $Na_2SO_4$, filtered and concentrated. Trituration with diethyl ether-isohexane gave the acid (1.96 g, 88%) as an off-white solid. δ (¹H, 360 MHz, d₆-DMSO) 0.95-1.05 (2H, m), 1.65-1.75 (2H, m), 2.35-2.42 (2H, m), 2.62-2.72 (2H, m), 3.18-3.23 (2H, m), 3.47 (2H, s), 4.02 (2H, q, J=10 Hz), 7.23 (1H, d, J=8 Hz), 7.62-7.70 (2H, m), 8.03 (1H, s), 12.60 (1H, s).

Intermediate B (−)-[6S,9R,11R] 2',3',4',5,5',6,7,8,9,10-Decahydro-2-carboxy-5'-(2,2,2-trifluoroethyl)-spiro[6,9-methanobenzocyclooctene-11,3'-[1,2,5]thiadiazole] 1',1'-dioxide

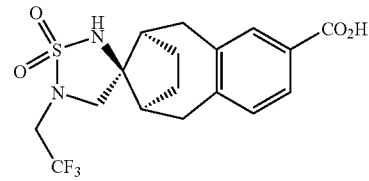

The racemic acid Intermediate A was resolved by supercritical fluid chromatographic separation on a Chiralcel OD (20 um) column using 22% methanol-sc-CO₂ (with 0.1% trifluoroacetic acid) as eluant at 35° C., 100 bar and UV detection at 250 nm. The first eluted compound under these conditions was the (−)-enantiomer of the acid. [α]_D=−8 (c=1, Methanol, 23° C.).

Intermediate C [6S/R,9R/S,11R/S] 2',3',4',5,5',6,7,8,9,10-Decahydro-2-amino-5'-(2,2,2-trifluoroethyl)-spiro[6,9-methanobenzocyclooctene-11,3'-[1,2,5]thiadiazole] 1',1'-dioxide

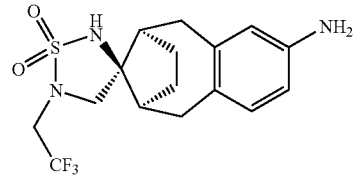

Step 1: 11-(2'-Methyl-propane-2'-sulfonylimino)-5,6,7,8,9,10-hexahydro-2-nitro-6,9-methanobenzocyclooctene

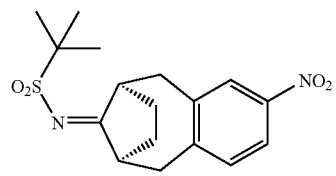

Triethylamine (6 mL, 43.2 mmol) was added to a stirred suspension of 11-oxo-5,6,7,8,9,10-hexahydro-2-nitro-6,9-methanobenzocyclooctene (5.0 g, 21.6 mmol; *J. Org. Chem.* 47, 4329, 1982), tert-butyl sulphonamide (2.97 g, 21.6 mmol) and titanium (IV) chloride (1.0 M in dichloromethane, 13 mL, 13 mmol) in 1,2-dichloroethane (50 mL) at room temperature under nitrogen. The reaction was heated under reflux for 6.5 hours then allowed to cool to room temperature. The reaction mixture was poured into water (250 mL), hydrochloric acid (2 M, 100 mL) and dichloromethane (200 mL) and filtered through Celite®. The layers were separated and the organic layer washed with brine, dried over Na$_2$SO$_4$ and concentrated to give the imine (6.85 g containing 5% starting nitroketone, 87% yield of imine). MS (ES+) 231 ([MH]$^+$).

Step 2: [6S/R,9R/S,11R/S]-11-(2'-Methyl-propane-2'-sulfonylamino)-11-(2,2,2-trifluoroethyl)aminomethyl-5,6,7,8,9,10-hexahydro-2-nitro-6,9-methanobenzocyclooctene

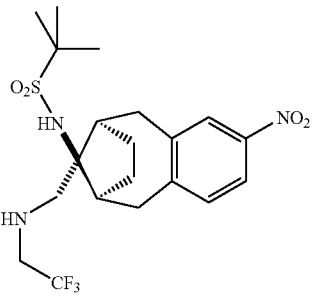

Sodium hydride (60% dispersion in mineral oil, 1.1 g, 27.4 mmol) was added portionwise to a suspension of trimethylsulphoxonium iodide (6.0 g, 27.4 mmol) in dry dimethylsulphoxide (35 mL) at room temperature under nitrogen and stirred for 1.5 hours. The solution was cooled in an ice-bath (resulting in partial freezing) and a solution of the imine from Step 1 (6.85 g containing 5% starting material, 18.9 mmol) in warm dry dimethylsulphoxide (45 mL) was added dropwise over 15 mins. The resulting partially frozen mixture was allowed to warm to room temperature and stirred for 18 hours. The mixture was poured onto ice (250 mL) and diluted with ice-cold water (250 mL). The resulting precipitate was collected by filtration and washed with water, then dissolved in dichloromethane. This organic layer was washed with water and brine, dried over Na$_2$SO$_4$ and evaporated. The residue was purified by flash column chromatography on silica, eluting with 20% ethyl acetate-isohexane to give clean aziridine (3.1 g, 45%) and some containing 12% epoxide (1.72 g, approx. 23% yield of aziridine).

A mixture of 2.05 g (5.6 mmol) of the aziridine and 2,2,2-trifluoroethylamine (2.9 mL, 36.5 mmol) in dimethylsulphoxide (10 mL) was heated at 100° C. in a sealed tube behind a blast shield for 4 days. Another 1 mL of 2,2,2-trifluoroethylamine was added and the mixture heated at 100° C. in a sealed tube behind a blast shield for 18 hours. The cooled reaction mixture was diluted with ethyl acetate (50 mL), washed with water (3×50 mL) and brine, dried over Na$_2$SO$_4$ and evaporated to give the product sulphonamide (2.18 g, 84%). MS (ES+) 464 ([MH]$^+$).

Step 3: [6S/R,9R/S,11R/S] 11-Amino-11-(2,2,2-trifluoroethyl)aminomethyl-5,6,7,8,9,10-hexahydro-2-nitro-6,9-methanobenzocyclooctene

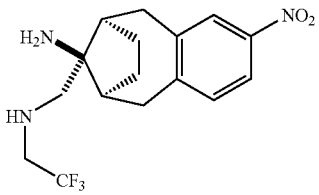

The sulphonamide from Step 2 (2.18 g, 4.7 mmol) was dissolved in dry dichloromethane (30 mL) under nitrogen and cooled to 0° C. Trifluoromethanesulphonic acid (3.33 mL, 37.6 mmol) was added dropwise and the resulting orange solution stirred at 0° C. for 10 mins then allowed to warm to room temperature for 1 hour. The reaction was carefully quenched with NaHCO$_3$ (sat. aq; 200 mL) and extracted with dichloromethane (2×150 mL). The combined organic layers were washed with brine, dried over Na$_2$SO$_4$ and evaporated to give diamine (1.6 g, 99%). MS (ES+) 344 ([MH]$^+$).

Step 4: [6S/R,9R/S,11R/S] 2',3',4',5,5',6,7,8,9,10-Decahydro-2-nitro-5'-(2,2,2-trifluoroethyl)-spiro[6,9-methanobenzocyclooctene-11,3'-[1,2,5]thiadiazole] 1',1'-dioxide

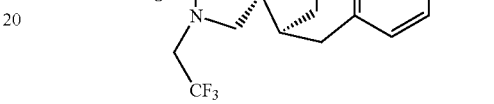

A mixture of diamine from Step 3 (1.6 g, 4.7 mmol) and sulphamide (1.36 g, 14.1 mmol) in pyridine (30 mL) was heated under reflux for 18 hours. The pyridine was removed in vacuo. The residue was partitioned between ethyl acetate (200 mL) and hydrochloric acid (1 M, 200 mL). The aqueous layer was extracted with ethyl acetate (200 mL). The combined organic layers were washed with water and brine, dried over Na$_2$SO$_4$ and evaporated. The residue was triturated in diethyl ether to give the cyclic sulphamide nitro compound (1.36 g, 71%).

Λ ($^1$H, 400 MHz, CDCl$_3$) 1.24-1.32 (2H, m), 1.77-1.81 (2H, m), 2.51-2.55 (2H, m), 2.82-2.88 (2H, m), 3.29 (1H, d, J=11 Hz), 3.33 (1H, d, J=1 Hz), 3.42-3.48 (2H, m), 3.70 (2H, q, J=9 Hz), 4.69 (1H, s), 7.27 (1H, d, J=8 Hz), 7.97-7.99 (2H, m).

Step 5: [6S/R,9R/S,11R/S] 2',3',4',5,5',6,7,8,9,10-Decahydro-2-amino-5'-(2,2,2-trifluoroethyl)-spiro[6,9-methanobenzocyclooctene-11,3'-[1,2,5]thiadiazole] 1',1'-dioxide

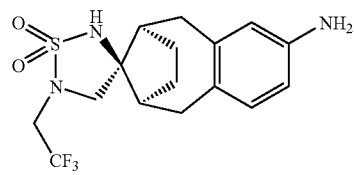

The nitro compound from Step 4 (1.36 g, 3.35 mmol) was dissolved in tetrahydrofuran (20 mL). Acetic acid (20 mL) followed by water (10 mL), were added. The solution was stirred vigorously while activated zinc (2.96 g, 45.2 mmol) was added portionwise. The reaction was stirred at room temperature for 1 hour. The zinc was removed by filtration and the filtrate concentrated in vacuo. The residue was taken up in ethyl acetate (50 mL) and carefully washed with NaHCO$_3$ (sat. aq; 50 mL). The aqueous layer was extracted with ethyl acetate (50 mL). The combined organic layers were washed with brine, dried over Na$_2$SO$_4$ and evaporated to give the title compound (1.23 g, 98%).

Λ ($^1$H, 400 MHz, CDCl$_3$) 1.34-1.39 (2H, m), 1.65-1.71 (2H, m), 2.35-2.42 (2H, m), 2.51-2.60 (2H, m), 3.05 (1H, d,

J=16 Hz), 3.15 (1H, d, J=16 Hz), 3.41 (2H, q, J=8.8 Hz), 3.55 (2H, s), 3.61-3.74 (2H, m), 4.64 (1H, s), 6.45-6.48 (2H, m), 6.86 (1H, d, J=7 Hz). MS (ES+) 376 ([MH]+).

Intermediate D [6S/R,9R/S,11R/S] 2',3',4',5,5',6,7,8, 9,10-Decahydro-2-trifluoromethanesulphonate-5'-(2, 2,2-trifluoroethyl)-spiro[6,9-methanobenzocyclooctene-11,3'-[1,2,5]thiadiazole] 1',1'-dioxide

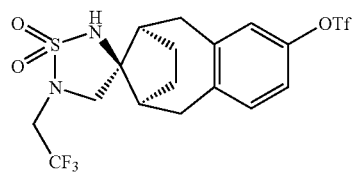

Step 1: 11-Oxo-5,6,7,8,9,10-hexahydro-2-benzyloxy-6,9-methanobenzocyclooctene

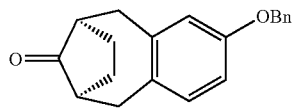

A mixture of 2-hydroxy-5,6,7,8,9,10-hexahydro-6,9-methanobenzo[α][8]annulen-11-one (15 g; J. Org. Chem 1982, 47, 4329), K₂CO₃ (20.5 g) and benzyl bromide (10.6 ml) in DMF (100 ml) was stirred for 48 hrs at room temperature. The reaction was diluted with water (500 ml) and extracted with EtOAc (3×150 ml). The combined organic phases were washed with water (2×300 ml), brine (150 ml), dried and concentrated to give a gummy oil which crystallized on standing and after trituration with ether gave the title benzyl ether (19.5 g, 90%) as a white solid. δ (¹H, 360 MHz, CDCl₃) 1.32 (2H, m), 1.85 (2H, m), 2.57 (2H, m), 2.87 (4H, m), 5.05 (2H, s), 6.82 (2H, m), 7.11 (1H, d, J=8.2 Hz), 7.37 (5H, m).

Step 2: 11-(2'-Methyl-propane-2'-sulfinylimino)-5,6,7,8,9, 10-hexahydro-2-benzyloxy-6,9-methanobenzocyclooctene

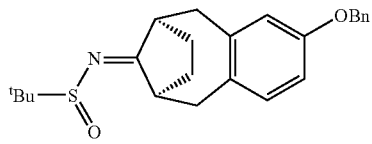

A solution of the product from Step 1 (20 g, 68 mmol), (+/−)tert-butyl sulfinamide (9.2 g, 76 mmol) and titanium (IV) ethoxide (tech., 29.2 mL, 140 mmol) in dry THF (140 mL) was stirred and heated at reflux under nitrogen for 4 hours. The reaction was allowed to cool to room temperature and poured into rapidly stirred brine (160 mL). The mixture was stirred for 20 minutes, then filtered through Hyflo□, washing with ethyl acetate. The filtrate was transferred to a separating funnel. The layers were separated, and the aqueous layer was extracted with ethyl acetate (×1). The combined organic extracts were washed with brine, then dried (Na₂SO₄), filtered and evaporated. The residue was purified by chromatography on silica, eluting with 20→30% ethyl acetate/hexanes, to give the imine (24.9 g, 93%) as a colourless solid. MS (ES+) 396 ([MH]+).

Step 3: [6S/R,9R/S,11R/S] 11-[(2'-Methyl-propane-2'-sulfinyl)-1'-aza-spiro[2,4]]-5,6,7,8,9,10-hexahydro-2-benzyloxy-6,9-methanobenzocyclooctene

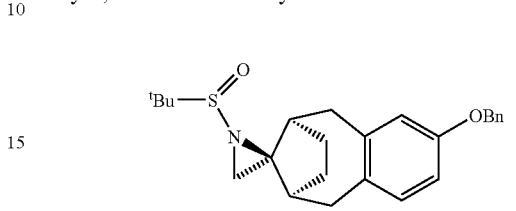

Sodium hydride (60% dispersion in oil, 3.8 g, 95 mmol) was added portionwise to a stirred suspension of trimethyl sulfoxonium iodide (21 g, 95 mmol) in dry DMSO (150 mL) at room temperature under nitrogen. After 90 minutes at room temperature, a solution of the product from Step 2 (24.9 g, 95 mmol) in dry DMSO (250 mL) was added such that the internal temperature remained below 30° C. The mixture was stirred at room temperature for 4 hours, then quenched with water (1 L). The precipitate was collected by filtration. The solid was taken up in dichloromethane and washed with brine. The organic layer was dried (Na₂SO₄), filtered and evaporated. The residue was purified by chromatography on silica, eluting with 5→10% ethyl acetate/dichloromethane, to give the aziridine (23.2 g, 90%) as a colourless solid. MS (ES+) 410 ([MH]+).

Step 4: [6S/R,9R/S,11R/S] 11-Amino-11-(2,2,2-trifluoroethyl)aminomethyl-5,6,7,8,9,10-hexahydro-2-benzyloxy-6,9-methanobenzocyclooctene

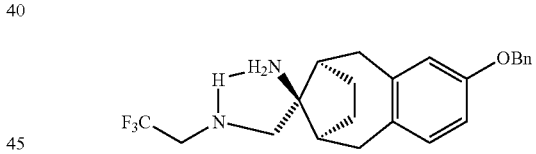

Trifluoroethyl amine (70 mL, 880 mmol) was added to a stirred suspension of the product from Step 3 (68.4 g, 167 mmol) and anhydrous zinc iodide (54 g, 170 mmol) in dry 1,2-dichloroethane (300 mL) at room temperature under nitrogen. The resulting solution was heated at 75° C., protected from light, for 24 hours. An additional portion of trifluoroethyl amine (70 mL, 880 mmol) was added and the reaction was maintained at 75° C. for a further 16 hours. The reaction was allowed to cool, then diluted with dichloromethane (500 mL) and water (400 mL). Sufficient sodium carbonate was then added to adjust the aqueous layer to ~pH 11. The small amount of precipitate was removed by filtration through Hyflo□. The layers were separated and the aqueous layer was extracted with dichloromethane (×3). The combined organic extracts were dried (Na₂SO₄), filtered and evaporated. The residue was purified by chromatography on silica, eluting with 5→10% ethyl acetate/dichloromethane, then with 10→20% methanol/dichloromethane, to give the diamine (59.6 g, 88%) as a thick oil. MS (ES+) 405 ([MH]+).

Step 5: [6S/R,9R/S,11R/S] 2',3',4',5,5',6,7,8,9,10-Decahydro-2-benzyloxy-5'-(2,2,2-trifluoroethyl)-spiro[6,9-methanobenzocyclooctene-11,3'-[1,2,5]thiadiazole] 1',1'-dioxide

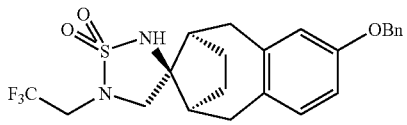

A solution of the product from Step 4 (59.6 g, 147 mmol) and sulfamide (42.5 g, 442 mmol) in dry pyridine (350 mL) was stirred and heated at reflux under nitrogen for 4 hours. The reaction was allowed to cool, then the pyridine was removed in vacuo. The residue was azeotroped with toluene (×2). The residue was then partitioned between dichloromethane (400 mL) and 1N hydrochloric acid (400 mL). The layers were separated and the aqueous layer was extracted with dichloromethane (×3). The combined organic extracts were dried ($Na_2SO_4$), filtered and evaporated. The residue was purified by chromatography on silica, eluting with dichloromethane, then 1→2→4% ethyl acetate/dichloromethane to give the cyclic sulfamide (53 g, 80%) as a colourless solid. δ ($^1H$, 360 MHz, $CDCl_3$) 1.34 (2H, m), 1.70 (2H, m), 2.41 (2H, m), 2.62 (2H, m), 3.11 (1H, d, J=15.9 Hz), 3.20 (1H, d, J=15.9 Hz), 3.42 (2H, ABq, J=9.3, 13.3 Hz), 3.67 (2H, dq, J=2.2, 8.7 Hz), 4.76 (1H, s), 5.02 (2H, s), 6.72 (2H, m), 6.99 (1H, d, J=7.8 Hz), 7.37 (5H, m).

Step 6: [6S/R,9R/S,11R/S] 2',3',4',5,5',6,7,8,9,10-Decahydro-2-hydroxy-5'-(2,2,2-trifluoroethyl)-spiro[6,9-methanobenzocyclooctene-11,3'-[1,2,5]thiadiazole] 1',1'-dioxide

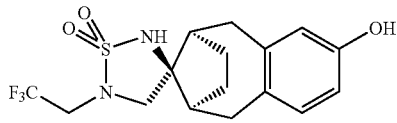

A solution of the product from Step 5 (3.9 g, 8.4 mmol) in methanol/ethyl acetate (4:1, 150 mL) was hydrogenated at 35 psi over 10% palladium on carbon (500 mg) for 4 hours at room temperature. The catalyst was removed by filtration through Hyflo®. The filtrate was evaporated, and the residue was purified by filtration through a pad of silica, eluting with 50% ethyl acetate/dichloromethane to give the phenol (3.2 g) as a colourless solid. δ ($^1H$, 360 MHz, $d_6$-DMSO) 1.06 (2H, m), 1.65 (2H, m), 2.29 (2H, m), 2.42 (2H, m), 3.04 (1H, d, J=15.6 Hz), 3.11 (1H, d, J=15.6 Hz), 3.43 (2H, s), 3.99 (2H, brq, J=9.6 Hz), 6.47 (2H, m), 6.85 (1H, d, J=8 Hz), 7.93 (1H, s), 9.02 (1H, s).

Step 7: [6S/R,9R/S,11R/S] 2',3',4',5,5',6,7,8,9,10-Decahydro-2-trifluoromethanesulphonate-5'-(2,2,2-trifluoroethyl)-spiro[6,9-methanobenzocyclooctene-11,3'-[1,2,5]thiadiazole] 1',1'-dioxide

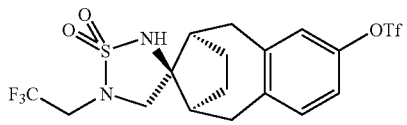

Trifluoromethanesulfonic anhydride (3.8 ml, 23 mmol) was added dropwise to a cold (0° C.) solution of the phenol from Step 6 (5.1 g, 12.8 mmol), in dichloromethane (400 ml), under a nitrogen atmosphere. Once the addition was complete the mixture was stirred at room temperature for one hour. The reaction was cooled to 0° C. and pyridine (1.9 ml, 23 mmol) was added dropwise, and the mixture was stirred at 0° C. for 15 minutes and at room temperature for 16 hours. The reaction was diluted with water (200 ml) and extracted with dichloromethane (2×200 ml). The extracts were washed with brine, dried ($MgSO_4$) and evaporated in vacuo to give a pinkish solid (5.25 g). The solid was triturated with diethyl ether to give the title compound as an off white solid (4.3 g, 66%).

δ ($^1H$, 400 MHz, $d_6$-DMSO) 0.97-1.01 (2H, m), 1.70-1.74 (2H, m), 2.32-2.41 (2H, m), 2.66-2.74 (2H, m), 3.15 (1H, d, J=6.2 Hz), 3.19 (1H, d, J=6.2 Hz), 3.46 (2H, m), 3.98-4.05 (2H, m), 7.20 (1H, dd, J=8.4 & 2.6 Hz), 7.28 (2H, t, J=8.4 Hz) and 8.04 (1H, s).

Intermediate E [6S,9R,11R] 2',3',4',5,5',6,7,8,9,10-Decahydro-2-trifluoromethanesulphonate-5' (2,2,2-trifluoroethyl)-spiro[6,9-methanobenzocyclooctene-11,3'-[1,2,5]thiadiazole] 1',1'-dioxide

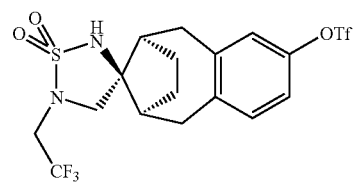

The benzyl ether from Step 5 of the Intermediate D synthesis was resolved by preparative HPLC using a Chiralcel OD column (25×2 cm), 25% $MeOH/CO_2$ @ 50 ml/min; 288 nm; 35 C; 100 bar. The second enantiomer collected was converted to the title compound using the procedures described in Steps 6 and 7 of the Intermediate D synthesis.

Alternative Method

2-Amino-11-oxo-5,6,7,8,9,10-hexahydro-6,9-methanobenzocyclooctene (*J. Org. Chem.* 47, 4329, 1982), (17.16 g, 0.085 mol) was dissolved in ethanol (430 mL) and R-(−)-mandelic acid (7.14 g, 0.047 mol) was added in one portion. The solution was slowly added into toluene (650 mL) whilst distilling the azeotrope under vacuum such that the volume was kept constant. When all of the ethanol had been added and the solution was concentrated to approximately 500 mL, the mixture was seeded with enantiopure salt (800 mg). The resulting slurry was concentrated further to a volume of 343 mL via vacuum distillation and then allowed to stir overnight. The solids were filtered, washed with toluene (53 mL) and dried. This product (16.07 g, 87% ee) was added to a 95:5 mixture of toluene and THF (402 mL) and aged at 50° C. overnight. The solids were filtered, washed with toluene (60 mL) and dried, to afford enantiopure light-orange salt (11.59 g, 38% yield, 97% e.e.). δ ($^1H$, 250 MHz, $CD_2Cl_2$): δ (ppm) 1.20 (m, 2H), 1.73 (m, 2H), 2.37 (m, 2H), 2.56 (d, 1H, J=15.3 Hz), 2.60 (d, 1H, J=14.6), 2.76 (dd, 1H, J=8.3, 15.1 Hz), 2.77 (dd, 1H, J=8.3, 15.3 Hz), 5.00 (s, 1H), 6.54 (m, 2H), 6.88 (d, 1H, J=7.8), 7.28 (m, 5H).

Treatment of this salt with base released the homochiral aniline, which could be converted to the corresponding homochiral phenol by the procedure described in *J. Org. Chem.* 47, 4329, 1982, and thence to Intermediate E by the procedures described for Intermediate D.

Example 1

[6S/R,9R/S,11R/S] 2',3',4',5,5',6,7,8,9,10-Decahydro-2-(5-(4-fluorophenyl)-1,3,4-oxadiazol-2-yl)-5'-trifluoroethyl-spiro[6,9-methanobenzocyclooctene-11,3'-[1,2,5]thiadiazole] 1',1'-dioxide.

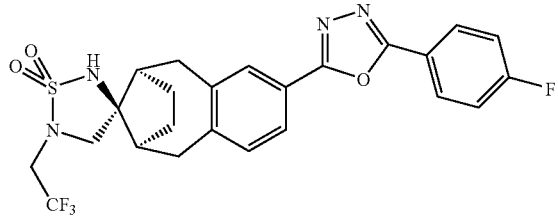

Step 1 [6S/R,9R/S,11R/S] 2',3',4',5,5',6,7,8,9,10-Decahydro-2-(carboxylic acid N'-4-fluorobenzoyl hydrazido)-5'-(2,2,2-trifluoroethyl)-spiro[6,9-methanobenzocyclooctene-11,3'-[1,2,5]thiadiazole] 1',1'-dioxide

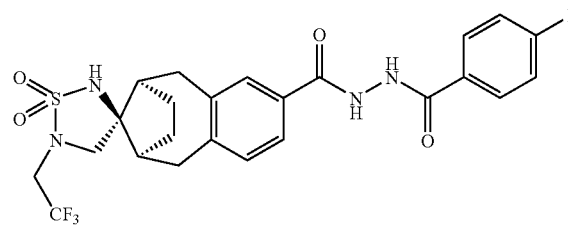

Diisopropylethylamine (83 μL) was added to a suspension of Intermediate A (160 mg) in acetonitrile (3 mL). To the resulting solution was added HBTU (180 mg) followed by 4-fluorobenzhydrazide (73 mg). The reaction mixture was heated at 40° C. for 2 h. The mixture was allowed to cool to ambient temperature and was then partitioned between water and ethyl acetate. The layers were separated and the organic extract was washed sequentially with 10% citric acid solution, water and brine. The organic phase was dried ($Na_2SO_4$) and concentrated to give the diacyl hydrazide. MS (ES+) 541 ([MH]$^+$), 563 ([M+Na]$^+$).

Step 2: [6S/R,9R/S,11R/S] 2',3',4',5,5',6,7,8,9,10-Decahydro-2-(5-(4-fluorophenyl)-1,3,4-oxadiazol-2-yl)-5'-trifluoroethyl-spiro[6,9-methanobenzocyclooctene-11,3'-[1,2,5]thiadiazole] 1',1'-dioxide

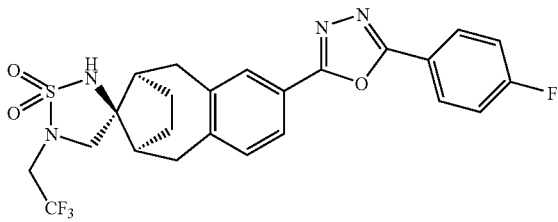

Burgess' reagent (183 mg) was added to a solution of the diacyl hydrazide from Step 1 (138 mg) in THF (2 mL) in a microwave reaction tube. The mixture was irradiated in a microwave for 600 s at 120° C. The mixture was washed into a flask using ethyl acetate and was then concentrated in vacuo. The product was purified by chromatography on silica eluting with 2 to 3 to 5% MeOH in dichloromethane. The white solid obtained was triturated with diethyl ether to give 68 mg (51% yield) of the title compound: ☐ ($^1$H, 400 MHz, $CDCl_3$) 1.31-1.39 (2H, m), 1.75-1.79 (2H, m), 2.51-2.54 (2H, m), 2.77-2.88 (2H, m), 3.29 (1H, d, J=5.6 Hz), 3.33 (1H, d, J=5.6 Hz), 3.46 (2H, s), 3.70 (2H, q, J=8.7 Hz), 4.87 (1H, br s), 7.21-7.29 (3H, m), 7.86-7.89 (2H, m), 8.13-8.17 (2H, m).

Example 2

[6S/R,9R/S,11R/S] 2',3',4',5,5',6,7,8,9,10-Decahydro-2-(2-(2-pyridyl)-1,3,4-oxadiazol-5-yl)-5'-trifluoroethyl-spiro[6,9-methanobenzocyclooctene-11,3'-[1,2,5]thiadiazole] 1',1'-dioxide

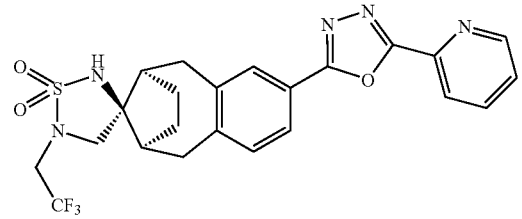

Step 1 [6S/R,9R/S,11R/S] 2',3',4',5,5',6,7,8,9,10-Decahydro-2-hydrazido-5'-(2,2,2-trifluoroethyl)-spiro[6,9-methanobenzocyclooctene-11,3'-[1,2,5]thiadiazole] 1',1'-dioxide

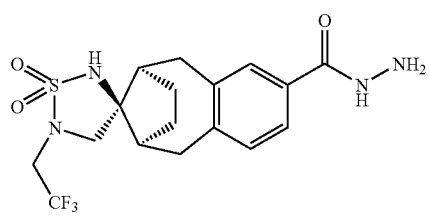

A mixture of Intermediate A (238 mg), diisopropylethylamine (113 μL), HBTU (246 mg) and BOC-hydrazine (86 mg) in acetonitrile (7 mL) was stirred at room temperature under nitrogen for 65 h. The reaction mixture was partitioned between EtOAc and water. The layers were separated and the organic extract was washed sequentially with 10% citric acid solution, water and brine. The organic phase was dried ($MgSO_4$) and concentrated. The residue was chromatographed on silica eluting with 3% methanol in dichloromethane to give 328 mg (assumed quantitative) of the BOC-hydrazide. The protected hydrazide (328 mg) was dissolved in EtOAc (5 mL) and to this solution was added HCl in diethyl ether (2 mL of a 2M solution). The mixture was stirred at room temperature overnight. After aqueous work-up, it became apparent that deprotection was incomplete. Therefore the crude material was dissolved in EtOAc (5 mL) and to this solution was added saturated HCl in methanol (3 mL). The mixture was stirred for 72 h. The mixture was diluted with EtOAc and washed with satd. $NaHCO_{3(aq)}$ (×2) and then brine before being dried ($MgSO_4$) and concentrated. The hydrazide was obtained as a solid (255 mg, 96% yield). MS (ES+) 419 ([MH]$^+$).

Step 2 [6S/R,9R/S,11R/S] 2',3',4',5,5',6,7,8,9,10-Decahydro-2-(carboxylic acid N'-2-pyridinecarbonyl hydrazido)-5'-(2,2,2-trifluoroethyl)-spiro[6,9-methanobenzocyclooctene-11,3'-[1,2,5]thiadiazole] 1',1'-dioxide

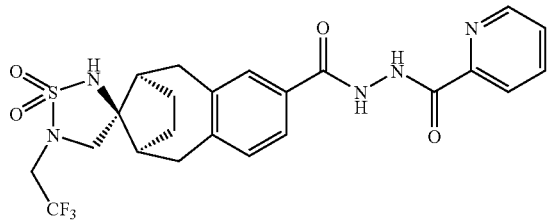

To a solution of the hydrazide from Step 1 (255 mg) in acetonitrile (5 mL) was added diisopropylethylamine (0.13 mL) followed by pyridine-2-carboxylic acid (90 mg) and HBTU (277 mg). The mixture was stirred at room temperature under nitrogen overnight. The mixture was diluted with water and extracted into EtOAc (×2). The combined organic extracts were washed with brine, dried (MgSO$_4$) and concentrated. Trituration with EtOAc/Et$_2$O afforded predominantly the diacyl hydrazide (190 mg, 60% yield). MS (ES+) 524 ([MH]$^+$).

Step 3: [6S/R,9R/S,11R/S] 2',3',4',5,5',6,7,8,9,10-Decahydro-2-(2-(2-pyridyl)-1,3,4-oxadiazol-5-yl)-5'-trifluoroethyl-spiro[6,9-methanobenzocyclooctene-11,3'-[1,2,5]thiadiazole] 1',1'-dioxide

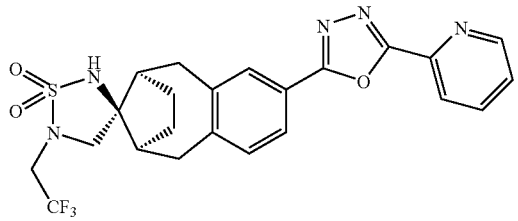

Burgess' reagent (85 mg) was added to a solution of the diacyl hydrazide (62 mg) in THF (1 mL). The mixture was irradiadiated in a microwave for 300 s at 120° C. The reaction mixture was washed out of the reaction tube using ethyl acetate, and concentrated. Chromatography on silica eluting with 2% methanol in dichloromethane was followed by trituration with diethyl ether to give the title compound (25 mg, 42%) and some slightly impure material (20 mg). δ ($^1$H, 400 MHz, CDCl$_3$) 1.32-1.35 (2H, m), 1.74-1.78 (2H, m), 2.49-2.52 (2H, m), 2.77-2.89 (2H, m), 3.25-3.33 (2H, m), 3.45 (2H, s), 3.69 (2H, q, J=8.7 Hz), 4.70 (1H, s), 7.25-7.28 (1H, m), 7.46-7.49 (1H, m), 7.89-7.93 (1H, m), 7.97-7.99 (2H, m), 8.33 (1H, d, J=8.2 Hz), 8.82 (1H, d, J=4.3 Hz); MS (ES+) 506 ([MH]$^+$).

Example 3

[6S/R,9R/S,11R/S] 2',3',4',5,5',6,7,8,9,10-Decahydro-2-(5-(4-fluorophenyl)-1,3,4-thiadiazol-2-yl)-5'-trifluoroethyl-spiro[6,9-methanobenzocyclooctene-11,3'-[1,2,5]thiadiazole] 1',1'-dioxide.

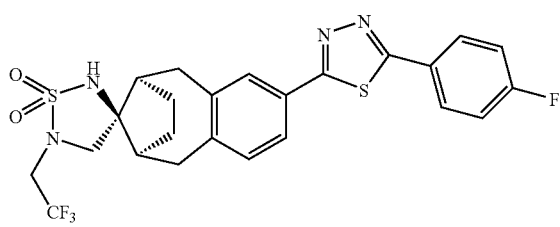

Diphosphorus pentasulphide (58 mg) was added to a solution of the diacyl hydrazide described in Example 1, Step 1 (47 mg) in pyridine (3 mL). The mixture was heated at reflux for 16 h. The mixture was allowed to cool and partitioned between EtOAc and water. The organic extract was washed sequentially with 10% citric acid solution, water and brine before being dried (MgSO$_4$) and concentrated. Chromatography eluting with 3% methanol in dichloromethane afforded the title compound (31 mg, 66% yield) as a white solid. δ ($^1$H, 400 MHz, d$_6$-DMSO) 1.06-1.10 (2H, m), 1.71-1.74 (2H, m), 2.41 (2H, br s), 2.68-2.80 (2H, m), 3.16-3.21 (2H, m), 3.48 (2H, s), 3.99-4.06 (2H, m), 7.33 (1H, d, J=7.8 Hz), 7.41-7.46 (2H, m), 7.73-7.78 (2H, m), 8.06-8.09 (3H, m); MS (ES+) 539 ([MH]$^+$).

Example 4

[6S/R,9R/S,11R/S] 2',3',4',5,5',6,7,8,9,10-Decahydro-2-(2-(2-pyridyl)-1,3,4-thiadiazol-5-yl)-5'-trifluoroethyl-spiro[6,9-methanobenzocyclooctene-11,3'-[1,2,5]thiadiazole] 1',1'-dioxide

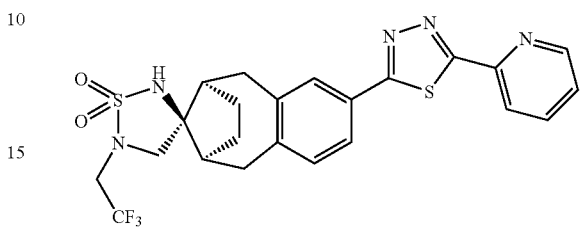

The diacyl hydrazide (80 mg) described in Example 2, Step 2 was dissolved in pyridine (4 mL) and to the solution was added diphosphorus pentasulphide (102 mg). The mixture was heated at reflux for 17 h then allowed to cool and partitioned between ethyl acetate and water. The layers were separated and the organic extract was washed sequentially with 0.5 M HCl$_{(aq)}$ (×2), water and brine before being dried (MgSO$_4$) and concentrated. The product was purified by chromatography on silica eluting with 3% methanol in dichloromethane. Trituration with 10% ethyl acetate in dichloromethane afforded the title compound as an off-white solid. δ ($^1$H, 400 MHz, d$_6$-DMSO); 1.07-1.11 (2H, m), 1.73-1.75 (2H, m), 2.42 (2H, br s), 2.68-2.82 (2H, m), 3.22-3.31 (2H, m), 3.49 (2H, s), 4.04 (2H, q, J=9.4 Hz), 7.34 (1H, d, J=7.8 Hz), 7.59-7.62 (1H, m), 7.79 (1H, d, J=7.8 Hz), 7.84 (1H, s), 8.05-8.07 (2H, m), 8.31 (1H, d, J=7.8 Hz), 8.74 (1H, d, J=4.7 Hz); MS (ES+) 522 ([MH]$^+$).

Example 5

[6S/R,9R/S,11R/S] 2',3',4',5,5',6,7,8,9,10-Decahydro-2-(5-(4-chlorophenyl)-1,2,4-triazol-3-yl)-5'-2,2,2-trifluoroethyl)-spiro[6,9-methanobenzocyclooctene-11,3'-[1,2,5]thiadiazole] 1',1'-dioxide

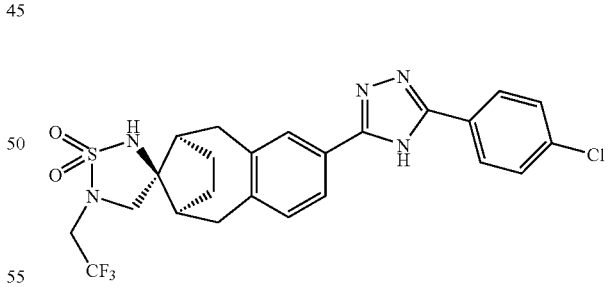

A mixture of the hydrazide from Example 2, Step 1 (0.188 g) and 4-chlorobenzenethiocarboxamide (0.086 g) was heated to 200° C. under N$_2$ for 2 hours. The mixture was cooled and dissolved in dichloromethane (2 mL). Flash column chromatography, eluting with 2% methanol-dichloromethane, then preparative thin layer chromatography, eluting with 40% ethyl acetate-isohexane, gave the triazole (0.026 g, 11%) as a white powder. δ ($^1$H, 360 MHz, CDCl$_3$) 1.23-1.32 (2H, m), 1.71-1.79 (2H, m), 2.46-2.50 (2H, m), 2.74-2.83 (2H, m), 3.24-3.31 (2H, m), 3.45 (2H, s), 3.70

(2H, q, J=9 Hz), 4.91 (1H, s), 7.22 (1H, d, J=8 Hz), 7.45 (2H, d, J=8 Hz), 7.73-7.78 (2H, m), 8.03 (2H, J=8 Hz). MS (ES+) 540, 538 ([MH]+).

Example 6

[6S/R,9R/S,11R/S] 2',3',4',5,5',6,7,8,9,10-Decahydro-2-(5-(4-fluorophenyl)-oxazol-2-yl)-5'-2,2,2-trifluoroethyl)-spiro[6,9-methanobenzocyclooctene-11, 3'-[1,2,5]thiadiazole] 1',1'-dioxide

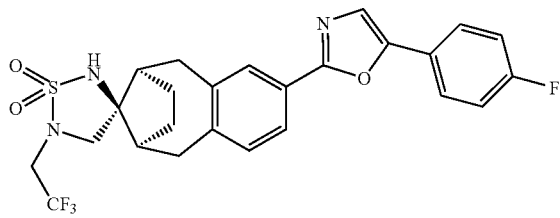

Step 1: [6S/R,9R/S,11R/S] 2',3',4',5,5',6,7,8,9,10-Decahydro-2-([2-(4-fluorophenyl)-2-oxo-ethyl]carboxamido)-5'-(2, 2,2-trifluoroethyl)-spiro[6,9-methanobenzocyclooctene-11, 3'-[1,2,5]thiadiazole] 1',1'-dioxide

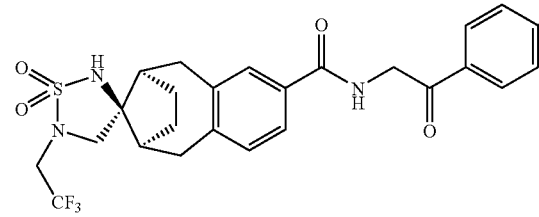

A mixture of the acid Intermediate A (0.30 g), HBTU (0.34 g), diisopropylethylamine (0.12 mL) and 2'-amino-(4-fluoroacetophenone) hydrochloride (0.16 g) in acetonitrile (5 mL) was stirred at 50° C. under nitrogen for 18 hours. The cooled suspension was diluted with water (50 mL) and the yellow solids were collected and rinsed with water and ethyl acetate. The solid was dried under vacuum at room temperature to give the ketoamide as a white powder (0.306 g, 76%). MS (ES+) 357 ([MH]+).

Step 2: [6S/R,9R/S,11R/S] 2',3',4',5,5',6,7,8,9,10-Decahydro-2-(5-(4-fluorophenyl)-oxazol-2-yl)-5'-(2,2,2-trifluoroethyl)-spiro[6,9-methanobenzocyclooctene-11,3'-[1,2,5]thiadiazole] 1',1'-dioxide

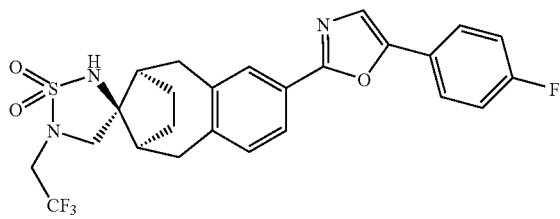

A solution of the ketoamide from Step 1 (0.30 g) and Burgess Reagent (0.30 g) in dry tetrahydrofuran (4 mL) was divided into two portions which were separately heated by microwave irradiation to give an internal temperature of 120° C. for 600 seconds. The cooled solutions were combined, diluted with water (20 mL) and extracted with ethyl acetate (2×40 mL). The combined extracts were dried over Na$_2$SO$_4$, filtered and concentrated. Flash column chromatography, eluting with 5% methanol-dichloromethane, gave a yellow foam. Trituration and rinsing with diethyl ether gave the oxazole (0.129 g, 44%) as a pale yellow solid. δ ($^1$H, 360 MHz, d$_6$-DMSO) 1.03-1.16 (2H, m), 1.55-1.70 (2H, m), 2.41-2.42 (2H, m), 2.66-2.80 (2H, m), 3.07-3.41 (4H, m), 4.04 (2H, q, J=9 Hz), 7.29-7.38 (3H, m), 7.79-7.82 (2H, m), 7.86-7.92 (3H, m), 8.07 (1H, s). MS (ES+) 522 ([MH]+).

Example 7

(−)-[6S,9R,11R] 2',3',4',5,5',6,7,8,9,10-Decahydro-2-(5-(4-fluorophenyl)-oxazol-2-yl)5'-(2,2,2-trifluoroethyl)-spiro[6,9-methanobenzocyclooctene-11,3'-[1,2,5]thiadiazole] 1',1'-dioxide

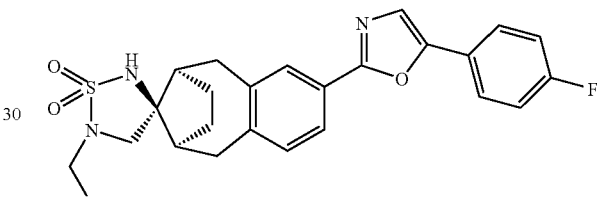

Prepared from the homochiral acid, Intermediate B, and 2'-amino-(4-fluoroacetophenone) hydrochloride by the method described for Example 6. MS (ES+) 522 ([MH]+); [α]$_D$=−19 (c=0.52, DMSO, 23° C.).

Example 8

[6S/R,9R/S,11R/S] 2',3',4',5,5',6,7,8,9,10-Decahydro-2-(5-(2-pyridyl)-oxazol-2-yl)-5'-(2,2,2-trifluoroethyl)-spiro[6,9-methanobenzocyclooctene-11,3'-[1,2,5]thiadiazole] 1',1'-dioxide.

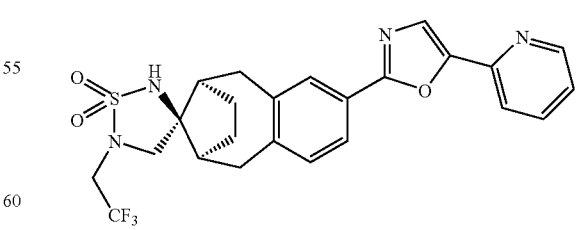

Prepared from the acid, Intermediate A, and 2-amino-1-(2-pyridyl)-1-ethanone dihydrochloride by the method described for Example 6. MS (ES+) 505 ([MH]+).

Example 9

[6S/R,9R/S,11R/S] 2',3',4',5,5',6,7,8,9,10-Decahydro-2-(5-(1,1-dimethyl-1-ethyl)-oxazol-2-yl)-5'-(2,2,2-trifluoroethyl)-spiro[6,9-methanobenzocyclooctene-11,3'-[1,2,5]thiadiazole] 1',1'-dioxide

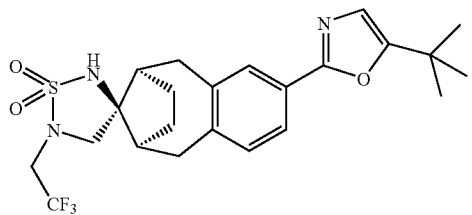

Prepared from the acid, Intermediate A, and 1-amino-3,3-dimethyl-2-butanone hydrochloride by the method described for Example 6. MS (ES+) 484 ([MH]+).

Example 10

(−)-[6S,9R,11R] 2',3',4',5,5',6,7,8,9,10-Decahydro-2-(5-(2,4-dichlorophenyl)-oxazol-2-yl)-5'-(2,2,2-trifluoroethyl)spiro[6,9-methanobenzocyclooctene-11,3'-[1,2,5]thiadiazole] 1',1'-dioxide

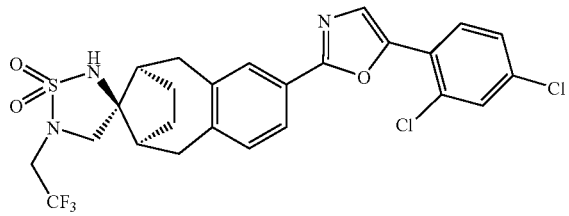

Prepared in the same way as Example 6 using 0.25 g of the acid, Intermediate B, and 2'-amino-(2,4-dichloroacetophenone) to give the title compound (0.032 g, 9% over 2 steps). MS (ES+) 572, 574, 575 ([MH]+). $\alpha_D$ −20 (c=0.57, DMSO).

Example 11

[6S/R,9R/S,11R/S] 2',3',4',5,5',6,7,8,9,10-Decahydro-2-(5-(4-fluorophenyl)-1-1H-pyrazol-3-yl)-5'-(2,2,2-trifluoroethyl)-spiro[6,9-methanobenzocyclooctene-11,3'-[1,2,5]thiadiazole] 1',1'-dioxide

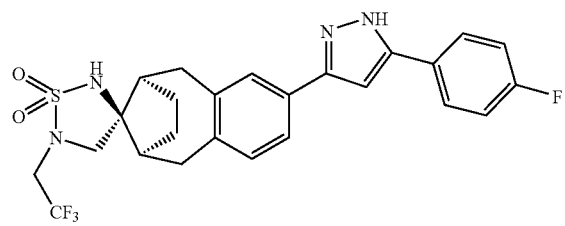

A solution of the acid, Intermediate A (0.179 g) and 1,1'-carbonyldiimidazole (0.080 g) in dry tetrahydrofuran (3 ml) was stirred at room temperature under $N_2$ for 1.5 hours. A solution of lithium diisopropylamide in dry tetrahydrofuran (3 mL) was prepared from n-butyllithium (1.6M in hexanes, 0.90 mL) and diisopropylamine (0.20 mL) at −78° C. under $N_2$. 4'-Fluoroacetophenone (0.17 mL) was added dropwise to the stirred solution of lithium diisopropylamide at −78° C.

After 1 hour, the imidazolide solution was added in a single portion to the enolate solution at −78° C. The white suspension was immediately warmed to room temperature. After 2.5 hours, the solution was diluted with 1M aqueous citric acid (20 mL) and extracted with ethyl acetate (30 mL). The extract was dried, filtered and concentrated. Flash column chromatography on silica gel, eluting with 20% ethyl acetate-hexanes, gave partially purified β-diketone (0.15 g) as a pink foam. The material was redissolved in ethanol (3 mL) with hydrazine hydrate (0.5 mL) and refluxed under $N_2$ for 7 hours. The solution was cooled, poured into water (30 mL) and extracted with dichloromethane (2×15 mL). The extracts were dried over $Na_2SO_4$, filtered and concentrated. Flash column chromatography, eluting with 98:2 then 95:5 dichloromethane-methanol, gave the pyrazole as white powder (0.053 g, 23%). δ ($^1$H, 360 MHz, CDCl$_3$) 1.33-1.36 (2H, m), 1.70-1.75 (2H, m), 2.43-2.49 (2H, m), 2.67-2.75 (2H, m), 3.23-3.27 (2H, m), 3.44 (2H, s), 3.49 (1H, s), 3.70 (2H, q, J=9 Hz), 5.20 (1H, s), 6.77 (1H, s), 7.11-7.16 (3H, m), 7.42-7.44 (2H, m), 7.70 (2H, dd, J=9, 5 Hz); MS (ES+) 521 ([MH]+).

Example 12

[6S,9R,11R] 2',3',4',5,5',6,7,8,9,10-Decahydro-2-(5-(4-fluorophenyl)-1H-pyrazol-3-yl)-5'-(2,2,2-trifluoroethyl)-spiro[6,9-methanobenzocyclooctene-11,3'-[1,2,5]thiadiazole] 1',1'-dioxide

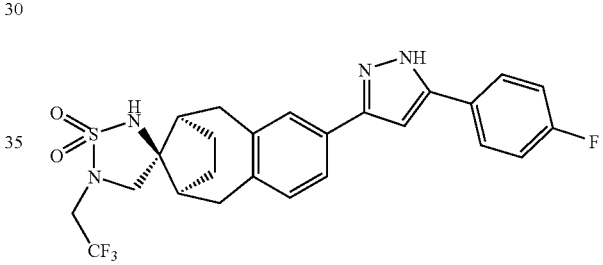

The racemic pyazole from Example 11 was resolved by supercritical fluid chromatographic separation on a Chiralcel OD column using 35% methanol-sc-CO$_2$ as eluant at 35° C., 100 bar, 50 mL/min and UV detection at 250 nm. The first eluted compound under these conditions was the title compound (98% ee).

MS (ES+) 521 ([MH]+).

Example 13

[6S/R,9R/S,11R/S] 2',3',4',5,5',6,7,8,9,10-Decahydro-2-(3-(2-pyridyl)-1H-pyrazol-5-yl)-5'-(2,2,2-trifluoroethyl)-spiro[6,9-methanobenzocyclooctene-11,3'-[1,2,5]thiadiazole] 1',1'-dioxide

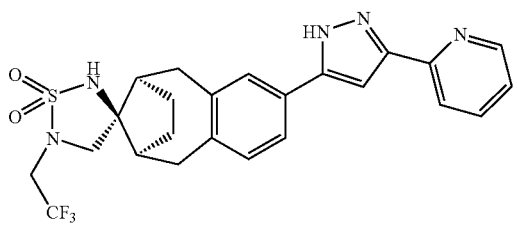

Step 1: [6S/R,9R/S,11R/S] 2',3',4',5,5',6,7,8,9,10-Decahydro-2-(3-(pyrid-2-yl)-propane-1,3-dione)-5'-(2,2,2-trifluoroethyl)-spiro[6,9-methanobenzocyclooctene-11,3'-[1,2,5]thiadiazole] 1',1'-dioxide

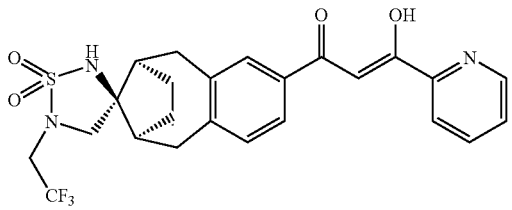

1,1'-Carbonyldiimidazole (51 mg) was added to a solution of Intermediate A (115 mg) in THF (3 mL) and the mixture stirred for 1 h. Meanwhile, lithium bis(trimethylsilyl)amide solution (0.85 mL of a 1M solution in THF) was added to a solution of 2-acetylpyridine (96 µL) in THF (2 mL) at −78° C. After the enolate solution had been stirred for 1 h, to it was added the imidazolide solution (+1 mL washing) via syringe. The mixture was stirred overnight, warming to ambient temperature. The reaction was quenched by addition of satd. $NH_4Cl_{(aq)}$, then diluted with water and ethyl acetate. The layers were separated and the aqueous phase extracted a second time with ethyl acetate. The combined organic extracts were washed with brine, dried ($MgSO_4$) and concentrated. Chromatography on silica eluting with 1 to 2 to 5% methanol in dichloromethane provided the diketone contaminated with 2-acetylpyridine.

Step 2: [6S/R,9R/S,11R/S] 2',3',4',5,5',6,7,8,9,10-Decahydro-2-(3-(2-pyridyl)-1H-pyrazol-5-yl)-5'-(2,2,2-trifluoroethyl)-spiro[6,9-methanobenzocyclooctene-11,3'-[1,2,5]thiadiazole] 1',1'-dioxide

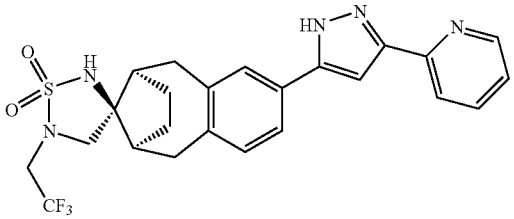

To a suspension of the semi-crude diketone (123 mg) in ethanol (5 mL) was added hydrazine solution (2.4 mL of a 1M solution in THF). The mixture was heated for 4 h at which time thin-layer chromatography indicated incomplete reaction. Further hydrazine solution (2.4 mL of a 1M solution in THF) was added and the mixture heated at reflux for 2 h. The solvent was removed in vacuo and the residue partitioned between water and ethyl acetate. The layers were separated and the organic phase washed sequentially with 10% citric acid solution, water and brine before being dried ($MgSO_4$) and concentrated. Purification by trituration with dichloromethane provided the title compound: δ ($^1$H, 400 MHz, $d_6$-DMSO) 1.09-1.11 (2H, m), 1.70-1.72 (2H, m), 2.38-2.40 (2H, m), 2.59-2.69 (2H, m), 3.18-3.32 (2H, m), 3.48 (2H, s), 3.99-4.06 (2H, m), 7.19 (1H, br d, J=7.8 Hz), 7.26 (1H, br s), 7.34 (1H, br s), 7.56 (1H, br d, J=7.7 Hz), 7.61 (1H, s), 7.88 (2H, br s), 8.03 (1H, s), 8.61 (1H, br s); MS (ES+) 504 ([MH]$^+$).

Example 14

[6S,9R,11R] 2',3',4',5,5',6,7,8,9,10-Decahydro-2-(5-(4-fluorophenyl)-1-methyl-pyrazol-3-yl)-5'-(2,2,2-trifluoroethyl)-spiro[6,9-methanobenzocyclooctene-11,3'-[1,2,5]thiadiazole] 1',1'-dioxide

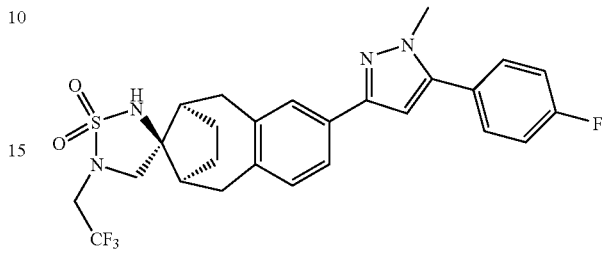

and

Example 15

[6S,9R,11R] 2',3',4',5,5',6,7,8,9,10-Decahydro-2-(3-(4-fluorophenyl)-1-methyl-pyrazol-5-yl)-5'-(2,2,2-trifluoroethyl)-spiro[6,9-methanobenzocyclooctene-11,3'-[1,2,5]thiadiazole] 1',1'-dioxide

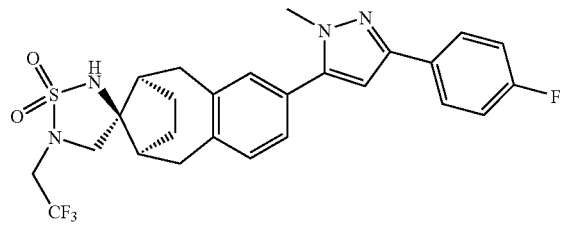

Step 1: [6S,9R,11R] 2',3',4',5,5',6,7,8,9,10-Decahydro-2-acetyl-5'-(2,2,2-trifluorethyl)-spiro[6,9-methanobenzocyclooctene-11,3'-[1,2,5]thiadiazole] 1',1'-dioxide

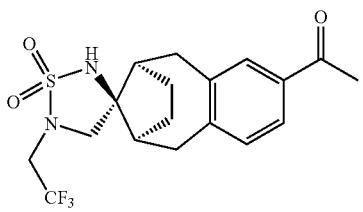

To a de-gassed solution of Intermediate E (0.5 g) in DMF (5 mL) in a tube was added tributyl(1-ethoxyvinyl)tin (0.40 mL) followed by lithium chloride (125 mg), triphenylphosphine (31 mg) and palladium (II) acetate (13 mg). The tube was sealed and heated at 100° C. for 3 h. The cooled mixture was diluted with 1M $HCl_{(aq)}$ (30 mL) and extracted with ethyl acetate (70 mL). The organic extract was dried ($Na_2SO_4$) and concentrated. Chromatography on silica eluting with 20 to 40% ethyl acetate in hexane provided the methyl ketone as a white foam (332 mg, 84% yield). δ ($^1$H, 400 MHz, $CDCl_3$) 1.24-1.31 (2H, m), 1.72-1.76 (2H, m), 2.48-2.50 (2H, m), 2.58 (3H, s), 2.76-2.83 (2H, m), 3.22-3.29 (2H, m), 3.43 (1H, d, J=9.4 Hz), 3.46 (1H, d, J=9.4 Hz), 3.69 (2H, q, J=8.7 Hz), 4.68 (1H, s), 7.19-7.21 (1H, m), 7.70-7.72 (2H, m).

Step 2: [6S,9R,11R] 2',3',4',5,5',6,7,8,9,10-Decahydro-2-(3-[4-fluorophenyl]-3-hydroxy-propan-1-one)-5'-(2,2,2-trifluoroethyl)-spiro[6,9-methanobenzocyclooctene-11,3'-[1,2,5]thiadiazole] 1',1'-dioxide

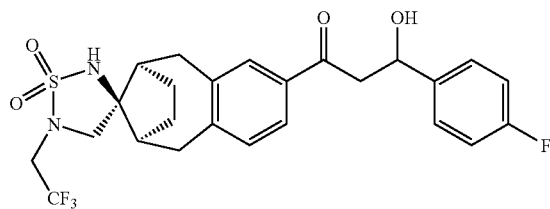

Lithium bis(trimethylsilyl)amide solution (1.7 mL of a 1M solution in THF) was added dropwise to a solution of the ketone from Step 1 (325 mg) in THF (4 mL) at −78° C. After 30 min, 4-fluorobenzaldehyde (0.13 mL) was added dropwise. The reaction mixture was stirred for 2.5 h at −78° C., then quenched by addition of satd. $NH_4Cl_{(aq)}$. The mixture was diluted with water and extracted into ethyl acetate (X2). The combined organic extracts were dried ($MgSO_4$) and concentrated. Chromatography on silica eluting with 10 to 20 to 40% ethyl acetate in hexane afforded the aldol adduct (364 mg, 86% yield) as a white foam. δ ($^1H$, 400 MHz, $CDCl_3$) 1.22-1.27 (2H, m), 1.69-1.74 (2H, m), 2.45-2.50 (2H, m), 2.70-2.78 (2H, m), 3.22-3.32 (4H, m), 3.42 (1H, d, J=9.4 Hz), 3.45 (1H, d, J=9.4 Hz), 3.66-3.72 (3H, m), 5.29-5.33 (2H, m), 7.02-7.07 (2H, m), 7.18 (1H, d, J=7.8 Hz), 7.39-7.42 (2H, m), 7.66-7.69 (2H, m).

Step 3: [6S,9R,11R] 2',3',4',5,5',6,7 8,9,10-Decahydro-2-(3-[4-fluorophenyl]-propenone)-5'-(2,2,2-trifluoroethyl)-spiro[6,9-methanobenzocyclooctene-11,3'-[1,2,5]thiadiazole] 1',1'-dioxide

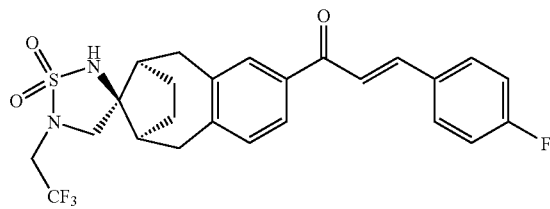

To a solution of the aldol adduct from Step 2 (364 mg) in acetonitrile (10 mL) was added cerium(III) chloride heptahydrate (0.39 g). To the resulting suspension was added sodium iodide (0.16 g) and the reaction mixture was stirred at reflux for 20 h. The mixture was allowed to cool and partitioned between 0.5 M $HCl_{(aq)}$ and ethyl acetate. The layers were separated and the organic phase washed with satd. $NaHCO_{3(aq)}$ (×2) and then brine before being dried ($Na_2SO_4$) and concentrated. Chromatography on silica eluting with 15 to 20 to 30% ethyl acetate in hexane provided the enone (242 mg, 69% yield). δ ($^1H$, 400 MHz, $CDCl_3$) 1.30-1.37 (2H, m), 1.73-1.77 (2H, m), 2.50-2.51 (2H, m), 2.78-2.87 (2H, m), 3.26-3.32 (2H, m), 3.44 (1H, d, J=9.3 Hz), 3.47 (1H, d, J=9.3 Hz), 3.69 (2H, q, J=8.7 Hz), 4.77 (1H, s), 7.10-7.14 (2H, m), 7.24 (1H, d, J=8.0 Hz), 7.45 (1H, d, J=15.7 Hz), 7.63-7.66 (2H, m), 7.76-7.80 (3H, m).

Step 4 [6S,9R,11R] 2',3',4',5,5',6,7,8,9,10-Decahydro-2-(5-(4-fluorophenyl)-1-methyl-pyrazol-3-yl)-5'-(2,2,2-trifluoroethyl)-spiro[6,9-methanobenzocyclooctene-11,3'-[1,2,5]thiadiazole] 1',1'-dioxide

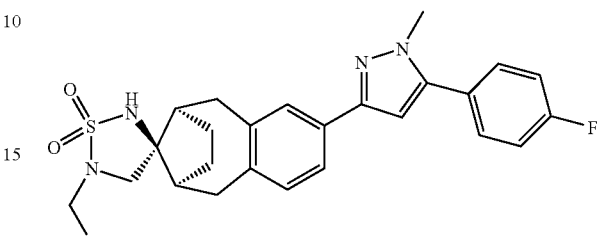

and

[6S,9R,11R] 2',3',4',5,5',6,7,8,9,10-Decahydro-2-(3-(4-fluorophenyl)-1-methyl-pyrazol-5-yl)-5'-(2,2,2-trifluoroethyl)-spiro[6,9-methanobenzocyclooctene-11,3'-[1,2,5]thiadiazole] 1',1'-dioxide

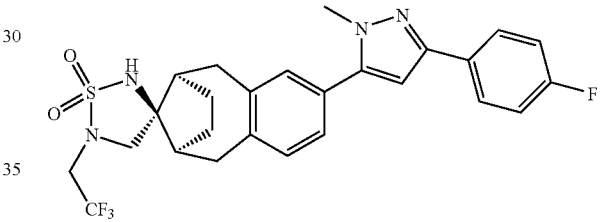

Methyl hydrazine (30 μL) was added to a suspension of the enone from Step 3 (185 mg) in ethanol (15 mL) under nitrogen. The mixture was stirred at room temperature overnight, during which time the material went into solution. The mixture was concentrated in vacuo.

To a solution of the residue in THF (4 mL) was added 2,3-dichloro-5,6-dicyano-1,4-benzoquinone (124 mg) and the resulting suspension was stirred at room temperature for 2 h. The mixture was diluted with ethyl acetate and washed with satd. $NaHCO_{3(aq)}$ (X2) and then brine before being dried ($MgSO_4$) and concentrated. Chromatography on silica afforded a 5:1 mixture of N-Me pyrazole isomers (167 mg, 86% yield). The isomers were separated by preparative HPLC using an acetonitrile/aqueous buffer gradient system.

The first eluted compound, the major isomer, was the title compound Example 14. δ ($^1H$, 400 MHz, $CDCl_3$) 1.33-1.43 (2H, m), 1.69-1.73 (2H, m), 2.46 (2H, br s), 2.69-2.83 (2H, m), 3.19 (1H, d, J=3.7 Hz), 3.25 (1H, d, J=3.7 Hz), 3.44 (2H, s), 3.68 (2H, q, J=8.7 Hz), 3.90 (3H, s), 4.68 (1H, s), 6.56 (1H, s), 7.12-7.20 (3H, m), 7.41-7.45 (2H, m), 7.54 (1H, d, J=8.0 Hz), 7.60 (1H, s); MS (ES+) 535 ([MH]$^+$). The minor regioisomer, Example 15, was isolated by preparative HPLC and was the second eluted compound. δ ($^1H$, 400 MHz, $CDCl_3$) 1.36-1.41 (2H, m), 1.76-1.79 (2H, m), 2.50 (2H, br m), 2.73-2.81 (2H, m), 3.25-3.31 (2H, m), 3.46 (2H, s), 3.70 (2H, q, J=8.7 Hz), 3.92 (3H, s), 4.67 (1H, br s), 6.54 (1H, s), 7.09 (2H, t, J=8.7 Hz), 7.20-7.24 (3H, m), 7.77-7.80 (2H, m); MS (ES+) 535 ([MH]+).

Alternative Route to Example 14

Step 1 5-(4-Fluorophenyl)-1-methyl-1,2-dihydropyrazol-3-one

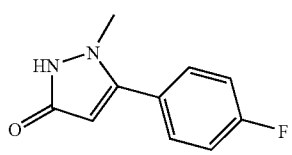

To a solution of methyl 4-(fluorophenyl)propynoate (J. Org. Chem. (1987), 52(16), 3662-8) (13 g, 73 mmol) in methanol (60 ml) was added water (60 ml) followed by methylhydrazine (4 ml, 77 mmol), the mixture was stirred for 6 hrs at 60° C. then left to stand overnight. The solid was filtered and washed with water then a minimum volume of methanol and dried overnight, affording 7.7 g of pure product (55%). δ (¹H, 500 MHz, CDCl₃) 3.68 (3H, s), 5.68 (1H, s), 7.13-7.17 (2H, m), 7.37-7.40 (2H, m).

Step 2 Trifluoromethanesulfonic acid 5-(4-fluorophenyl)-1-methyl-1H-pyrazol-3-yl ester

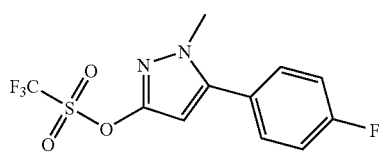

To a cooled suspension of 5-(4-fluorophenyl)-1-methyl-1,2-dihydropyrazol-3-one (15.5 g, 81 mmol) in dry pyridine (1100 ml) was added in three portions trifluoromethanesulfonic anhydride (24 g, 85 mmol) maintaining the temperature below 5° C. After addition the cooling bath was removed and the reaction was stirred for two hours before pouring into 2M hydrochloric acid and extracting into ethyl acetate. The organic layer was washed with brine, saturated sodium hydrogen carbonate, and dried (sodium sulphate), filtered and evaporated to yield a residue which was dissolved in toluene and evaporated and then dissolved in isohexane and filtered through a plug of silica, eluting with dichloromethane. The solvent was evaporated to yield product as a colourless oil (23.4 g, 89%) δ (¹H, 500 MHz, CDCl₃) 3.80 (3H, s), 6.14 (1H, s), 7.15-7.19 (2H, m), 7.38-7.42 (2H, m).

Step 3

The homochiral boronate from Example 24 Step 1 (10.9 g, 22.42 mmol) and the triflate from the above Step 2 (10.9 g, 33.6 mmol) in THF (112 ml) were treated with 33.6 ml of 2M sodium carbonate and LiCl (2.85 g, 66 mmol). The reaction mixture was degassed using a flow of nitrogen, tetrakis(triphenylphosphine)palladium(0) (560 mg, 0.56 mmol) was added, and the reaction was heated to reflux for 16 hours. The reaction was cooled, diluted with ethyl acetate and was washed with water, dried (sodium sulphate), filtered and evaporated. The residue was purified by column chromatography on silica eluting with 25% ethyl acetate/isohexane. The product obtained was crystallized from ethanol and then evaporated from dichloromethane (×3) and dried at 60° C. to yield 6.5 g of product. ¹H nmr and mass spectrometry data as before.

A portion of this product was dissolved in excess diethyl ether. Isohexane was added and the solution was allowed to stand for several hours to form crystals. These were filtered and dried to give a white crystalline solid containing flat rectangular platelike crystals ranging from 2 to 226 micrometers with an average size of ca. 41 micrometers. DSC gave an onset of melting at 185° C. with a peak at 188° C. Found: C, 58.29; H, 4.90; N, 10.48 C₂₆H₂₆F₄N₄O₂S requires C, 58.42; H, 4.90; N, 10.48.

Example 16

[6S/R,9R/S,11R/S] 2',3',4',5,5',6,7,8,9,10-Decahydro-2-(5-(4-fluorophenyl)-thiazol-2-yl)-5'-(2,2,2-trifluoroethyl)-spiro[6,9-methanobenzocyclooctene-11,3'-[1,2,5]thiadiazole] 1',1'-dioxide.

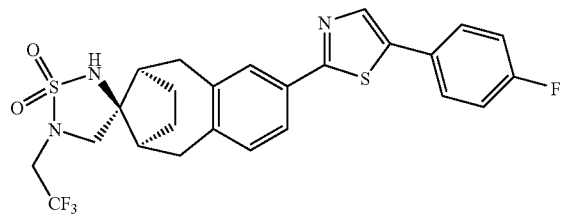

A solution of the ketoamide from Example 6, Step 1 (0.10 g) and Lawesson's reagent (0.15 g) in toluene (3 mL) was refluxed under N₂ for 18 hours. The mixture was cooled, absorbed onto silica gel and evaporated to dryness. Flash column chromatography, eluting with 97:3 dichloromethane—methanol, then preparative thin-layer chromatography, eluting with 98:2 dichloromethane—methanol, gave the thiazole as a pale yellow solid (0.030 g, 30%). δ (¹H, 360 MHz, CDCl₃) 1.32-1.43 (2H, m), 1.68-1.78 (2H, m), 2.45-2.51 (2H, m), 2.73-2.85 (2H, m), 3.24-3.28 (2H, m), 3.45 (2H, s), 3.69 (2H, q, J=9 Hz), 4.66 (1H, s), 7.12 (2H, dd, J=9, 9 Hz), 7.19 (1H, d, J=8 Hz), 7.55-7.59 (2H, m), 7.68 (1H, d, J=8 Hz), 7.74 (1H, s), 7.93 (1H, s); MS (ES+) 538 ([MH]+).

Example 17

(−)-[6S,9R,11R] 2',3',4',5,5',6,7,8,9,10-Decahydro-2-(5-(4-fluorophenyl)-thiazol-2-yl)-5'-(2,2,2-trifluoroethyl)-spiro[6,9-methanobenzocyclooctene-11,3'-[1,2,5]thiadiazole] 1',1'-dioxide

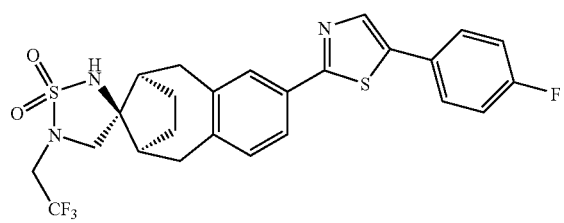

Prepared from the homochiral acid, Intermediate B and 2'-amino-(4-fluoroacetophenone) hydrochloride by the procedures described in Example 6, Step 1 and Example 16. MS (ES+) 538 ([MH]+). [α]_D=−18 (c=0.54, methanol, 23° C.).

Example 18

[6S/R,9R/S,11R/S] 2',3',4',5,5',6,7,8,9,10-Decahydro-2-(5-(1,1-dimethyl-1-ethyl)-thiazol-2-yl)-5'-(2,2,2-trifluoroethyl)-spiro[6,9-methanobenzocyclooctene-11,3'-[1,2,5]thiadiazole] 1',1'-dioxide

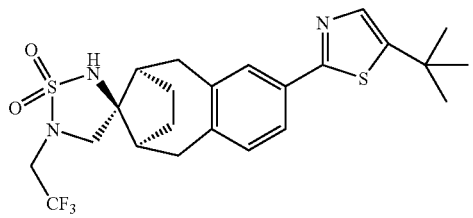

Prepared from the racemic acid, Intermediate A and 1-amino-3,3-dimethyl-2-butanone hydrochloride by the method described for Example 6 Step 1 and Example 16. MS (ES+) 500 ([MH]+).

Example 19

(−)-[6S,9R,11R] 2',3',4',5,5',6,7,8,9,10-Decahydro-2-(5-(2,4-difluorophenyl)-thiazol-2-yl)-5'-(2,2,2-trifluoroethyl)spiro[6,9-methanobenzocyclooctene-11, 3'-[1,2,5]thiadiazole] 1',1'-dioxide.

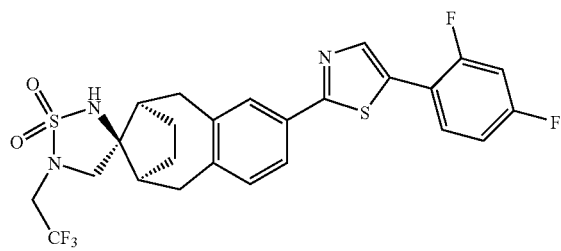

Prepared from 0.2 g of acid, Intermediate B, and 2'-amino-(2,4-difluoroacetophenone) hydrochloride by the method described for Example 6 Step 1 and Example 16 to give the title compound (0.075 g, 28% over 2 steps). MS (ES+) 556 ([MH]+). $\alpha_D$ −15 (c=0.56, DMSO).

Example 20

(−)-[6S,9R,11R] 2',3',4',5,5',6,7,8,9,10-Decahydro-2-(5-(2,4-dichlorophenyl)-thiazol-2-yl)-5'-(2,2,2-trifluoroethyl)spiro[6,9-methanobenzocyclooctene-11, 3'-[1,2,5]thiadiazole] 1',1'-dioxide.

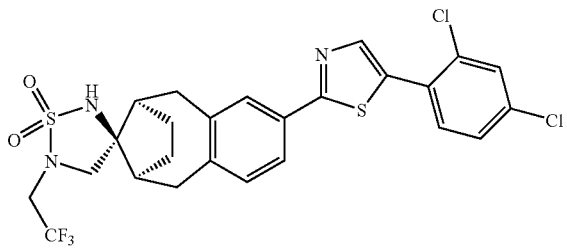

Prepared from 0.2 g of acid, Intermediate B, and 2'-amino-(2,4-dichloroacetophenone) hydrochloride by the method described for Example 6 Step 1 and Example 16 to give the title compound (0.098 g, 34% over 2 steps). MS (ES+) 588, 590, 592 ([MH]+). $\alpha_D$ −19 (c=0.59, DMSO).

Example 21

[6S/R,9R/S,11R/S] 2',3',4',5,5',6,7,8,9,10-Decahydro-2-(5-(piperidin-1-yl)-thiazol-2-yl)-5'-(2,2,2-trifluoroethyl)-spiro[6,9-methanobenzocyclooctene-11, 3'-[1,2,5]thiadiazole] 1',1'-dioxide

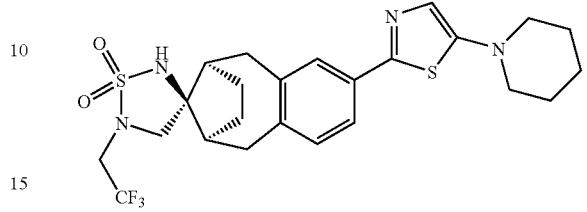

Step 1: [6S/R,9R/S,11R/S] 2',3',4',5,5',6,7,8,9,10-Decahydro-2-(carbonylamino-acetic acid ethyl ester)-5'-(2,2,2-trifluoroethyl)-spiro[6,9-methanobenzocyclooctene-11,3'-[1,2,5]thiadiazole] 1',1'-dioxide

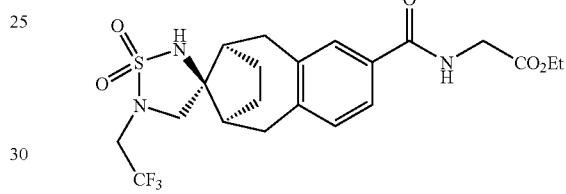

Prepared from the acid Intermediate A and glycine ethyl ester hydrochloride by the method described for Example 6, Step 1. δ (¹H, 360 MHz, CDCl₃) 1.22-1.34 (5H, m), 1.69-1.74 (2H, m), 2.45-2.50 (2H, m), 2.71-2.78 (2H, m), 3.18-3.27 (2H, m), 3.43 (2H, s), 3.68 (2H, q, J=9 Hz), 4.11-4.30 (4H, m), 4.92 (1H, s), 6.66 (1H, t, J=5 Hz), 7.15 (1H, d, J=8 Hz), 7.52-7.55 (2H, m).

Step 2: [6S/R,9R/S,11R/S] 2',3',4',5,5',6,7,8,9,10-Decahydro-2-(carbonylamino-acetic acid)-5'-(2,2,2-trifluoroethyl)-spiro[6,9-methanobenzocyclooctene-11,3'-[1,2,5]thiadiazole] 1',1'-dioxide

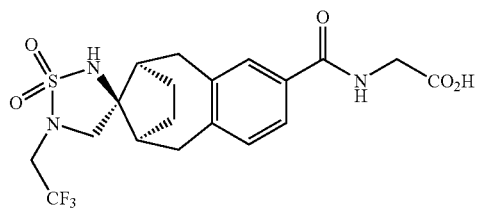

A solution of the ester from Step 1 (0.45 g) and 4M aqueous NaOH (0.75 mL) in THF (4 mL) was stirred at 50° C. under N₂ for 5.5 hours. The mixture was cooled, acidified with 1M hydrochloric acid (20 mL) and extracted with ethyl acetate (20 mL). The extract was dried over Na₂SO₄, filtered and concentrated. Flash column chromatography, eluting with 10% methanol-dichloromethane, then with 0.2% trifluoroacetic acid-10% methanol-dichloromethane, gave the acid as a white powder (0.213 g, 50%). δ (¹H, 360 MHz, DMSO) 0.97-1.09 (2H, m), 1.69-1.72 (2H, m), 2.36-2.40 (2H, m), 2.60-2.70 (2H, m), 3.15-3.22 (2H, m), 3.47 (2H, s), 3.90 (2H, d, J=6 Hz), 3.98-4.06 (2H, m), 7.21 (1H, d, J=8 Hz), 7.55-7.62 (2H, m), 8.03 (1H, s), 8.70 (1H, t, J=6 Hz).

Step 3: [6S/R,9R/S,11R/S] 2',3',4',5,5',6,7,8,9,10-Decahydro-2-(N-[2-oxo-2-piperidin-1-yl-ethyl]carboxamido)-5'-(2,2,2-fluoroethyl)-spiro[6,9-methanobenzocyclooctene-11,3'-[1,2,5]thiadiazole] 1',1'-dioxide

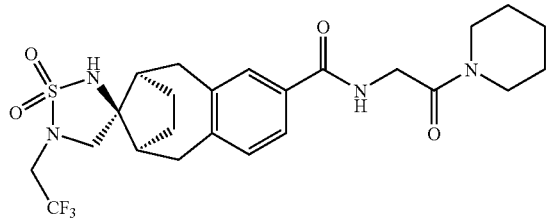

Prepared from the acid, Step 2 and piperidine by the method described for Example 6, Step 1. MS (ES+) 551 ([MNa]+), 529 ([MH]+).

Step 4: [6S/R,9R/S,11R/S] 2',3',4',5,5',6,7,8,9,10-Decahydro-2-(5-(piperidin-1-yl)-thiazol-2-yl)-5'-(2,2,2-trifluoroethyl)-spiro[6,9-methanobenzocyclooctene-11,3'-[1,2,5]thiadiazole] 1',1'-dioxide.

Prepared from the amide, Step 3, by the method described for Example 16. δ ($^1$H, 360 MHz, CDCl$_3$) 1.31-1.41 (2H, m), 1.57-1.62 (2H, m), 1.71-1.77 (6H, m), 2.43-2.48 (2H, m), 2.68-2.80 (2H, m), 3.14-3.24 (6H, m), 3.43 (2H, s), 3.68 (2H, q, J=9 Hz), 3.90 (2H, d, J=6 Hz), 4.67 (1H, s), 6.94 (1H, s), 7.10 (1H, d, J=8 Hz), 7.49 (1H, d, J=8 Hz), 7.58 (1H, s). MS (ES+) 527 ([MH]+).

Example 22

[6S/R,9R/S,11R/S] 2',3',4',5,5',6,7,8,9,10-Decahydro-2-(3-(4-fluorophenyl)-isoxazo-5-yl)-5'-(2,2,2-trifluoroethyl)-spiro[6,9-methanobenzocyclooctene-11,3'-[1,2,5]thiadiazole] 1',1'-dioxide

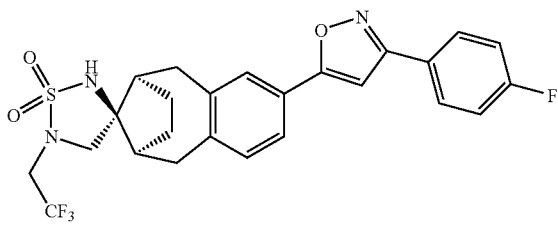

Step 1 [6S/R,9R/S,11R/S] 2',3',4',5,5',6,7,8,9,10-Decahydro-2-(trimethylsilylethynyl)-5'-(2,2,2-trifluoroethyl)-spiro[6,9-methanobenzocyclooctene-11,3'-[1,2,5]thiadiazole] 1',1'-dioxide

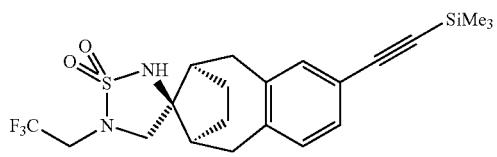

A solution of triflate, Intermediate D, (200 mg, 0.39 mmol), TMS acetylene (112 μL, 0.78 mmol), tetrakis-triphenylphosphine palladium(0) (20 mg, 5 mol %), triphenyl phosphine (10 mg, 10 mol %) and copper iodide (7.6 mg, 10 mol %) was made up in 2 mL of dry piperidine and added to a crimp top microwave vial, the reaction mixture was sealed, purged with nitrogen and then irradiated in the Smith Synthesizer Microwave to 150° C. for 10 minutes. After this time the reaction was diluted with EtOAc (100 mL) and the mixture washed successively with dilute NaHCO$_3$, 1M HCl solution and then saturated brine solution. The organic layer was then separated, dried (MgSO$_4$) and evaporated in vacuo giving a crude residue which was purified by flash column chromatography using 25% EtOAc in isohexane as eluant to give the title compound as a white solid (156 mg, 86% yield). δ ($^1$H, 400 MHz, CDCl$_3$) 0.23 (9H, s), 1.25-1.30 (2H, m), 1.68-1.72 (2H, m), 2.42-2.45 (2H, m), 2.62-2.71 (2H, m), 3.15-3.22 (2H, m), 3.42 (2H, s), 3.67 (2H, q, J=8.7 Hz), 4.68 (1H, brs), 7.03 (1H, d, J=8.2 Hz) and 7.22-7.24 (2H, m).

Step 2 [6S/R,9R/S,11R/S] 2',3',4',5,5',6,7,8,9,10-Decahydro-2-ethynyl-5'-(2,2,2-trifluoroethyl)-spiro[6,9-methanobenzocyclooctene-11,3'-[1,2,5]thiadiazole] 1',1'-dioxide

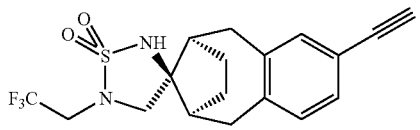

A solution of the TMS acetylene compound from Step 1 (156 mg, 0.34 mmol) in a 10:1 tetrahydrofuran/water mixture (10 mL) was treated with lithium hydroxide (41 mg, 1.71 mmol) and stirred at room temperature for 1.5 hours. After this time the reaction mixture was diluted with 50 mL dichloromethane and washed with saturated brine solution. The organic phase was dried (MgSO$_4$) and evaporated to dryness before purification by flash column chromatography using 20% ethyl acetate in isohexane as eluant to give the title compound as a colourless film (86 mg, 66%). δ ($^1$H, 400 MHz, CDCl$_3$) 1.28-1.32 (2H, m), 1.68-1.72 (2H, m), 2.42-2.46 (2H, m), 2.62-2.71 (2H, m), 3.05 (1H, s), 3.15-3.22 (2H, m), 3.43 (2H, s), 3.67 (2H, q, J=8.7 Hz), 4.66 (1H, brs), 7.03 (1H, d, J=8.2 Hz) and 7.22-7.24 (2H, m).

Step 3 [6S/R,9R/S,11R/S] 2',3',4',5,5',6,7,8,9,10-Decahydro-2-(3-(4-fluorophenyl)-isoxazol-5-yl)-5'-(2,2,2-trifluoroethyl)-spiro[6,9-methanobenzocyclooctene-11,3'-[1,2,5]thiadiazole] 1',1'-dioxide

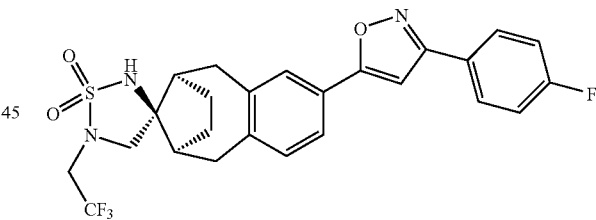

A solution of N-bromosuccinimide (208 mg, 1.17 mmol) in N,N-dimethylformamide (1 mL) was added to a solution of 4-fluorobenzaldoxime (113 mg, 0.26 mmol) in N,N-dimethylformamide (4 mL) at 0° C. and the reaction mixture was stirred, under nitrogen, for 3 hours at 0° C. Triethylamine (163 μL, 117 mmol) was added and the mixture was stirred, under nitrogen, for a further 20 minutes at 0° C. A solution of the acetylene from Step 2 (100 mg, 0.81 mmol) in DMF (1 mL) was added dropwise and the reaction mixture was stirred, under nitrogen, for 1 hour at 0° C. The reaction mixture was diluted with sodium bicarbonate (sat, 50 mL) and extracted with ethyl acetate (2×50 mL). The organics were washed with brine (25 mL), dried (MgSO$_4$) and evaporated in vacuo to give an orange solid. The solid was purified by chromatography on SiO$_2$ eluting with ethyl acetate/hexane (1:9, 1:6, 1:3 and 1:2) to give the title compound (121 mg, 90%) as a cream solid after drying in vacuo (80° C., 2 hours). δ (¹H, 400 MHz, d₄-MeOH: 1.22-1.30 (2H, m), 1.77-1.80 (2H, m), 2.49-2.50 (2H, m), 2.71-2.81 (2H, m), 3.35 (1H, d, J=10 Hz), 3.39 (1H, d, J=10 Hz), 3.52 (2H, s), 3.87 (2H, q, J=9.2 Hz), 7.18 (1H, s), 7.22-7.28 (3H, m), 7.63-7.66 (2H, m) and 7.92-7.96 (2H, m); MS (ES+) 522 ([MH]⁺).

Example 23

[6S/R,9R/S,11R/S]-2',3',4',5,5',6,7,8,9,10-Decahydro-2-(3-(2-pyridyl)-isoxazol-5-yl)-5'-(2,2,2-trifluoroethyl)-spiro[6,9-methanobenzocyclooctene-11,3'-[1,2,5]thiadiazole] 1',1'-dioxide

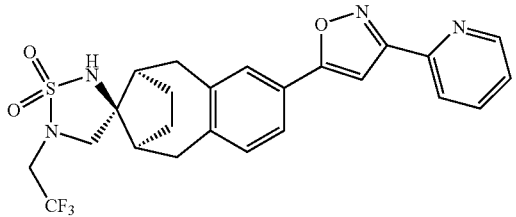

The title compound was prepared in the same way as Example 22 using 2-pyridinealdoxime. MS(ES+) 505 ([MH]⁺).

Example 24

[6S,9R,11R] 2',3',4',5,5',6,7,8,9,10-Decahydro-2-(3-(2-Pyridyl)-isoxazol-5-yl)-5'-(2,2,2-trifluoroethyl)-spiro[6,9-methanobenzocyclooctene-11,3'-[1,2,5]thiadiazole] 1',1'-dioxide

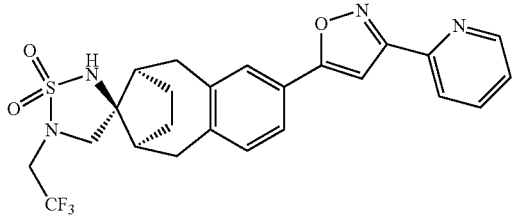

Step 1 [6S,9R,11R] 2',3',4',5,5',6,7,8,9,10-Decahydro-2-(4,4,5,5-tetramethyl-[1,3,2]-dioxaborolan-2-yl)-5'-(2,2,2-trifluoroethyl)spiro[6,9-methanobenzocyclooctene-11,3'-[1,2,5]thiadiazole] 1',1'-dioxide

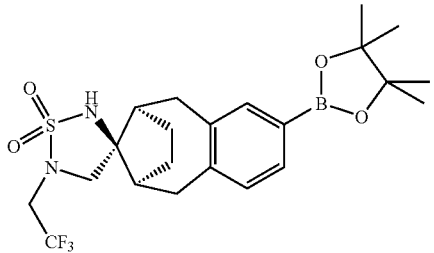

A solution of the homochiral triflate, Intermediate E, (508 mg, 1.0 mmol), bis pinacolatodiboron (279 mg, 1.1 mmol), [1,1'-bis(diphenylphosphino)ferrocene] dichloro palladium (II) dichloromethane complex (82 mg, 0.1 mmol), 1,1'-bis(diphenylphosphino)ferrocene (55 mg, 0.11 mmol) and potassium acetate (294 mg, 3.0 mmol) in dimethylformamide (7 mL) was degassed via a stream of nitrogen before heating at 100° C. for 3 hours. The reaction was cooled to room temperature, diluted with water (30 ml) and extracted with ethylacetate (2×40 mL). The extracts were washed with brine, dried (MgSO₄) and evaporated in vacuo to give a black oil, which was purified by column chromatography, eluting with ethyl acetate:iso-hexane (1:5) to give the title compound as a white solid (480 mg, 99%). δ (¹H, 400 MHz, CDCl₃) 1.30-1.34 (14H, m), 1.65-1.75 (2H, m), 2.40-2.50 (2H, m), 2.69-2.80 (2H, m), 3.14-3.25 (2H, m), 3.40-3.45 (2H, m), 3.65-3.71 (2H, m), 4.66 (1H, brs), 7.10 (1H, d, J=7.4 Hz), 7.53 (1H, s) and 7.56 (1H, d, J=7.4 Hz).

Step 2 [6S,9R,11R] 2',3',4',5,5',6,7,8,9,10-Decahydro-2-(3-(2-pyridyl)-isoxazol-5-yl)-5'-(2,2,2-trifluoroethyl)-spiro[6,9-methanobenzocyclooctene-11,3'-[1,2,5]thiadiazole] 1',1'-dioxide

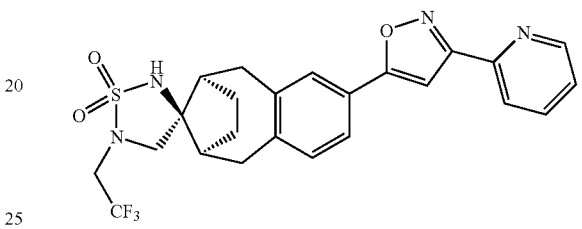

A mixture of 2-(5-iodoisoxazol-3-yl)pyridine (prepared in the manner of Ku et al Org. Lett. 3 (26), 4185-4187, 2001.) (90 mg, 0.3 mmol), the homochiral boronate from Step 1 (100 mg, 0.2 mmol) potassium carbonate (135 mg, 1 mmol) and [1,1'-bis(diphenylphosphino)ferrocene] dichloro palladium (II) dichloromethane complex (5 mg) in toluene (2 mL), ethanol (1 mL) and water (1 mL) was heated under microwave conditions at 100° C. for 5 minutes. More [1,1'-bis(diphenylphosphino)ferrocene] dichloro palladium (II) dichloromethane complex (5 mg) was added and the mixture was again heated under microwave conditions at 100° C. for 5 minutes. The reaction was diluted with sodium bicarbonate (half sat, 20 mL) and extracted with ethylacetate (2×30 mL). The extracts were washed with brine, dried (MgSO₄) and evaporated in vacuo to give a brown gum, which was purified by column chromatography, eluting with ethylacetate:iso-hexane (1:4) to give the title compound as a white solid (70 mg, 69%). δ (¹H, 400 MHz, CDCl₃) 1.32-1.40 (2H, m), 1.74-1.78 (2H, m), 2.48-2.52 (2H, m), 2.74-2.83 (2H, m), 3.26-3.31 (2H, m), 3.46 (2H, s), 3.70 (2H, q, J=8.7 Hz), 4.83 (1H, brs), 7.17 (1H, s), 7.23 (1H, d, J=8.3 Hz), 7.36-7.40 (1H, m), 7.60-7.62 (2H, m), 7.81-7.85 (1H, m), 8.12-8.14 (1H, m), and 8.71-8.72 (1H, m). MS (ES+) 505 ([MH]⁺).

Example 25

[6S/R,9R/S,11R/S] 2',3',4',5,5',6,7,8,9,10-Decahydro-2-(3-(2,4-dichlorophenyl)-isoxazol-5-yl)-5'-(2,2,2-trifluoroethyl)-spiro[6,9-methanobenzocyclooctene-11,3'-[1,2,5]thiadiazole] 1',1'-dioxide

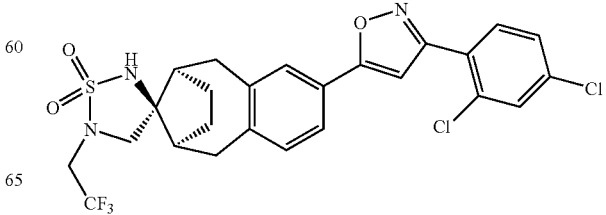

The title compound was prepared from Intermediate D using the method described in Example 22 and with 2,4-dichlorobenzaldehyde oxime. MS (ES+) 572, 574, 575 ([MH]+).

Example 26

[6S,9R,11R] 2',3',4',5,5',6,7,8,9,10-Decahydro-2-(4-(4-fluorophenyl)-1H-imidazol-2-yl)-5'-(2,2,2-trifluoroethyl)-spiro[6,9-methanobenzocyclooctene-11,3'-[1,2,5]thiadiazole] 1',1'-dioxide

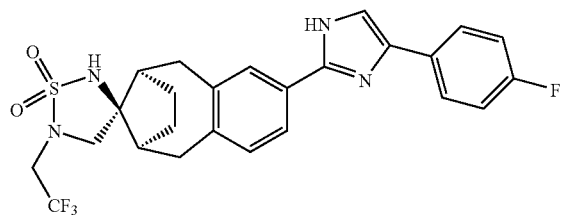

Step 1: 1-(Dimethylaminosulfonyl)-4-bromoimidazole

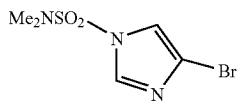

Sodium hydride (55% in oil, 0.31 g) was added to a stirred solution of 4-bromo-1H imidazole (1.02 g) in dry tetrahydrofuran (20 mL) at room temperature under N₂. After 10 minutes, dimethylsulfamoyl chloride (0.81 mL) was added. After stirring for 5 hours, the mixture was diluted with saturated aqueous ammonium chloride (20 mL) and extracted with ethyl acetate (20 mL). The extract was dried over Na₂SO₄, filtered and concentrated. The white solid was rinsed with diethyl ether and dried to give 1-(dimethylaminosulfonyl)-4-bromoimidazole (1.53 g, 87%). MS (ES+) 256, 254 ([MH]+).

Step 2: 1-(Dimethylaminosulfonyl)-4-(4-fluorophenyl)imidazole

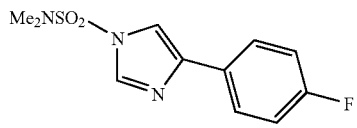

A mixture of the bromide from Step 1 (0.543 g), 4-fluorophenylboronic acid (0.31 g), tetrakis(triphenylphosphine) palladium (0) (0.2 g), 2M aqueous sodium carbonate (2.2 mL) and toluene (10 mL) was refluxed under N₂ for 1.5 hours. The mixture was cooled, poured into water (75 mL) and extracted with ethyl actetate (2×25 mL). The extracts were dried over Na₂SO₄, filtered and concentrated. Flash column chromatography, eluting with 40% ethyl acetate-isohexane, gave 1-(dimethylaminosulfonyl)-4-(4-fluorophenyl)imidazole (0.417 g, 72%) as a yellow solid. MS (ES+) 270 ([MH]+).

Step 3: 1-(Dimethylaminosulfonyl)-2-bromo-4-(4-fluorophenyl)imidazole

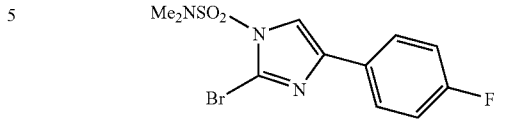

A solution of n-butyllithium (1.6M, 0.35 mL) was added dropwise at −78° C. to a stirred solution of the imidazole from Step 2 (0.20 g) in dry tetrahydrofuran (4 mL) under N₂. After 7 hours, 1,2-dibromotetrafluoroethane (0.12 mL) was added and the mixture was stirred for 18 hours, warming to room temperature. The solution was evaporated onto silica gel and flash column chromatography, eluting with 20% ethyl acetate-isohexane, gave the bromide (0.152 g, 59%) as a yellow oil. MS (ES+) 348, 350 ([MH]+).

Step 4: [6S,9R,11R] 2',3',4',5,5',6,7,8,9,10-Decahydro-2-[1-(dimethylaminosulfonyl)-4-(4-fluorophenyl)-imadazol-2-yl]-5'-(2,2,2-trifluoroethyl)-spiro[6,9-methanobenzocyclooctene-11,3'-[1,2,5]thiadiazole] 1',1'-dioxide.

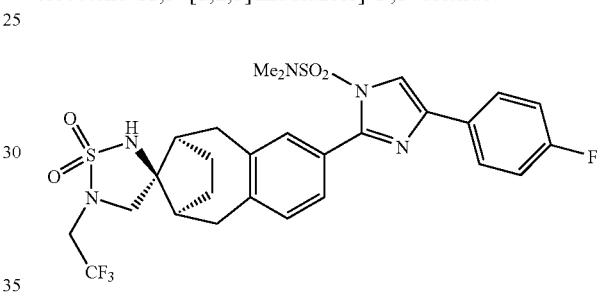

A mixture of the bromide from Step 3 (0.075 g), the homochiral boronate ester from Example 24, Step 1 (0.105 g), tetrakis(triphenylphosphine) palladium (0) (0.1 g), 2M aqueous sodium carbonate (0.22 mL) and toluene (3 mL) was refluxed for 4 hours. The mixture was cooled, diluted with ethyl acetate (15 mL) and washed with water (10 ml). The organic phase was filtered through a Teflon membrane and concentrated. Flash column chromatography, eluting with 20% then 30% then 50% ethyl acetate-isohexane, gave the product as a yellow oil (0.085 g, 63%). MS (ES+) 628 ([MH]+).

Step 5: [6S,9R,11R] 2',3',4',5,5',6,7,8,9,10-Decahydro-2-(4-(4-fluorophenyl)-1H-imadazol-2-yl)-5'-(2,2,2-trifluoroethyl)-spiro[6,9-methanobenzocyclooctene-11,3'-[1,2,5]thiadiazole] 1',1'-dioxide.

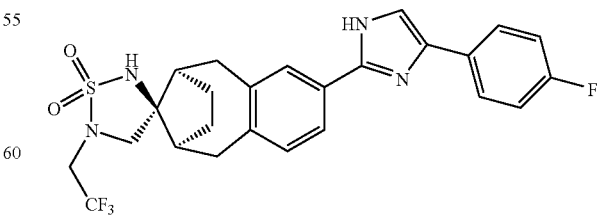

A solution of the product from Step 4 (0.085 g) and 2M hydrochloric acid (1 mL) in tetrahydrofuran (5 mL) was refluxed under N₂ for 1 hour. The solution was cooled, poured into saturated aqueous sodium hydrogen carbonate (30 mL) and extracted with ethyl acetate (2×30 ml). The extracts were dried over Na$_2$SO$_4$, filtered and concentrated. Flash column chromatography, eluting with 50% ethyl acetate-isohexane, then preparative thin layer chromatography, eluting with 50% ethyl acetate-isohexane, gave the imidazole as a waxy solid (0.014 g, 20%). δ ($^1$H, 360 MHz, CDCl$_3$) 1.21-1.25 (2H, m), 1.60-1.70 (2H, m), 2.30-2.40 (2H, m), 2.55-2.66 (2H, m), 3.05-3.14 (2H, m), 3.39 (2H, s), 3.68 (2H, q, J=9 Hz), 5.12 (1H, s), 7.04-7.09 (3H, m), 7.30 (1H, s), 7.54 (1H, d, J=8 Hz), 7.61 (1H, s), 7.69-7.77 (2H, m). MS (ES+) 521 ([MH]$^+$).

Example 27

[6S/R,9R/S,11R/S] 2',3',4',5,5',6,7,8,9,10-Decahydro-2-(4-(4-fluorophenyl)-1,2,3-triazol-1-yl)-5'-(2,2,2-trifluoroethyl)spiro[6,9-methanobenzocyclooctene-11,3'-[1,2,5]thiadiazole] 1',1'-dioxide.

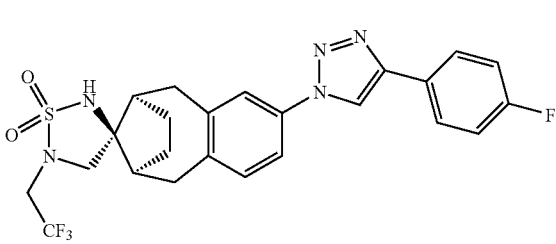

Intermediate C (0.5 g, 1.33 mmol) was suspended in concentrated HCl (10 mL) and water (10 mL) and cooled in an ice-salt bath. A solution of sodium nitrite (0.092 g, 1.33 mmol) in water (5 mL) was added dropwise, maintaining the internal temperature below 0° C. The orange solution was stirred at a temperature below 0° C. for 20 mins. This diazonium salt solution was added dropwise to a solution of sodium azide (0.087 g, 1.33 mmol) and acetic acid sodium salt (1.09 g, 13.3 mmol) in water (10 mL) at room temperature. Nitrogen evolution was observed. The reaction was stirred at room temperature for 18 hours. The pale green solid was collected by filtration, washed well with water and dried at room temperature. Purification by flash column chromatography on silica, eluting with 25% ethyl acetate—isohexane gave the azide (0.27 g, 51%). 0.26 g (0.65 mmol) of this and 1-ethynyl-4-fluorobenzene (0.078 g, 0.65 mmol) in xylene (10 mL) were heated under reflux for 18 hours. Another 0.078 g of 1-ethynyl-4-fluorobenzene was added and heating continued for 7 hours. Another 0.078 g of 1-ethynyl-4-fluorobenzene was added and heating continued for 18 hours. The solvent was removed in vacuo. The residue was purified by flash column chromatography on silica, eluting with 25% ethyl acetate—isohexane, followed by trituration in dichloromethane to give the title compound (0.016 g, 5%). Λ ($^1$H, 400 MHz, CDCl$_3$) 1.33-1.43 (2H, m), 1.75-1.82 (2H, m), 2.50-2.54 (2H, m), 2.77-2.85 (2H, m), 3.27-3.35 (2H, m), 3.46 (2H, s), 3.70 (2H, q, J=8.7 Hz), 4.66 (1H, s), 7.14-7.18 (2H, m), 7.26-7.29 (1H, m), 7.52 (1H, dd, J=2.2, 8 Hz), 7.58 (1H, d, J=2 Hz), 7.86-7.90 (2H, m), 8.12 (1H, s).

MS (ES+) 522 ([MH]$^+$).

Example 28

[6S,9R,11R] 2',3',4',5,5',6,7,8,9,10-Decahydro-2-(5-(piperidin-1-yl)-thiazol-2-yl)-5'-(2,2,2-trifloroethyl)-spiro[6,9-methanobenzocyclooctene-11,3'-[1,2,5]thiadiazole] 1',1'-dioxide

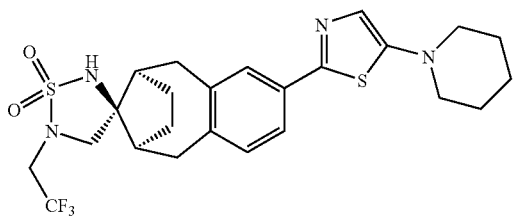

Prepared from the homochiral acid Intermediate B by the method described for Example 21. MS (ES+) 527 ([MH]$^+$). [α]$_D$=−25 (c=0.526, DMSO)

Example 29

[6S,9R,11R] 2',3',4',5,5',6,7,8,9,10-Decahydro-2-(5-(morpholin-4-yl)-thiazol-2-yl)-5'-(2,2,2-trifluoroethyl)-spiro[6,9-methanobenzocyclooctene-11,3'-[1,2,5]thiadiazole] 1',1'-dioxide

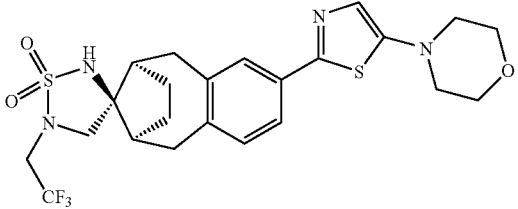

Prepared from the homochiral acid Intermediate B and morpholine by the method described for Example 21. MS (ES+) 529 ([MH]$^+$).

Example 30

[6S,9R,11R] 2',3',4',5,5',6,7,8,9,10-Decahydro-2-(5-(4-trifluoromethyl-piperidin-1-yl)-thiazol-2-yl)-5'-(2,2,2-trifluoroethyl)-spiro[6,9-methanobenzocyclooctene-11,3'-[1,2,5]thiadiazole] 1',1'-dioxide

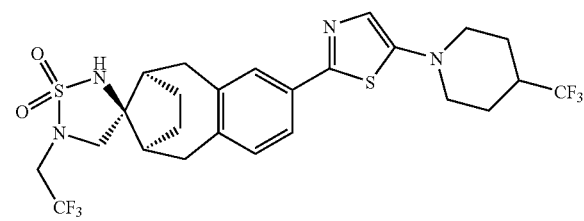

Prepared from the homochiral acid Intermediate B and 4-trifluoromethylpiperidine by the method described for Example 21. MS (ES+) 595 ([MH]$^+$).

Example 31

[6S,9R,11R] 2',3',4',5,5',6,7,8,9,10-Decahydro-2-(5-(4,4-difluoropiperidin-1-yl)-thiazol-2-yl)-5'-(2,2,2-trifluoroethyl)-spiro[6,9-methanobenzocyclooctene-11,3'-[1,2,5]thiadiazole] 1',1'-dioxide

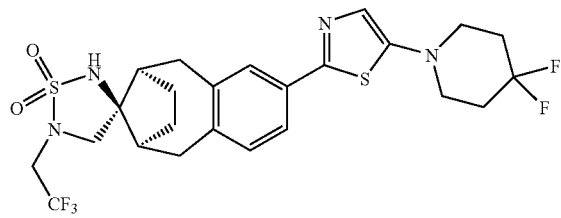

Prepared from the homochiral acid Intermediate B and 4,4-difluoropiperidine by the method described for Example 21. MS (ES+) 563 ([MH]+).

Example 32

[6S,9R,11R] 2',3',4',5,5',6,7,8,9,10-Decahydro-2-(5-(3,3-difluoroazetidin-1-yl)-thiazol-2-yl)-5'-(2,2,2-trifluoroethyl)-spiro[6,9-methanobenzocyclooctene-11,3'-[1,2,5]thiadiazole] 1',1'-dioxide

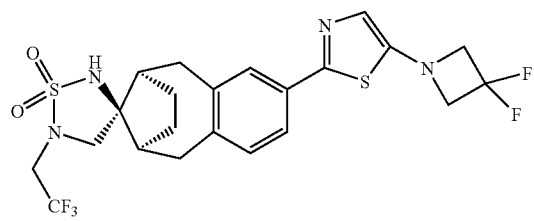

Prepared from the homochiral acid Intermediate B and 3,3-difluoroazetidine hydrochloride by the method described for Example 21. MS (ES+) 535 ([H]+).

Example 33

[6S,9R,11R] 2',3',4',5,5',6,7,8,9,1-Decahydro-2-(5-(3,3-difluoropiperidin-1-yl)-thiazol-2-yl)-5'-(2,2,2-trifluoroethyl)-spiro[6,9-methanobenzocyclooctene-11,3'-[1,2,5]thiadiazole] 1',1'-dioxide.

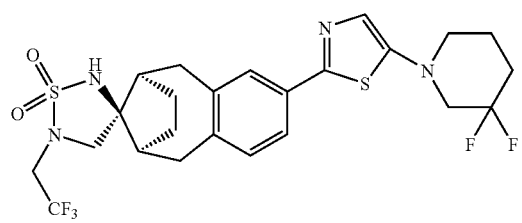

Prepared from the homochiral acid Intermediate B and 3,3-difluoropiperidine hydrochloride by the method described for Example 21: MS (ES+) 563 ([MH]+).

Example 34

[6S,9R,11R] 2',3',4',5,5',6,7,8,9,10-Decahydro-2-(5-(dimethylamino)-thiazol-2-yl)-5'-(2,2,2-trifluoroethyl)-spiro[6,9-methanobenzocyclooctene-11,3'-[1,2,5]thiadiazole] 1',1'-dioxide

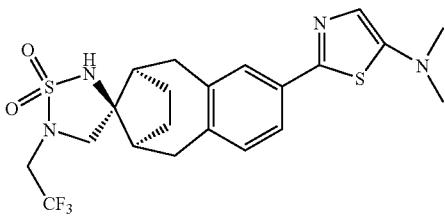

Prepared from the homochiral acid Intermediate B and dimethylamine hydrochloride by the method described for Example 21. MS (ES+) 563 ([MH]+).

Example 35

(−)-[6S,9R,11R] 2',3',4',5,5',6,7,8,9,10-Decahydro-2-(5-(2-chlorophenyl)-thiazol-2-yl)-5'-(2,2,2-trifluoroethyl)-spiro[6,9-methanobenzocyclooctene-11,3'-[1,2,5]thiadiazole] 1',1'-dioxide

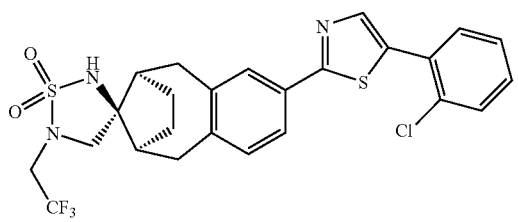

Prepared from the acid, Intermediate B, and 2'-amino-(2-chloroacetophenone) hydrochloride by the method described for Example 6 Step 1 and Example 16 to give the title compound. MS (ES+) 554, 556 ([MH]+). $\alpha_D$ −18 (c=0.55, DMSO).

Example 36

[6S/R,9R/S,11R/S] 2',3',4',5,5',6,7,8,9,10-Decahydro-2-(5-(3-fluorophenyl)-thiazol-2-yl)-5'-(2,2,2-trifluoroethyl)-spiro[6,9-methanobenzocyclooctene-11,3'-[1,2,5]thiadiazole] 1',1'-dioxide

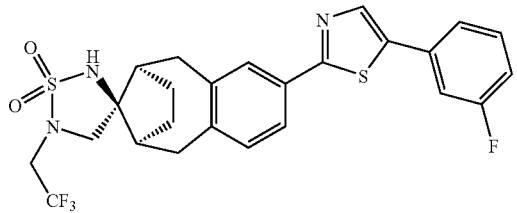

Step 1: [6S/R,9R/S,11R/S] 2',3',4',5,5',6,7,8,9,10-Decahydro-2-(thiazol-2-yl)-5'-(2,2,2-trifluoroethyl)-spiro[6,9-methanobenzocyclooctene-11,3'-[1,2,5]thiadiazole] 1',1'-dioxide

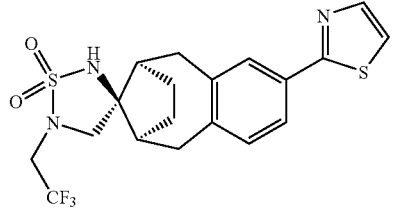

[6S/R,9R/S,11R/S] 2',3',4',5,5',6,7,8,9,10-Decahydro-2-(4,4,5,5-tetramethyl-[1,3,2]-dioxaborolan-2-yl)-5'-(2,2,2-trifluoroethyl)spiro[6,9-methanobenzocyclooctene-11,3'-[1,2,5]thiadiazole] 1',1'-dioxide was synthesised from the triflate Intermediate D using the method described in Example 24, Step 1. Three portions of 100 mg of the aforementioned boronate were weighed into separate microwave reaction tubes. To each tube were added toluene (2 mL), ethanol (1 mL), water (1 mL), 2-bromothiazole (28 μL), potassium carbonate (142 mg) and [1,1'bis(diphenylphosphino)ferrocene] dichloro palladium(II), complex with dichloromethane (17 mg). The reaction tubes were sealed and the mixtures heated in a microwave at 100° C. for 5 min. Thin-layer chromatographic analysis indicated incomplete reaction, therefore a spatula tipful of the palladium catalyst was added to each reaction mixture before re-sealing and heating for a further 5 min at 100° C. The reaction mixtures were combined, poured into satd. NaHCO$_3$(aq) and extracted with ethyl acetate. The organic layer was washed with brine, dried over Na$_2$SO$_4$ and concentrated to give a brown gum. Chromatography on silica eluting with 25% ethyl acetate in hexane gave the title compound (200 mg, 72% yield). δ ($^1$H, 400 MHz, CDCl$_3$) 1.33-1.39 (2H, m), 1.71-1.76 (2H, m), 2.46-2.50 (2H, m), 2.72-2.84 (2H, m), 3.23-3.28 (2H, s), 3.69 (2H, q, J=8.7 Hz), 4.78 (1H, s), 7.17 (1H, d, J=7.8 Hz), 7.32 (1H, d, J=3 Hz), 7.69 (1H, dd, J=7.8, 1.7 Hz), 7.74 (1H, s), 7.85 (1H, d, J=3 Hz); MS (ES+) 444 ([MH]$^+$).

Step 2: [6S/R,9R/S,11R/S] 2',3',4',5,5',6,7,8,9,10-Decahydro-2-(5-bromothiazol-2-yl)-5'-(2,2,2-trifluoroethyl)-spiro[6,9-methanobenzocyclooctene-11,3'-[1,2,5]thiadiazole] 1',1'-dioxide

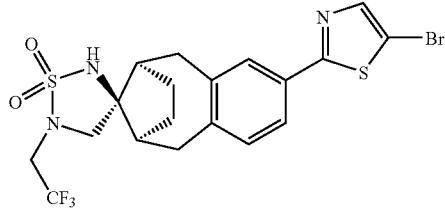

To the thiazole from Step 1 (400 mg) was added acetic acid (5 mL) followed by bromine (46 μL). The reaction mixture was stirred at room temperature overnight. Cold water was added and the precipitate was collected by filtration, washing with water. The solid was dissolved in ethyl acetate, washed with 10% Na$_2$CO$_3$ solution$_{(aq)}$ and then brine before being dried over Na$_2$SO$_4$ and concentrated. Chromatography on silica eluting with 25% ethyl acetate in hexane provided the title compound (240 mg, 51% yield) together with recovered starting material (33%). δ ($^1$H, 400 MHz, CDCl$_3$) 1.33-1.37 (2H, m), 1.72-1.76 (2H, m), 2.47-2.50 (2H, m), 2.72-2.82 (2H, m), 3.23-3.27 (2H, m), 3.44 (2H, s), 3.69 (2H, q, J=8.7 Hz), 4.77 (1H, s), 7.17 (1H, d, J=7.8 Hz), 7.58 (1H, dd, J=7.8, 1.6 Hz), 7.63 (1H, d, J=1.6 Hz), 7.72 (1H, s); MS (ES+) 522, 524 ([MH]$^+$).

Step 3: [6S/R,9R/S,11R/S] 2',3',4',5,5',6,7,8,9,10-Decahydro-2-(5-(3-fluorophenyl)-thiazol-2yl)-5'-(2,2,2-trifluoroethyl)-spiro[6,9-methanobenzocyclooctene-11,3'-[1,2,5]thiadiazole] 1',1'-dioxide

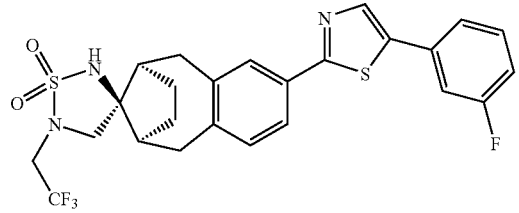

To a solution of the bromide from Step 2 (20 mg) in toluene (0.5 mL), ethanol (0.25 mL) and water (0.25 mL) were added 3-fluorophenylboronic acid (8 mg), potassium carbonate (26 mg) and [1,1'bis(diphenylphosphino)ferrocene] dichloro palladium(II), complex with dichloromethane (3 mg). The mixture was heated in a microwave at 100° C. for 5 min. Additional catalyst was added and the mixture was heated at 100° C. for a further 10 min. The reaction mixture was poured into satd. NaHCO$_{3(aq)}$ and extracted with ethyl acetate (X2). The combined organic extracts were washed with brine, dried over Na$_2$SO$_4$ and concentrated. Chromatography on silica eluting with 25% ethyl acetate in hexane gave the title compound (5.5 mg, 27%). δ ($^1$H, 400 MHz, CDCl$_3$) 1.31-1.41 (2H, m), 1.71-1.77 (2H, m), 2.47-2.51 (2H, m), 2.72-2.84 (2H, m), 3.25-3.29 (2H, m), 3.45 (2H, s), 3.70 (2H, q, J=8.7 Hz), 4.93 (1H, s), 7.01-7.06 (1H, m), 7.18 (1H, d, J=7.8 Hz), 7.28-7.31 (1H, m), 7.37-7.41 (2H, m), 7.68 (1H, dd, J=7.8, 1.6 Hz), 7.73 (1H, d, J=1.2 Hz), 8.00 (1H, s); MS (ES+) 538 ([MH]$^+$).

Example 37

[6S,9R,11R] 2',3',4',5,5',6,7,8,9,10-Decahydro-2-(3-(3-pyridyl)-isoxazol-5-yl)-5'-(2,2,2-trifluoroethyl)-spiro[6,9-methanobenzocyclooctene-11,3'-[1,2,5]thiadiazole] 1',1'-dioxide

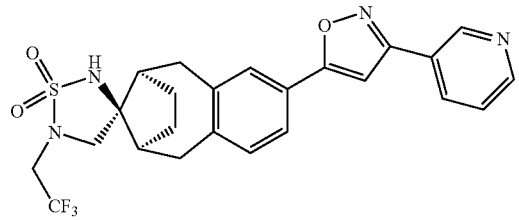

Step 1: α-Chloro-3-pyridinealdoxime hydrochloride

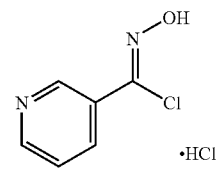

Chlorine gas was bubbled through a cold (0° C.) suspension of pyridine-3-aldoxime (5.0 g, 40.9 mmol) in dichloromethane (150 mL) until the solution was saturated. The reaction vessel was stoppered and stirred, whilst allowed to warm to room temperature, for 16 hours. The excess chlorine was blown off by a stream of nitrogen and the solids collected by filtration, washed with dichloromethane and dried in vacuo to give the chloro-oxime hydrochloride as a white solid (7.5 g, 94%). δ ($^1$H, 400 MHz, d$_6$-DMSO) 7.69 (1H, dd, J=8.4 & 5.3 Hz), 8.31-8.34 (1H, m), 8.76 (1H, dd, J=4.9 & 1.4 Hz), 9.02 (1H, d, J=0.5 Hz) and 12.86 (1H, s). MS (ES+) 157 ([MH]$^+$).

Step 2: [6S,9R,11R] 2',3',4',5,5',6,7 8,9,10-Decahydro-2-(3-(3-pyridyl)-isoxazol-5-yl)-5'-(2,2,2-trifluoroethyl)-spiro[6,9-methanobenzocyclooctene-11,3'-[1,2,5]thiadiazole] 1',1'-dioxide

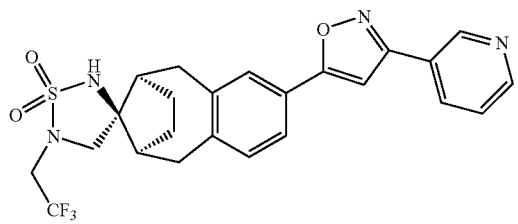

[6S,9R,11R] 2',3',4',5,5',6,7,8,9,10-Decahydro-2-ethynyl-5'-(2,2,2-trifluoroethyl)-spiro[6,9-methanobenzocyclooctene-11,3'-[1,2,5]thiadiazole] 1',1'-dioxide was synthesised from the homochiral triflate Intermediate E using the method described in Example 22, Steps 1 and 2. Triethylamine (78 uL, 056 mmol) was added dropwise to a mixture of the aforementioned acetylene (54 mg, 0.14 mmol) and the chloro-oxime from Step 1 (54 mg, 0.28 mmol) in dichloromethane (10 mL) and the reaction was stirred at room temperature for 65 hours. The reaction was diluted with sodium bicarbonate (sat, 25 mL) and extracted with dichloromethane. The extracts were washed with water, dried (MgSO$_4$) and evaporated in vacuo to give a yellow solid, which was purified by column chromatography, eluting with ethyl acetate:iso-hexane (2:1) to give the title compound as a white solid (38 mg, 54%). δ ($^1$H, 400 MHz, d$_6$-DMSO) 1.04-1.09 (2H, m), 1.72-1.75 (2H, m), 2.39-2.44 (2H, m), 2.68-2.75 (2H, m), 3.21-3.29 (2H, m), 3.43 (2H, s), 4.03 (2H, q, J=9.6 Hz), 7.34 (1H, d, J=7.8 Hz), 7.63-7.69 (4H, m), 8.07 (1H, s), 8.41-8.45 (1H, m), 8.79 (1H, s), 9.17 (1H, s). MS (ES+) 505 ([MH]$^+$).

Example 38

[6S,9R,11R] 2',3',4',5,5',6,7,8,9,10-Decahydro-2-(3-(4-Pyridyl)-isoxazol-5-yl)-5'-(2,2,2-trifluoroethyl)-spiro[6,9-methanobenzocyclooctene-11,3'-[1,2,5]thiadiazole] 1',1'-dioxide

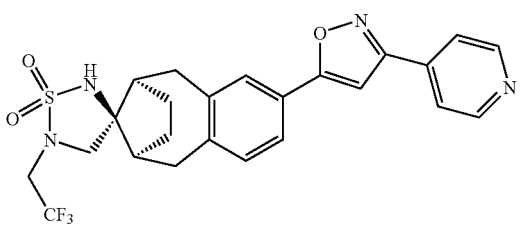

Prepared by the method described in Example 37, using pyridine-4-aldoxime. MS (ES+) 505 ([MH]$^+$).

Example 39

[6S/R,9R/S,11R/S] 2',3',4',5,5',6,7,8,9,10-Decahydro-2-(5-(1-tert-butoxycarbonyl-1,2,3,6-tetrahydropyridin-4-yl)-thiazol-2-yl)-5'-(2,2,2-trifluoroethyl)-spiro[6,9-methanobenzocyclooctene-11,3'-[1,2,5]thiadiazole] 1',1'-dioxide

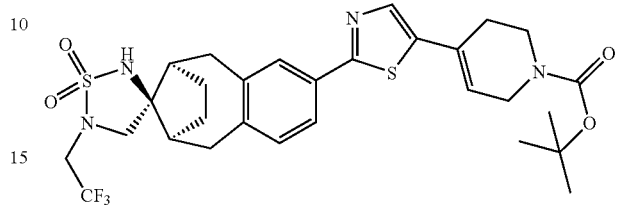

Step 1: 1-tert-Butoxycarbonyl-4-trifluoromethanesulphonyloxy-1,2,3,6-tetrahydropyridine

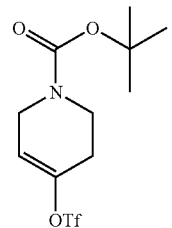

Prepared using the procedure described in Synthesis 1991, 993.

Step 2: 1-tert-Butoxycarbonyl-4-(4,4,5,5-tetramethyl-[1,3,2]-dioxaborolanyl)-1,2,3,6-tetrahydropyridine

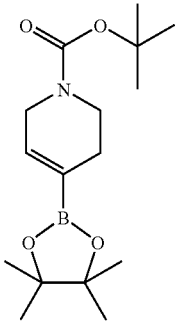

Prepared from the triflate from Step 1 by the method described for Example 24, Step 1.

Step 3: [6S/R,9R/S,11R/S] 2',3',4',5,5',6,7,8,9,10-Decahydro-2-(5-(1-tert-Butoxycarbonyl-1,2,3,6-tetrahydropyridin-4-yl)-thiazol-2-yl)-5'-(2,2,2-trifluoroethyl)-spiro[6,9-methanobenzocyclooctene-11,3'-[1,2,5]thiadiazole] 1',1'-dioxide

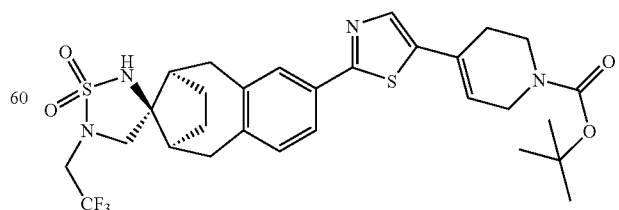

Prepared from the boronate from Step 2 and the bromide from Example 36, Step 2 by the method described for Example 36, Step 3. Contains ~10% unsubstituted thiazole. MS (ES+) 444, 625 ([MH]+).

Example 40

[6S/R,9R/S,11R/S] 2',3',4',5,5',6,7,8,9,10-Decahydro-2-(5-(1,2,3,6-tetrahydro-1H-pyridin-4-yl)-thiazol-2-yl)-5'-(2,2,2-trifluoroethyl)-spiro[6,9-methanobenzocyclooctene-11,3'-[1,2,5]thiadiazole] 1',1'-dioxide

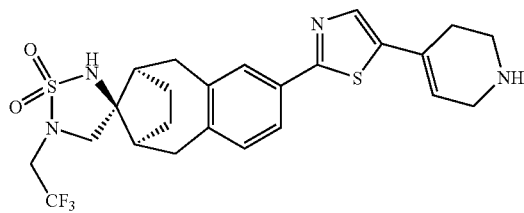

A solution of the 1-tert-butoxycarbonyl-1,2,3,6-tetrahydropyridine from Example 39 Step 3 (0.11 g, 0.18 mmol) and trifluoroacetic acid (1 mL) in dichloromethane (1 mL) was stirred at room temperature for 90 minutes. The reaction was diluted with ethyl acetate (25 mL), washed with 10% aqueous sodium carbonate (25 mL) and brine (25 mL), dried over $Na_2SO_4$ and evaporated to give the title compound (0.06 g, 64%).

δ ($^1$H, 400 MHz, MeOD) 1.21-1.28 (2H, m), 1.76-1.79 (2H, m), 2.46-2.50 (2H, m), 2.58-2.62 (2H, m), 2.69-2.77 (2H, m), 3.15 (2H, t, J=6 Hz), 3.31-3.38 (2H, m), 3.51 (2H, s), 3.55-3.57 (2H, m), 3.87 (2H, q, J=8.7 Hz), 6.21-6.23 (1H, m), 7.21 (1H, d, J=7.8 Hz), 7.62-7.66 (2H, m), 7.73 (1H, s). MS (ES+) 525 ([MH]+).

Example 41

[6S/R,9R/S,11R/S] 2',3',4',5,5',6,7,8,9,10-Decahydro-2-(5-(1-trifluoroacetyl-1,2,3,6-tetrahydropyridin-4-yl)-thiazol-2-yl)-5'-(2,2,2-trifluoroethyl)-spiro[6,9-methanobenzocyclooctene-11,3'-[1,2,5]thiadiazole] 1',1'-dioxide

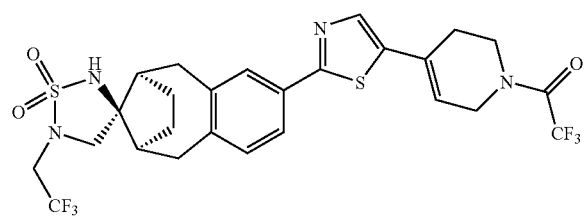

A solution of the tetrahydropyridine from Example 40 (0.05 g, 0.095 mmol) and triethylamine (54 µL, 0.38 mmol) in dichloromethane (2 mL) was cooled to 0° C. under nitrogen. Trifluoroacetic anhydride (80 µL, 0.57 mmol) was added dropwise and the reaction allowed to warm to room temperature overnight. The reaction was diluted with ethyl acetate (25 mL), washed with 10% aqueous sodium carbonate (25 mL) and brine (25 mL), dried over $Na_2SO_4$ and evaporated to give the title compound as a 2:1 mixture of rotamers (0.034 g, 58%). MS (ES+) 621 ([MH]+).

Example 42

[6S/R,9R/S,11R/S] 2',3',4',5,5',6,7,8,9,10-Decahydro-2-(5-(1-trifluoroacetylpiperidin-4-yl)-thiazol-2-yl)-5'-(2,2,2-trifluoroethyl)-spiro[6,9-methanobenzocyclooctene-11,3'-[1,2,5]thiadiazole] 1',1'-dioxide

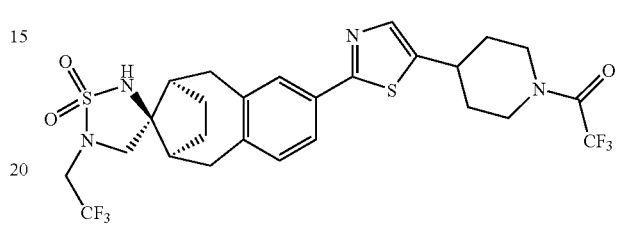

A mixture of the tetrahydropyridine from Example 41 (0.018 g, 0.029 mmol), palladium on carbon (0.01 g) and ethyl acetate (2 mL) was stirred under 1 atmosphere of hydrogen for 16 hours. The catalyst was removed by filtration through a glass fibre pad and the solvent removed in vacuo to give the title compound (0.018 g, quant.). δ ($^1$H, 400 MHz, CDCl$_3$) 1.29-1.38 (2H, m), 1.68-1.82 (4H, m), 2.16-2.20 (2H, m), 2.46-2.49 (2H, m), 2.70-2.80 (2H, m), 2.92-2.98 (1H, m), 3.18-3.33 (4H, m), 3.44 (2H, s), 3.64-3.72 (2H, m), 4.11-4.15 (1H, m), 4.64 (1H, d, J=14 Hz), 4.91 (1H, s) 7.15 (1H, d, J=7.8 Hz), 7.55 (1H, d, J=0.7 Hz), 7.61 (1H, dd, J=1.5 & 7.8 Hz), 7.66 (1H, s). MS (ES+) 623 ([MH]+).

Example 43

(−)-[6S,9R,11R] 2',3',4',5,5',6,7,8,9,10-Decahydro-2-(5-(1-tert-Butoxycarbonyl-1,2,3,6-tetrahydropyridin-4-yl)-thiazol-2-yl)-5'-(2,2,2-trifluoroethyl)-spiro[6,9-methanobenzocyclooctene-1,3'-[1,2,5]thiadiazole] 1',1'-dioxide

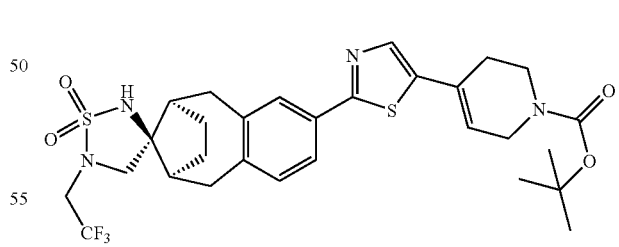

Prepared using [6S,9R,11R] 2',3',4',5,5',6,7,8,9,10-Decahydro-2-(5-bromothiazol-2-yl)-5'-(2,2,2-trifluoroethyl)-spiro[6,9-methanobenzocyclooctene-11,3'-[1,2,5]thiadiazole] 1',1'-dioxide (prepared using the homochiral boronate from Example 24 Step 1 by the method described for Example 36 Steps 1-2) and the boronate from Example 39 Step 2 using the method described for Example 36 Step 3. MS (ES+) 625 ([MH]+).; [α]$_D$=−11 (c=0.62, DMSO, 23° C.).

Example 44

[6S,9R,11R] 2',3',4',5,5',6,7,8,9,10-Decahydro-2-(4-methyl-5-(4-fluorophenyl)-thiazol-2-yl)-5'-(2,2,2-trifluoroethyl)-spiro[6,9-methanobenzocyclooctene-11,3'-[1,2,5]thiadiazole] 1',1'-dioxide

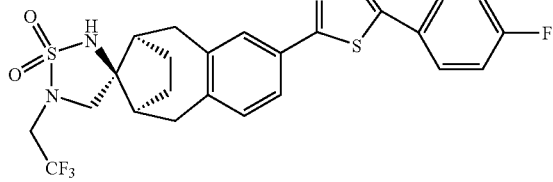

Step 1: 4-methyl-5-bromothiazole

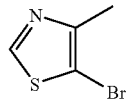

4-methylthiazole (200 μL, 2.2 mmol) and bromine (112 μL, 2.2 mmol) in acetic acid (2 mL) were protected from the light and stirred for 16 hours at room temperature. The mixture was washed with 10% aqueous sodium carbonate and extracted with ethyl acetate. The organic layers were washed with brine, dried over $Na_2SO_4$ and evaporated to give 4-methyl-5-bromothiazole (0.085 g, 22%). δ ($^1$H, 400 MHz, $CDCl_3$) 2.45 (3H, s), 8.69 (1H, s).

Step 2: 4-methyl-5-(4-fluorophenyl)thiazole

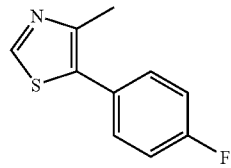

Prepared from the bromothiazole from Step 1 and 4-fluorobenzeneboronic acid by the method described for Example 36 Step 3. □ ($^1$H, 400 MHz, $CDCl_3$) 2.51 (3H, s), 7.10-7.15 (2H, m), 7.39-7.43 (2H, m), 8.68 (1H, s). MS (ES+) 194 ([MH]$^+$).

Step 3: 2-bromo-4-methyl-5-(4-fluorophenyl)thiazole

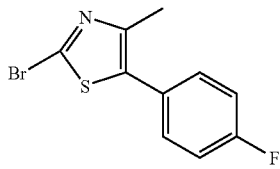

Prepared from the thiazole from Step 2 by the method described for Example 36 Step 2.

δ ($^1$H, 400 MHz, $CDCl_3$) 2.43 (3H, s), 7.10-7.15 (2H, m), 7.34-7.37 (2H, m). MS (ES+) 272,274 ([MH]$^{30}$).

Step 4: [6S,9R,11R] 2',3',4',5,5',6,7,8,9,10-Decahydro-2-(4-methyl-5-(4-fluorophenyl)-thiazol-2-yl)-5'-(2,2,2-trifluoroethyl)-spiro[6,9-methanobenzocyclooctene-11,3'-[1,2,5]thiadiazole] 1',1'-dioxide

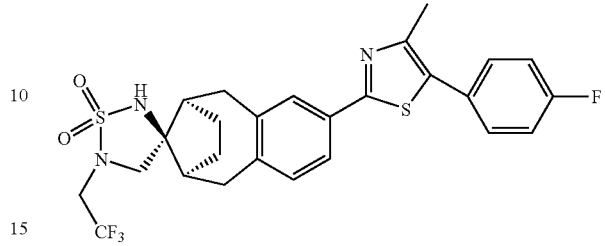

Prepared from the bromothiazole from Step 3 and the homochiral boronate from Example 24 Step 1 by the method described for Example 36 Step 3.

MS (ES+) 552 ([MH]$^+$).

Example 45

[6S/R,9R/S,11R/S] 2',3',4',5,5',6,7,8,9,10-Decahydro-2-(5-(4-methoxyphenyl)-thiazol-2-yl)-5'-(2,2,2-trifluoroethyl)-spiro[6,9-methanobenzocyclooctene-11,3'-[1,2,5]thiadiazole] 1',1'-dioxide

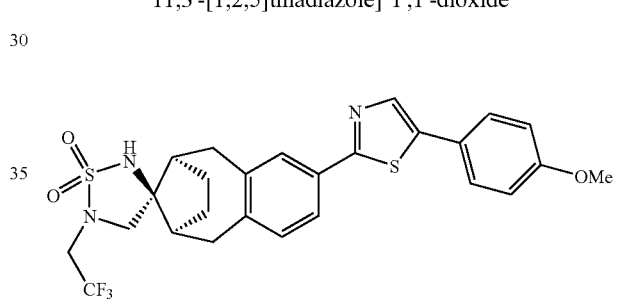

Prepared using the bromide from Example 36 Step 2 and 4-methoxybenzeneboronic acid by the method described for Example 36 Step 3. MS (ES+) 550 ([MH]$^+$).

Example 46

[6S/R,9R/S,11R/S] 2',3',4',5,5',6,7,8,9,10-Decahydro-2-(5-(2-fluorophenyl)-thiazol-2-yl)-5'-(2,2,2-trifluoroethyl)-spiro[6,9-methanobenzocyclooctene-11,3'-[1,2,5]thiadiazole] 1',1'-dioxide

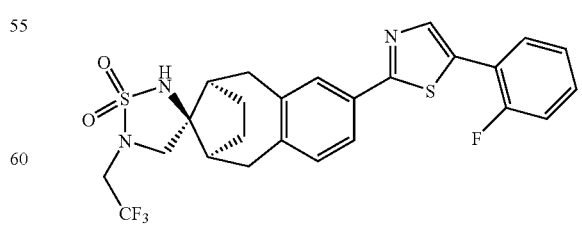

Prepared using the bromide from Example 36 Step 2 and 2-fluorobenzeneboronic acid by the method described for Example 36 Step 3. MS (ES+) 538 ([MH]$^+$).

Example 47

[6S/R,9R/S,11R/S] 2',3',4',5,5',6,7,8,9,10-Decahydro-2-(5-(4-trifluoromethylphenyl)-thiazol-2-yl)-5'-(2,2,2-tifluoroethyl)-spiro[6,9-methanobenzocyclooctene-11,3'-[1,2,5]thiadiazole] 1',1'-dioxide

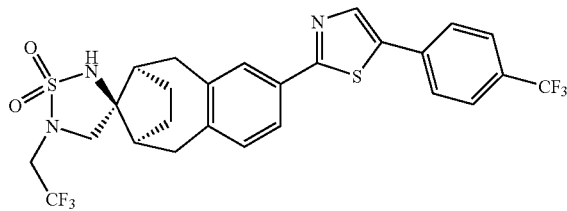

Prepared using the bromide from Example 36 Step 2 and 4-trifluoromethylbenzeneboronic acid by the method described for Example 36 Step 3. MS (ES+) 588 ([MH]+).

Example 48

[6S/R,9R/S,11R/S] 2',3',4',5,5',6,7,8,9,10-Decahydro-2-(5-(3-pyridyl)-thiazol-2-yl)-5'-(2,2,2-trifluoroethyl)-spiro[6,9-methanobenzocyclooctene-11,3'-[1,2,5]thiadiazole] 1',1'-dioxide

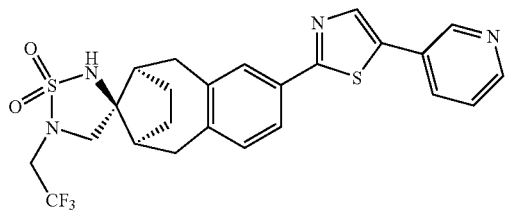

Prepared using the bromide from Example 36 Step 2 and 3-pyridylboronic acid by the method described for Example 36 Step 3. MS (ES+) 521 ([MH]+).

Example 49

[6S/R,9R/S,11R/S] 2',3',4',5,5',6,7,8,9,10-Decahydro-2-(5-(2-trifluoromethylphenyl)-thiazol-2-yl)-5'-(2,2,2-trifluoroethyl)-spiro[6,9-methanobenzocyclooctene-11,3'-[1,2,5]thiadiazole] 1',1'-dioxide

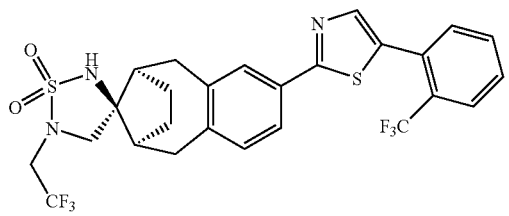

Prepared using the bromide from Example 36 Step 2 and 2-trifluoromethylbenzeneboronic acid by the method described for Example 36 Step 3. MS (ES+) 588 ([MH]+).

Example 50

[6S/R,9R/S,11R/S] 2',3',4',5,5',6,7,8,9,10-Decahydro-2-(5-(2-pyridyl)-thiazol-2-yl)-5'-(2,2,2-trifluoroethyl)-spiro[6,9-methanobenzocyclooctene-11,3'-[1,2,5]thiadiazole] 1',1'-dioxide

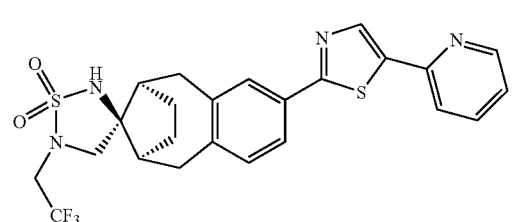

Prepared using the bromide from Example 36 Step 2 and 2-pyridylboronic acid by the method described for Example 36 Step 3. MS (ES+) 521 ([MH]+).

Example 51

[6S/R,9R/S,11R/S] 2',3',4',5,5',6,7,8,9,10-Decahydro-2-(5-(4-pyridyl)-thiazol-2-yl)-5'-(2,2,2-trifluoroethyl)-spiro[6,9-methanobenzocyclooctene-11,3'-[1,2,5]thiadiazole] 1',1'-dioxide

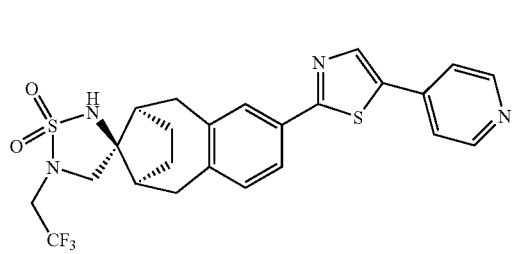

Prepared using the bromide from Example 36 Step 2 and 4-pyridylboronic acid by the method described for Example 36 Step 3. MS (ES+) 521 ([MH]+).

Example 52

[6S/R,9R/S,11R/S] 2',3',4',5,5',6,7,8,9,10-Decahydro-2-(5-(2-fluorophenyl)-1-methyl-pyrazol-3-yl)-5'-(2,2,2-trifluoroethyl)-spiro[6,9-methanobenzocyclooctene-11,3'-[1,2,5]thiadiazole] 1',1'-dioxide

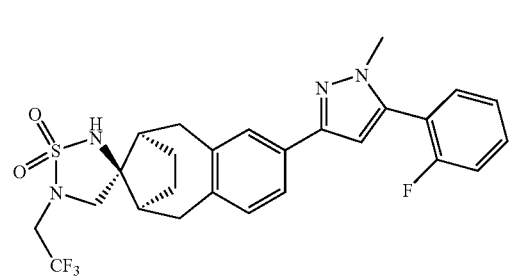

Step 1: [6S/R,9R/S,11R/S] 2',3',4',5,5',6,7,8,9,10-Decahydro-2-(2-ethoxycarbonylacetyl)-5'-(2,2,2-trifluoroethyl)-spiro[6,9-methanobenzocyclooctene-11,3'-[1,2,5]thiadiazole] 1',1'-dioxide

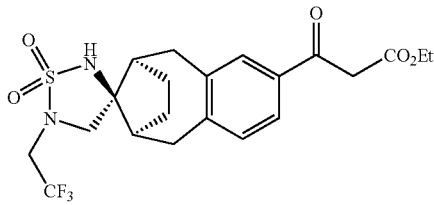

Catalytic N,N-dimethylformamide (2 drops) was added to a stirred solution of the acid Intermediate A (0.75 g, 1.86 mmol) and oxalyl chloride (0.65 mL, 7.4 mmol) in dry dichloromethane (20 mL) at room temperature under nitrogen. The effervescent mixture was stirred at room temperature for 18 hours. Solvents and excess reagents were removed in vacuo to give the acid chloride as an orange foam. A solution of isopropylmagnesium chloride (2M in THF; 5.6 mL, 11.2 mmol) was added at −78° C. to a stirred solution of ethyl hydrogen malonate (0.74 g, 5.6 mmol) in dry tetrahydrofuran (20 mL) under nitrogen. After 25 minutes stirring at −78° C., a solution of the acid chloride in tetrahydrofuran (10 mL) was added. The orange solution was warmed to room temperature. After stirring at room temperature for 1.5 hours, 1 M aqueous hydrochloric acid (45 mL) was added. When effervescence had subsided, the mixture was extracted with ethyl acetate (2×50 mL). The combined organic layers were washed with 0.2 M aqueous sodium hydroxide (2×30 mL) and brine (20 mL), dried over $Na_2SO_4$ and concentrated. The residue was purified by flash column chromatography on silica, eluting with 50% ethyl acetate-isohexane, to give the keto-ester as a pale yellow foam (0.732 g, 83%). NMR shows ~5:1 keto:enol forms.

Keto form: δ ($^1$H, 360 MHz, $CDCl_3$) 1.26 (3H, t, J=7 Hz), 1.26-1.33 (2H, m), 1.72-1.77 (2H, m), 2.48-2.50 (2H, m), 2.76-2.82 (2H, m), 3.22-331 (2H, m), 3.41-3.47 (2H, m), 3.69 (2H, q, J=8.7 Hz), 3.96 (2H, s), 4.22 (2H, q, J=7 Hz), 4.75 (1H, s), 7.21 (1H, d, J=7.6 Hz), 7.68-7.70 (2H, m).

Step 2: [6S/R,9R/S,11R/S] 2',3',4',5,5',6,7,8,9,10-Decahydro-2-(1-methyl-pyrazol-5-on-3-yl)-5'-(2,2,2-trifluoroethyl)-spiro[6,9-methanobenzocyclooctene-11,3'-[1,2,5]thiadiazole] 1',1'-dioxide

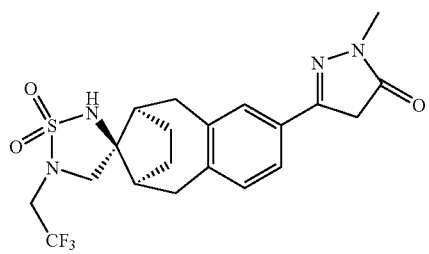

Methylhydrazine (0.5 mL, 9 mmol) was added dropwise to a stirred solution of the keto-ester from Step 1 (0.44 g, 0.93 mmol) in acetic acid (3 mL), moderating the exotherm with water-bath cooling. The reaction was stirred at room temperature for 18 hours. Water (50 mL) was added and the orange precipitates were collected, dissolved in ethyl acetate (100 mL), washed with water (10 mL), dried over $Na_2SO_4$ and concentrated. The residue was purified by flash column chromatography on silica, eluting with ethyl acetate, to give the pyrazolone as a yellow solid (0.504 g, 54%). δ ($^1$H, 360 MHz, $CDCl_3$) 1.27-1.33 (2H, m), 1.71-1.76 (2H, m), 2.45-2.50 (2H, m), 2.70-2.79 (2H, m), 3.22-3.27 (2H, m), 3.40 (3H, s), 3.44 (2H, s), 3.54-3.3.59 (2H, m), 3.69 (2H, q, J=8.7 Hz), 4.85 (1H, s), 7.15 (1H, d, J=7.8 Hz), 7.37 (1H, d, J=7.8 Hz), 7.44 (1H, s).

Step 3: [6S/R,9R/S,11R/S] 2',3',4',5,5',6,7,8,9,10-Decahydro-2-(5-trifluoromethanesulphonyloxy-1-methyl-pyrazol-3-yl)-5'-(2,2,2-trifluoroethyl)-spiro[6,9-methanobenzocyclooctene-11,3'-[1,2,5]thiadiazole] 1',1'-dioxide

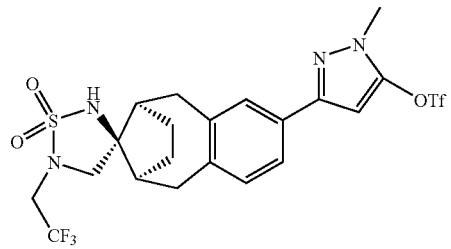

Trifluoromethanesulfonic anhydride (0.12 mL, 0.71 mmol) was added dropwise to a stirred suspension of the pyrazolone from Step 2 (0.15 g, 0.329 mmol) and pyridine (0.07 mL, 0.80 mmol) in dichloromethane (3 mL) at −78° C. under nitrogen. After stirring for 3 hours, the reaction was quenched at −78° C. withs saturated aqueous sodium hydrogencarbonate (25 mL) and extracted with dichloromethane (25 mL). The organic layer was dried over $Na_2SO_4$ and concentrated. The residue was purified by flash column chromatography on silica, eluting with 30% ethyl acetate-isohexane, to give the triflate as a pink oil (0.114 g, 59%). δ ($^1$H, 360 MHz, $CDCl_3$) 1.32-1.37 (2H, m), 1.69-1.74 (2H, m), 2.42-2.49 (2H, m), 2.69-2.81 (2H, m), 3.20-3.25 (2H, m), 3.44 (2H, s), 3.68 (2H, q, J=8.7 Hz), 3.86 (3H, s), 4.66 (1H, s), 6.41 (1H, s) 7.14 (1H, d, J=7.8 Hz), 7.47 (1H, d, J=7.8 Hz), 7.51 (1H, s).

Step 4: [6S/R,9R/S,11R/S] 2',3',4',5,5',6,7,8,9,10-Decahydro-2-(5-(2-fluorophenyl)-1-methyl-pyrazol-3-yl)-5'-(2,2,2-trifluoroethyl)-spiro[6,9-methanobenzocyclooctene-11,3'-[1,2,5]thiadiazole] 1',1'-dioxide

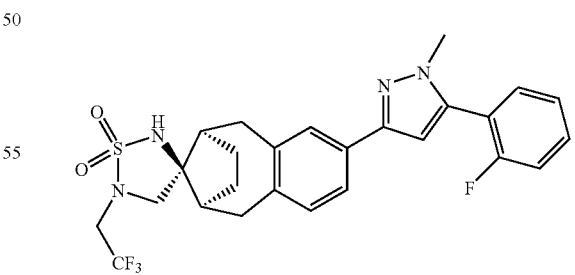

A mixture of the triflate from Step 3 (0.054 g, 0.092 mmol), tetrakis(triphenylphosphine) palladium(0) (0.025 g, 0.022 mmol), 2-fluorophenylboronic acid (0.025 g, 0.17 mmol) and 2 M aqueous sodium carbonate (0.15 mL, 0.3 mmol) in toluene (2 mL) was degassed and flushed with nitrogen at room temperature. The reaction was heated to reflux for 18

Example 53

[6S/R,9R/S,11R/S] 2',3',4',5,5',6,7,8,9,10-Decahydro-2-(5-(3-fluorophenyl)-1-methyl-pyrazol-3-yl)-5'-(2,2,2-trifluoroethyl)-spiro[6,9-methanobenzocyclooctene-11,3'-[1,2,5]thiadiazole] 1',1'-dioxide

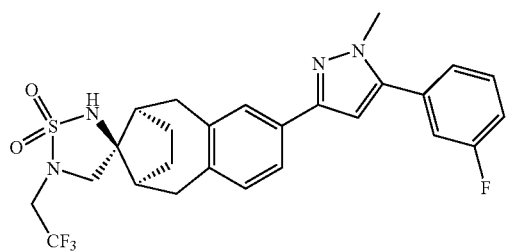

Prepared using Intermediate A and 3-fluorobenzeneboronic acid by the method described for Example 52. MS (ES+) 535 ([MH]⁺).

Example 54

[6S/R,9R/S,11R/S] 2',3',4',5,5',6,7,8,9,10-Decahydro-2-(5-(4-fluorophenyl)-1-ethyl-pyrazol-3-yl)-5'-(2,2,2-trifluoroethyl)-spiro[6,9-methanobenzocyclooctene-11,3'-[1,2,5]thiadiazole] 1',1'-dioxide

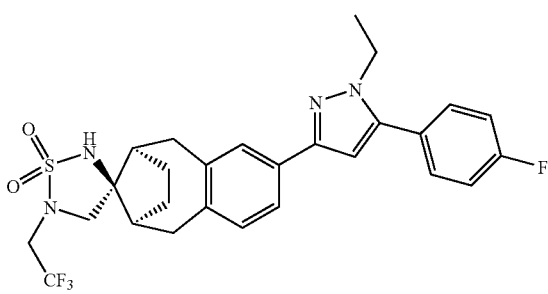

Prepared using Intermediate A, ethylhydrazine oxalate and 4-fluorobenzeneboronic acid by the method described for Example 52. MS (ES+) 549 ([MH]⁺).

Example 55

[6S,9R,11R] 2',3',4',5,5',6,7,8,9,10-Decahydro-2-(5-trifluoromethyl-1-methyl-pyrazol-3-yl)-5'-(2,2,2-trifluoroethyl)-spiro[6,9-methanobenzocyclooctene-11,3'-[1,2,5]thiadiazole] 1',1'-dioxide

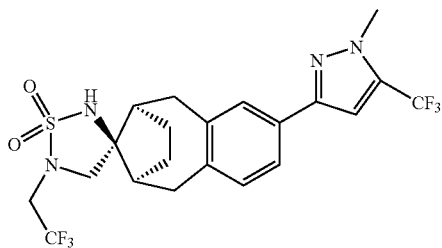

Step 1: 3-trifluoromethanesulphonyloxy-1-methyl-5-(trifluoromethyl)pyrazole

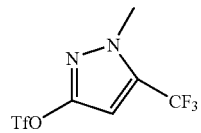

A solution of 3-hydroxy-1-methyl-5-(trifluoromethyl)pyrazole (0.227 g, 1.37 mmol), 2,6-lutidine (0.18 mL, 1.5 mmol) and trifluoromethanesulfonic anhydride (0.25 mL, 1.5 mmol) in dichloromethane (5 mL) was stirred for 18 hours at room temperature under nitrogen. The reaction mixture was washed with water (5 mL), dried over Na₂SO₄ and evaporated. The residue was purified by flash column chromatography on silica, eluting with 50% ethyl acetate—isohexane to give the triflate as a mobile yellow oil (0.18 g, 44%). δ (¹H, 400 MHz, CDCl₃) 3.97 (3H, s), 6.50 (1H, s).

Step 2: [6S,9R,11R] 2',3',4',5,5',6,7,8,9,10-Decahydro-2-(5-trifluoromethyl-1-methyl-pyrazol-3-yl)-5'-(2,2,2-trifluoroethyl)-spiro[6,9-methanobenzocyclooctene-11,3'-[1,2,5]thiadiazole] 1',1'-dioxide

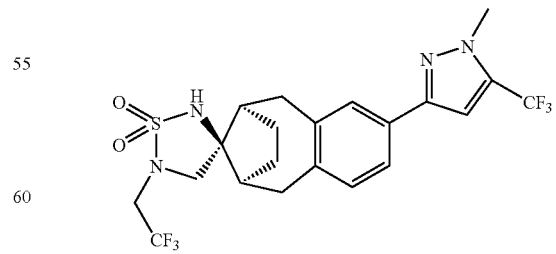

Prepared using the triflate from Step 1 and the homochiral boronate from Example 24 Step 1 by the method described for Example 52 Step 4. MS (ES+) 509 ([MH]⁺).

Example 56

[6S/R,9R/S,11R/S] 2',3',4',5,5',6,7,8,9,10-Decahydro-2-(5-(4-chlorophenyl)-1-methyl-pyrazol-3-yl)5'-(2,2,2-trifluoroethyl)-spiro[6,9-methanobenzocyclooctene-11,3'-[1,2,5]thiadiazole] 1',1'-dioxide

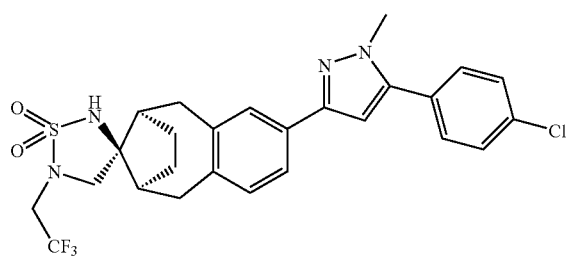

Prepared using Intermediate A and 4-chlorobenzeneboronic acid by the method described for Example 52. MS (ES+) 551 ([MH]$^+$).

Example 57

[6S/R,9R/S,11R/S] 2',3',4',5,5',6,7,8,9,10-Decahydro-2-(5-(2,4-dichlorophenyl)-1-methyl-pyrazol-3-yl)-5'-(2,2,2-trifluoroethyl)-spiro[6,9-methanobenzocyclooctene-11,3'-[1,2,5]thiadiazole] 1',1'-dioxide

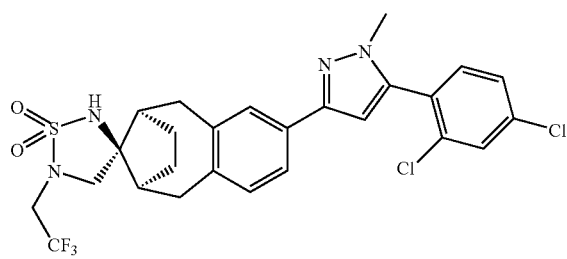

Prepared using Intermediate A and 2,4-dichlorobenzeneboronic acid by the method described for Example 52. MS (ES+) 585 ([MH]$^+$).

Example 58

[6S/R,9R/S,11R/S] 2',3',4',5,5',6,7,8,9,10-Decahydro-2-(5-(2,4-difluorophenyl)-1-methyl-pyrazol-3-yl)-5'-(2,2,2-trifluoroethyl)-spiro[6,9-methanobenzocyclooctene-11,3'-[1,2,5]thiadiazole] 1',1'-dioxide

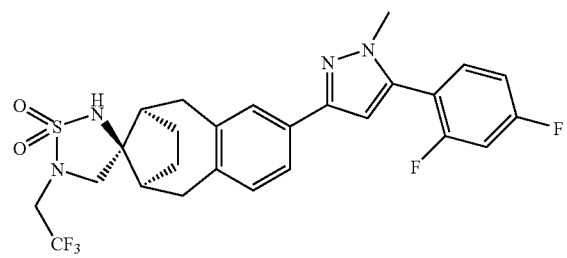

Prepared using Intermediate A and 2,4-difluorobenzeneboronic acid by the method described for Example 52. MS (ES+) 553 ([MH]$^+$).

Example 59

[6S/R,9R/S,11R/S] 2',3',4',5,5',6,7,8,9,10-Decahydro-2-(5-(4-fluorophenyl)-1-(2,2,2-trifluoroethyl)-pyrazol-3-yl)-5'-(2,2,2-trifluoroethyl)-spiro[6,9-methanobenzocyclooctene-11,3'-[1,2,5]thiadiazole] 1',1'-dioxide

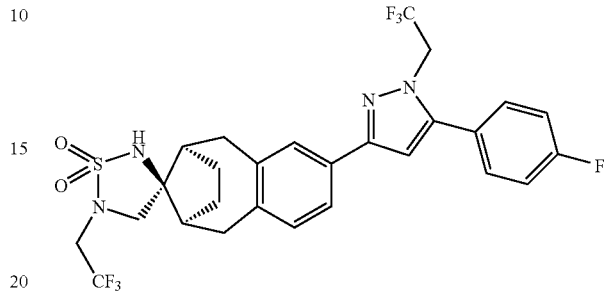

Prepared using Intermediate A, trifluoroethylhydrazine and 4-fluorobenzeneboronic acid by the method described for Example 52. MS (ES+) 603 ([MH]$^+$).

Example 60

[6S/R,9R/S,11R/S] 2',3',4',5,5',6,7,8,9,10-Decahydro-2-(5-(4-cyanophenyl)-1-methyl-pyrazol-3-yl)-5'-(2,2,2-trifluoroethyl)-spiro[6,9-methanobenzocyclooctene-11,3'-[1,2,5]thiadiazole] 1',1'-dioxide

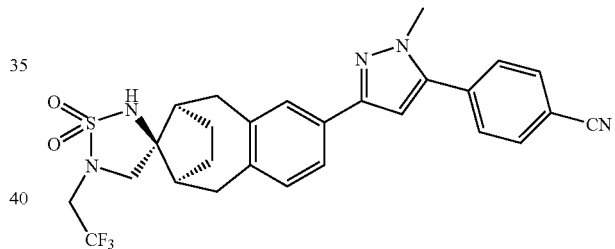

Prepared using Intermediate A and 4-cyanobenzeneboronic acid by the method described for Example 52. MS (ES+) 542 ([MH]$^+$).

Example 61

[6S/R,9R/S,11R/S] 2',3',4',5,5',6,7,8,9,10-Decahydro-2-(5-phenyl-1-methyl-pyrazol-3-yl)-5'-(2,2,2-trifluoroethyl)-spiro[6,9-methanobenzocyclooctene-11,3'-[1,2,5]thiadiazole] 1',1'-dioxide

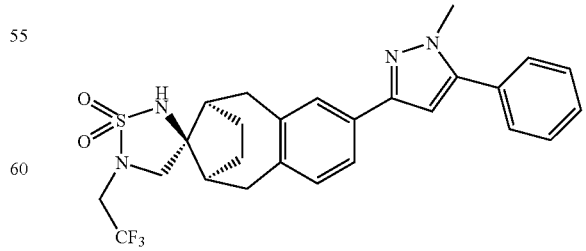

Prepared using Intermediate A and benzeneboronic acid by the method described for Example 52. MS (ES+) 517 ([MH]$^+$).

Example 62

[6S,9R,11R] 2',3',4',5,5',6,7,8,9,10-Decahydro-2-(5-(4-pyridyl)-1-methyl-pyrazol-3-yl)-5'-(2,2,2-trifluoroethyl)-spiro[6,9-methanobenzocyclooctene-11,3'-[1,2,5]thiadiazole] 1',1'-dioxide

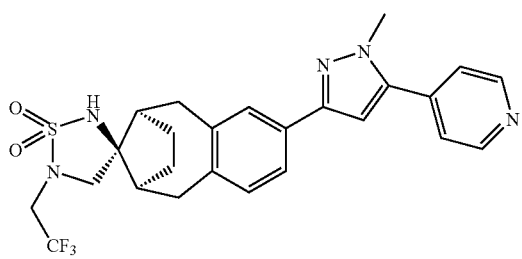

Prepared from Intermediate B and 4-pyridylboronic acid by the method described for Example 52. MS (ES+) 518 ([MH]+).

Example 63

[6S,9R,11R] 2',3',4',5,5',6,7,8,9,10-Decahydro-2-(5-(3-pyridyl)-1-methyl-pyrazol-3-yl)-5'-(2,2,2-trifluoroethyl)-spiro[6,9-methanobenzocyclooctene-11,3'-[1,2,5]thiadiazole] 1',1'-dioxide

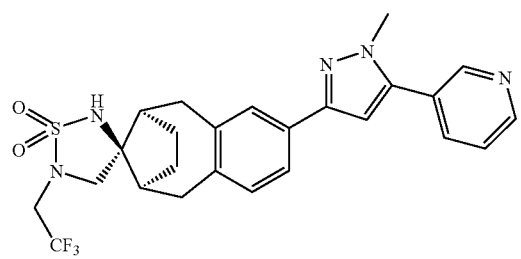

Prepared from Intermediate B and 3-pyridylboronic acid by the method described for Example 52. MS (ES+) 518 ([MH]+).

Example 64

[6S,9R,11R] 2',3',4',5,5',6,7,8,9,10-Decahydro-2-(5-(4-trifluoromethoxyphenyl)-1-methyl-pyrazol-3-yl)-5'-(2,2,2-trifluoroethyl)-spiro[6,9-methanobenzocyclooctene-11,3'-[1,2,5]thiadiazole] 1',1'-dioxide.

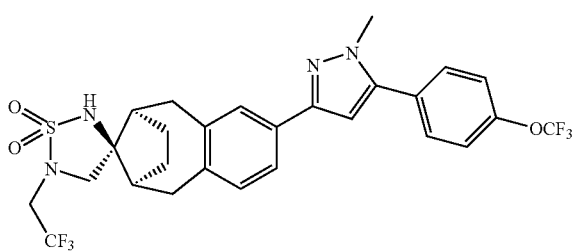

Prepared from Intermediate B and 4-trifluoromethoxybenzeneboronic acid by the method described for Example 52. MS (ES+) 601 ([MH]+).

Example 65

[6S,9R,11R] 2',3',4',5,5',6,7,8,9,10-Decahydro-2-(5-(3,4-difluorophenyl)-1-methyl-pyrazol-3-yl)-5'-(2,2,2-trifluoroethyl)-spiro[6,9-methanobenzocyclooctene-11,3'-[1,2,5]thiadiazole] 1',1'-dioxide

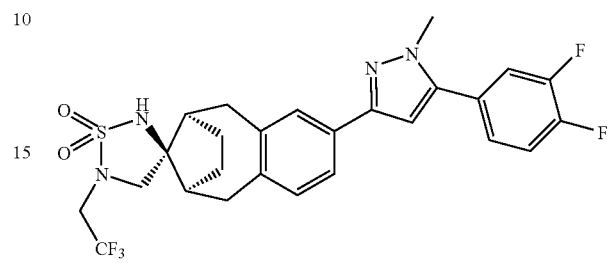

Prepared from Intermediate B and 3,4-difluorobenzeneboronic acid by the method described for Example 52. MS (ES+) 553 ([MH]+).

Example 66

[6S,9R,11R] 2',3',4',5,5',6,7,8,9,10-Decahydro-2-(5-(3,4,5-trifluorophenyl)-1-methyl-pyrazol-3-yl)-5'-(2,2,2-trifluoroethyl)-spiro[6,9-methanobenzocyclooctene-11,3'-[1,2,5]thiadiazole] 1',1'-dioxide

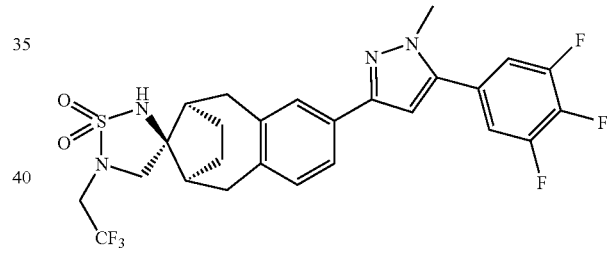

Prepared from Intermediate B and 3,4,5-trifluorobenzeneboronic acid by the method described for Example 52. MS (ES+) 571 ([MH]+).

Example 67

[6S,9R,11R] 2',3',4',5,5',6,7,8,9,10-Decahydro-2-(5-(4-chlorophenyl)-1-methyl-pyrazol-3-yl)-5'-trifluoroethyl)-spiro[6,9-methanobenzocyclooctene-11,3'-[1,2,5]thiadiazole] 1',1'-dioxide

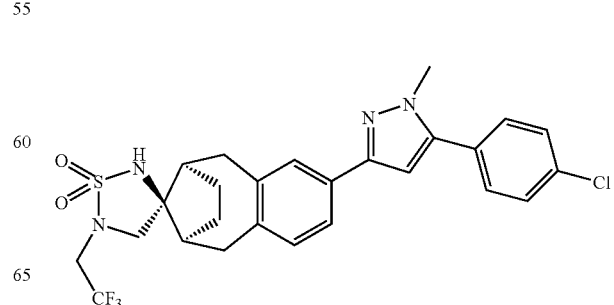

Prepared from Intermediate B and 4-chlorobenzeneboronic acid by the method described for Example 52. MS (ES+) 551 ([MH]+).

Example 68

[6S,9R,11R] 2',3',4',5,5',6,7,8,9,10-Decahydro-2-(5-(2,4-difluorophenyl)-1-methyl-pyrazol-3-yl)-5'-(2,2,2-trifluoroethyl)-spiro[6,9-methanobenzocyclooctene-1,3'-[1,2,5]thiadiazole] 1',1'-dioxide

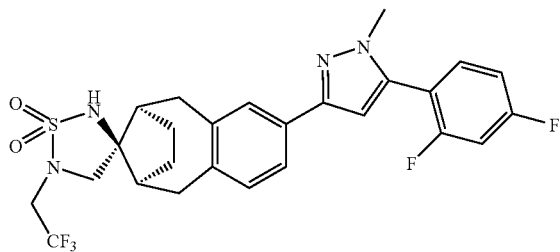

Prepared from Intermediate B and 2,4-difluorobenzeneboronic acid by the method described for Example 52. MS (ES+) 553 ([MH]+).

Example 69

[6S,9R,11R] 2',3',4',5,5',6,7,8,9,10-Decahydro-2-(5-(5-methylpyrid-2-yl)-1-methyl-pyrazol-3-yl)-5'-(2,2,2-trifluoroethyl)-spiro[6,9-methanobenzocyclooctene-11,3'-[1,2,5]thiadiazole] 1',1'-dioxide

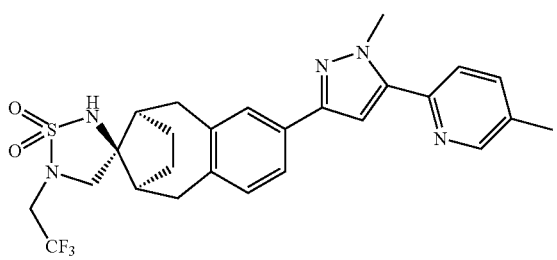

Step 1: 1-methyl-3-bromo-5-pyrazolone

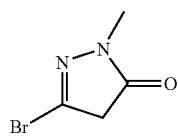

A solution of 3,3-dibromoprop-2-enoyl chloride (1.60 g, 6.44 mmol) (prepared as described in *Synthesis*, 1984, 434) in dry dichloromethane (10 mL) was added dropwise by syringe to a stirred solution of ethyl 3-methylcarbazate (0.77 g, 6.50 mmol) (prepared as described in *Arch. Pharm.* 1971, 304, 706) and triethylamine (0.90 mL, 6.50 mmol) in dry dichloromethane (10 mL) at 0° C. under nitrogen. After 2 hours, the solution was washed with 0.2M hydrochloric acid (30 mL). The aqueous washings were extracted with dichloromethane (20 mL). The combined organic layers were washed with brine (20 mL), dried (Na₂SO₄) and concentrated to give a pink oil (2.01 g). A solution of sodium hydroxide (2.10 g, 53 mmol) in water (42 mL) was warmed to 60° C. and added to the oil. The mixture was stirred at 60° C. for 25 min, then cooled slowly to room temperature over 1 hour and allowed to stand at room temperature for 1 hour. The solution was acidified by dropwise addition of concentrated hydrochloric acid. After chilling for 30 min, the white precipitate was collected. The aqueous layer was extracted with 10% methanol—dichloromethane (60 mL). The collected solids were dissolved in the organic extract, and the solution was dried (Na₂SO₄) and concentrated to give a yellow solid. The solid was rinsed with diethyl ether and dried under vacuum to give 1-methyl-3-bromo-5-pyrazolone as a yellow powder (0.56 g, 49%). δ (¹H, 400 MHz, CDCl₃) 3.33 (3H, s), 3.47 (2H, s).

Step 2: 1-methyl-3-bromo-5-(nonafluorobutanesulfonyloxy)pyrazole

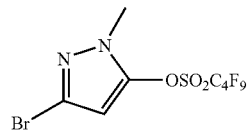

A solution of sodium bis(trimethylsilyl)amide in tetrahydrofuran (1M, 0.70 mL, 0.70 mmol) was added at −78° C. under nitrogen to a stirred solution of 1-methyl-3-bromo-5-pyrazolone from Step 1 (0.10 g, mmol) in dry tetrahydrofuran (2 mL). After 10 min, nonafluorobutanesulfonyl fluoride (0.13 mL, 0.70 mmol) was added dropwise. The resulting gel was warmed to room temperature and stirred for 1 hour. The solution was diluted with water (10 mL) and extracted with ethyl acetate (2×10 mL). The extracts were dried (Na₂SO₄) and concentrated. Flash column chromatography on silica, eluting with 10% ethyl acetate—isohexane, gave 1-methyl-3-bromo-5-(nonafluorobutanesulfonyloxy)pyrazole (0.204 g, 79%) as a colourless oil. δ (¹H, 500 MHz, CDCl₃) 3.80 (3H, s), 6.19 (1H, s).

Step 3: 1-methyl-3-bromo-5-(5-methylpyridin-2-yl)pyrazole

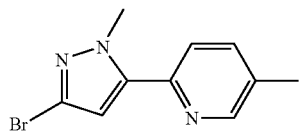

A solution of 1-methyl-3-bromo-5-(nonafluorobutanesulfonyloxy)pyrazole from Step 2 (0.36 g, 0.784 mmol) and tetrakis(triphenylphosphine) palladium (0) (0.09 g, 10 mol %) in dry N,N-dimethylformamide (2 mL) was stirred under nitrogen at 60° C. for 10 min, followed by addition of a solution of 5-methylpyridin-2-ylzinc bromide in tetrahydrofuran (0.5M, 1.8 mL, 0.9 mmol). The solution was stirred at 60° C. for 18 hours then cooled, diluted with water (30 mL), and extracted with ethyl acetate (2×20 mL). The extracts were dried (Na₂SO₄) and concentrated. Flash column chromatography on silica, eluting with 10% ethyl acetate—isohexane, gave 1-methyl-3-bromo-5-(5-methylpyridin-2-yl)pyrazole (0.081 g, 41%) as a yellow solid. MS (ES+) 252, 254 ([MH]+).

Step 4: [6S,9R,11R] 2',3',4',5,5',6,7,8,9,10-decahydro-2-(5-(5-methylprid-2-yl)-1-methyl-pyrazol-3-yl)-5'-(2,2,2-trifluoroethyl)-spiro[6,9-methanobenzocyclooctene-11,3'-[1,2,5]thiadiazole] 1',1'-dioxide

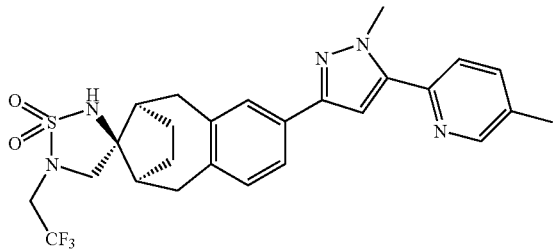

A mixture of 1-methyl-3-bromo-5-(5-methylpyridin-2-yl)pyrazole from Step 3 (0.081 g, 0.321 mmol), the homochiral boronate from Example 24 Step 1 (0.156 g, 0.321 mmol), cesium carbonate (0.10 g, 0.32 mmol) and tetrakis(triphenylphosphine) palladium (0) (0.04 g, 10 mol %) in N,N-dimethylformamide (3 mL) and water (1 mL) was degassed and flushed with nitrogen, then stirred at 100° C. under nitrogen for 18 hours. The cooled mixture was diluted with water (20 mL) and extracted with ethyl acetate (20 mL). The extract was dried ($Na_2SO_4$), filtered through a plug of silica gel and concentrated. The residual oil was partitioned between water (10 mL) and diethyl ether (10 mL). The organic layer was dried ($Na_2SO_4$) and concentrated. The material was purified by normal-phase preparative HPLC, eluting with ethyl acetate—isohexanes, to give the title compound (0.039 g, 23%) as a beige solid. δ ($^1$H, 400 MHz, $CDCl_3$) 1.34-1.43 (2H, m), 1.68-1.74 (2H; m), 2.40 (3H, s), 2.44-2.48 (2H, m), 2.69-2.83 (2H, m), 3.21-3.25 (2H, m), 3.44 (2H, s), 3.68 (2H, q, J=8.7 Hz), 4.24 (3H, s), 4.68 (1H, s), 6.81 (1H, s), 7.13 (1H, d, J=7.6 Hz), 7.51-7.59 (3H, m), 7.62 (1H, d, J=1.6 Hz), 8.52 (1H, d, J=1.6 Hz). MS (ES+) 532 ([MH]$^+$).

Example 70

[6S,9R,11R] 2',3',4',5,5',6,7,8,9,10-Decahydro-2-(5-(3-chloro-4-fluorophenyl)-1-methyl-pyrazol-3-yl)-5'-(2,2,2-trifluoroethyl)-spiro[6,9-methanobenzocyclooctene-11,3'-[1,2,5]thiadiazole] 1',1'-dioxide

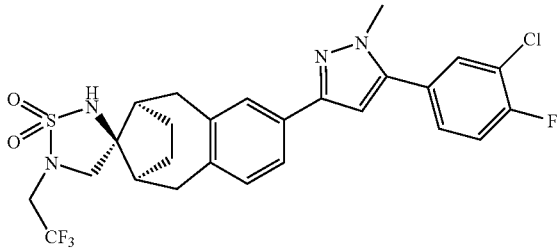

Prepared by the method described for Example 69, using 3-chloro-4-fluorophenylzinc iodide in Step 3. MS (ES+) 569 ([MH]$^+$).

Example 71

[6S,9R,11R] 2',3',4',5,5',6,7,8,9,10-Decahydro-2-(5-(3,4-dichlorophenyl)-1-methyl-pyrazol-3-yl)-5'-(2,2,2-trifluoroethyl)-spiro[6,9-methanobenzocyclooctene-11,3'-[1,2,5]thiadiazole] 1',1'-dioxide

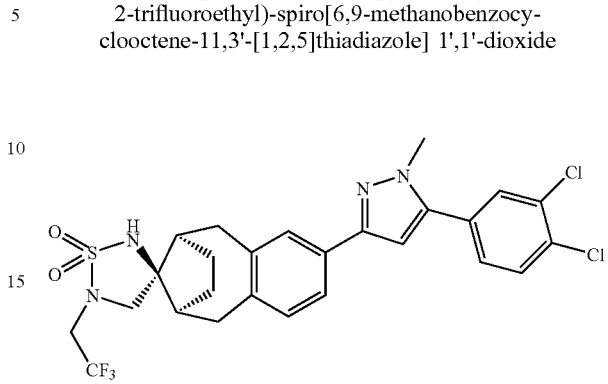

Prepared by the method described for Example 69, using 3,4-dichlorophenylzinc iodide in Step 3. MS (ES+) 551 ([MH]$^+$).

Example 72

[6S,9R,11R] 2',3',4',5,5',6,7,8,9,10-Decahydro-2-(5-(4-trifluoromethylphenyl)-1-methyl-pyrazol-3-yl)-5'-(2,2,2-trifluoroethyl)-spiro[6,9-methanobenzocyclooctene-11,3'-[1,2,5]thiadiazole] 1',1'-dioxide

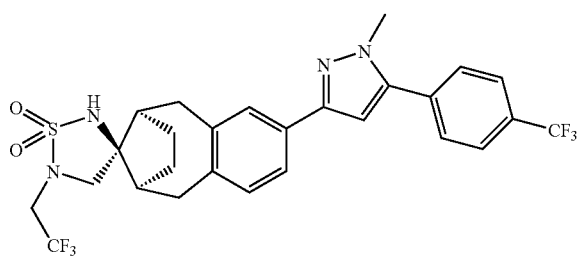

Step 1: 1-methyl-3-bromo-5-(4-trifluoromethylphenyl)pyrazole

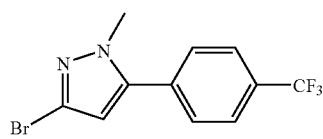

A solution of 1-methyl-3-bromo-5-(nonafluorobutanesulfonyloxy)pyrazole from Example 69 Step 2 (0.16 g, 0.35 mmol), 4-trifluoromethylbenzeneboronic acid (0.07 g, 0.36 mmol), tetrakis(triphenylphosphine) palladium (0) (0.04 g, 10 mol %), sodium carbonate (0.04 g, 0.38 mmol) in dry N,N-dimethylformamide (2 mL) was stirred under nitrogen at 40° C. for 18 hours. The cooled reaction mixture was poured into 1M hydrochloric acid (10 ml) and extracted with diethyl ether (2×10 mL). The combined organic layers were dried ($Na_2SO_4$) and concentrated to give an oil which was purified by flash column chromatography on silica eluting with 5% ethyl acetate—isohexane to give 1-methyl-3- bromo-5-(4-trifluoromethylphenyl)pyrazole as a white solid (0.06 g, 56%). δ (¹H, 400 MHz, CDCl₃) 3.86 (3H, s), 6.37 (1H, s), 7.53 (2H, d, J=8 Hz), 7.74 (2H, d, J=8 Hz).

Step 2: [6S,9R,11R] 2',3',4',5,5',6,7,8,9,10-decahydro-2-(5-(4-trifluoromethylphenyl)-1-methyl-pyrazol-3-yl)-5'-(2,2,2-trifluoroethyl)-spiro[6,9-methanobenzocyclooctene-11,3'-[1,2,5]thiadiazole] 1',1'-dioxide

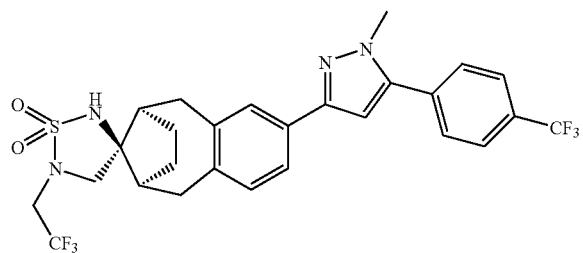

Prepared by the method of Example 69 Step 4. MS (ES+) 451 ([MH]⁺).

Example 73

[6S,9R,11R] 2',3',4',5,5',6,7,8,9,10-Decahydro-2-(5-(4-methylphenyl)-1-methyl-pyrazol-3-yl)-5'-(2,2,2-trifluoroethyl)-spiro[6,9-methanobenzocyclooctene-11,3'-[1,2,5]thiadiazole] 1',1'-dioxide

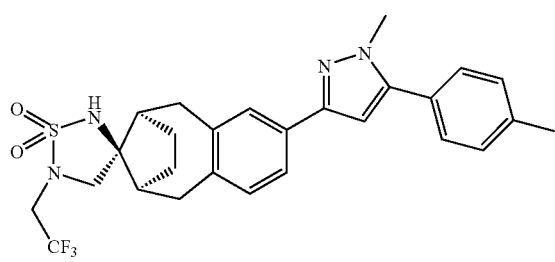

Prepared by the method described for Example 72, using 4-methylbenzeneboronic acid at 100° C. in Step 1. MS (ES+) 531 ([MH]⁺).

Example 74

[6S/R,9R/S,11R/S] 2',3',4',5,5',6,7,8,9,10-Decahydro-2-(4-phenylimidazol-1-yl)-5'-(2,2,2-trifluoroethyl)-spiro[6,9-methanobenzocyclooctene-11,3'-[1,2,5]thiadiazole] 1',1'-dioxide

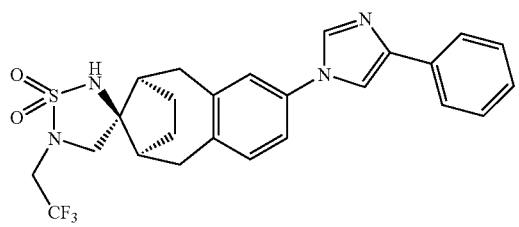

Sodium periodate (99 mg, 0.46 mmol) was added to a solution of the racemic boronate from Example 36 Step 1 (75 mg, 0.15 mmol) in tetrahydrofuran (2 mL) and water (0.5 mL) and stirred for 2 hours at room temperature. 2M aqueous hydrochloric acid (50 µL) was added and stirred for 18 hours at room temperature. The reaction was diluted with ethyl acetate, washed with water and brine, dried (Na₂SO₄) and concentrated to give the crude boronic acid. 62 mg (0.15 mmol) of this, 4-phenylimidazole (22 mg, 0.15 mmol) and (di-µ-hydroxo-bis(N,N,N',N'-tetramethylethylene diamine) copper(II) chloride (7 mg, 0.02 mmol) in dichloromethane (4 mL) were stirred in an open flask for 18 hours at room temperature. The mixture was filtered through Celite® and washed with ethyl acetate. The filtrate was concentrated and the residue purified by flash column chromatography on silica eluting with ethyl acetate/isohexane (gradient 50% to 70% to neat ethyl acetate) to give the title compound as a white solid (34 mg, 44%). δ (¹H, 500 MHz, CDCl₃) 1.32-1.40 (2H, m), 1.77-1.79 (2H, m), 2.49-2.53 (2H, m), 2.74-2.80 (2H, m), 3.26 (1H, d, J=16 Hz), 3.3.1 (1H, d, J=16 Hz), 3.44-3.48 (2H, m), 3.67-3.72 (2H, m), 4.72 (1H, s), 7.20-7.29 (4H, m), 7.41 (2H, t, J=7.4 Hz), 7.54 (1H, d, J=1.1 Hz), 7.84 (2H, d, J=7.4 Hz), 7.87 (1H, d, J=1.1 Hz). MS (ES+) 503 ([MH]⁺).

Example 75

[6S/R,9R/S,11R/S] 2',3',4',5,5',6,7,8,9,10-Decahydro-2-(5-(4-fluorophenyl)-1-methyl-1,2,4-triazol-3-yl)-5'-(2,2,2-trifluoroethyl)-spiro[6,9-methanobenzocyclooctene-11,3'-[1,2,5]thiadiazole] 1',1'-dioxide

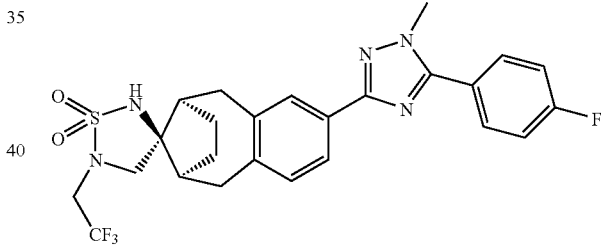

Step 1: [6S/R,9R/S,11R/S] 2',3',4',5,5',6,7,8,9,10-Decahydro-2-carbomethoxy-5'-(2,2,2-trifluoroethyl)-spiro-[6,9-methanobenzocyclooctene-11,3'-[1,2,5]thiadiazole] 1',1'-dioxide

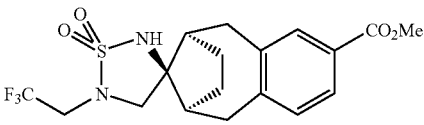

A solution of Intermediate D (6.7 g, 13 mmol), 1,3-bis (diphenylphosphino)propane (540 mg, 1.3 mmol) and triethylamine (25 mL, 180 mmol) in dry dimethylsulfoxide (180 mL) and methanol (120 mL) was deoxygenated by bubbling carbon monoxide through the solution for 15 minutes. Palladium (II) acetate (300 mg, 1.3 mmol) was added and deoxygenation was continued for a further 5 minutes. The reaction was then heated at 80° C. for 4 hours, with a slow stream of carbon monoxide bubbling though the solution. The reaction was allowed to cool, then diluted with water (1 L). The mixture was extracted with ethyl acetate (×3). The combined organic layers were washed with brine, dried (Na₂SO₄) and evaporated. The residue was purified by flash column chromatography on silica, eluting with 100% dichloromethane to 5% ethyl acetate/dichloromethane, to give the ester (4.8 g, 88%) as a pale yellow solid. δ (¹H, 360 MHz, CDCl₃) 1.28 (2H, m), 1.72 (2H, m), 2.48 (2H, brm), 2.78 (2H, m), 3.23 (1H, d, J=15.4 Hz), 3.27 (1H, d, J=15.4 Hz), 3.43 (2H, ABq, J=9.5, 11.1 Hz), 3.68 (2H, q, J=8.7 Hz), 3.90 (3H, s), 4.79 (1H, s), 7.17 (1H, d, J=8.3 Hz), 7.78 (2H, m).

Step 2: [6S/R,9R/S,11R/S] 2',3',4',5,5',6,7,8,9,10-Decahydro-2-hydroxymethyl-5'-(2,2,2-trifluoroethyl)-spiro-[6,9-methanobenzocyclooctene-11,3'-[1,2,5]thiadiazole] 1',1'-dioxide

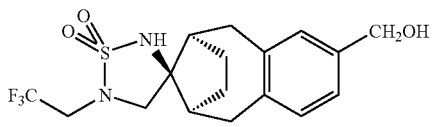

Diisobutylaluminium hydride (1M in toluene, 49 mL, 49 mmol) was added slowly to a stirred solution of the product from Step 1 (5.1 g, 12.2 mmol) in dry tetrahydrofuran (100 mL) at −78° C. under nitrogen. After 30 minutes the reaction was allowed to warm to −10° C. and maintained at this temperature for 3 hours. The reaction was quenched with methanol and allowed to warm to room temperature. 1M Aqueous hydrochloric acid (100 mL) was added slowly. The mixture was extracted with ethyl acetate (×3). The combined organic layers were washed with brine, dried (Na₂SO₄) and evaporated to give a dark foam (5.2 g) which was used without further purification. δ (¹H, 360 MHz, CDCl₃) 1.35 (2H, m), 1.71 (2H, m), 2.43 (2H, brm), 2.68 (1H, d, J=16.1), 2.70 (1H, d, J=16.1 Hz), 3.17 (1H, d, J=15.9 Hz), 3.20 (1H, d, J=15.9 Hz), 3.43 (2H, s), 3.69 (2H, q, J=8.7 Hz), 4.65 (2H, brs), 4.73 (1H, s), 7.10 (3H, m).

Step 3: [6S/R,9R/S,11R/S] 2',3',4',5,5',6,7,8,9,10-Decahydro-2-carboxaldehyde-5'-(2,2,2-trifluoroethyl)-spiro[6,9-methanobenzocyclooctene-11,3'-[1,2,5]thiadiazole] 1',1'-dioxide

Pyridinium dichromate (6.9 g, 18 mmol) was added to a stirred solution of the product from Step 2 (5.2 g) in dry dichloromethane (120 mL) at room temperature. The mixture was stirred at this temperature overnight, then loaded directly on to a pad of silica. The pad was eluted with dichloromethane, then 20% ethyl acetate/dichloromethane to give the aldehyde (4.2 g, 89%) as a pale yellow solid. δ (¹H, 360 MHz, CDCl₃) 1.27 (2H, m), 1.74 (2H, m), 2.50 (2H, brm), 2.82 (2H, m), 3.26 (1H, d, J=13.9 Hz), 3.30 (1H, d, J=13.9 Hz), 3.45 (2H, ABq, J=9.4, 11.5 Hz), 3.69 (2H, q, J=8.7 Hz), 4.79 (2H, s), 7.28 (1H, d, J=7.6 Hz), 7.64 (2H, m), 9.96 (1H, s).

Step 4: [6S/R,9R/S,11R/S] 2',3',4',5,5',6,7,8,9,10-Decahydro-2-carboxaldehydemethylhydrazone-5'-(2,2,2-trifluoroethyl)-spiro[6,9-methanobenzocyclooctene-11,3'-[1,2,5]thiadiazole] 1',1'-dioxide

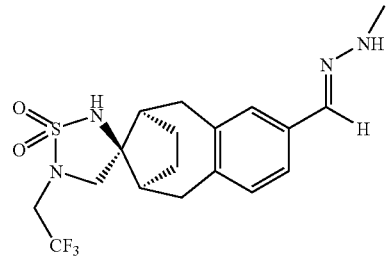

To a suspension of the aldehyde from Step 3 (106 mg, 0.27 mmol) in diethyl ether (4 mL) was added methylhydrazine (15 μL, 0.27 mmol). Tetrahydrofuran (1 mL) was added to aid dissolution. The reaction was stirred at room temperature for 1.5 hours, then the solvent was removed in vacuo to give the title compound as a white foam (112 mg, quant.). δ (¹H, 500 MHz, CDCl₃) 1.29-1.37 (2H, m), 1.68-1.71 (2H, m), 2.43 (2H, br s), 2.66-2.2.74 (2H, m), 2.97 (3H, s), 3.19 (2H, d, J=16 Hz), 3.42 (2H, s), 3.68 (2H, q, J=8.7 Hz), 4.78 (1H, br s), 7.06 (1H, d, J=7.7 Hz), 7.27 (1H, d, J=7.7 Hz), 7.33 (1H, s), 7.49 (1H, s). MS (ES+) 417 ([MH]⁺).

Step 5: [6S/R,9R/S,11R/S] 2',3',4',5,5',6,7,8,9,10-Decahydro-2-(5-(4-fluorophenyl)-1-methyl-1,2,4-triazol-3-yl)-5'-(2,2,2-trifluoroethyl)-spiro[6,9-methanobenzocyclooctene-11,3'-[1,2,5]thiadiazole]1',1'-dioxide

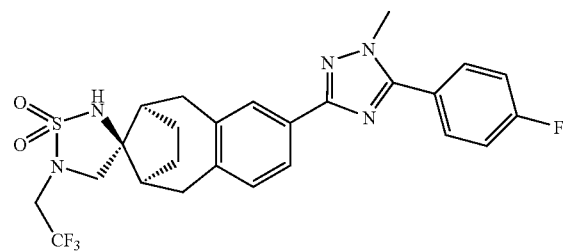

A solution of 4-fluorobenzohydroximinoyl chloride (69 mg, 0.4 mmol) (prepared from syn-4-fluorobenzaldoxime using the general procedure for the synthesis of benzohydroximinoyl chlorides described in *J. Org. Chem.* 1980, 45, 3916) in tetrahydrofuran (2 mL) was added dropwise to a stirred solution of the methylhydrazone from Step 4 (110 mg, 0.26 mmol) and triethylamine (74 μL, 0.53 mmol) in tetrahydrofuran (4 mL) at −10° C. The mixture was stirred at between −10 and 0° C. for 1.5 hours then at ambient temperature for 1 hour. A further 2 equivalents of triethylamine (74 μL) were added, the mixture was cooled to −10° C. and a further 1.5 equivalents of the chloro-oxime (69 mg) added as a solution in tetrahydrofuran (1 mL). The mixture was stirred at between −10 and 0° C. for 0.5 hours then at ambient temperature for 1 hour. The mixture was cooled to −110° C. and a further 4 equivalents of triethylamine (147 μL) and 3 equivalents of chloro-oxime (138 mg) in tetrahydrofuran (1 mL) were added. The mixture was stirred at between −10 and −5° C. for 0.5 hours then at ambient temperature for 18 hours. The reaction was partitioned between ethyl acetate and water. The organic layer was dried (MgSO$_4$) and concentrated on the rotary evaporator without heating. The yellow residue was partially dissolved in acetic acid (7 mL) and heated at reflux for 1 hour. The cooled solution was partitioned between ethyl acetate and water. The organic layer was washed with saturated aqueous sodium hydrogencarbonate (×3), dried (MgSO$_4$) and concentrated. The residue was purified by flash column chromatography on silica eluting with 40 to 50% ethyl acetate/isohexane to give almost pure product (74 mg). This was further purified by flash column chromatography on silica eluting with 1% methanol/dichloromethane followed by recrystallisation from diethyl ether/isohexane to give the product (33 mg, 24%). δ ($^1$H, 500 MHz, CDCl$_3$) 1.32-1.42 (2H, m), 1.69-1.73 (2H, m), 2.45-2.48 (2H, m), 2.73-2.77 (1H, m), 2.81-2.86 (1H, m), 3.23 (1H, d, J=7 Hz), 3.26 (1H, d, J=7 Hz), 3.44 (2H, s), 3.68 (2H, q, J=8.7 Hz), 4.00 (3H, s), 4.69 (1H, s), 7.18 (1H, d, J=8.4 Hz), 7.23 (1H, t, J=8.4 Hz), 7.71-7.74 (2H, m), 7.88 (2H, d, J=5.5 Hz). MS (ES+) 536 ([MH]$^+$).

Example 76

[6S,9R,11R] 2',3',4',5,5',6,7,8,9,10-Decahydro-2-(1-(4-fluorophenyl)-imidazol-4-yl)-5'-(2,2,2-trifluoroethyl)-spiro[6,9-methanobenzocyclooctene-11,3'-[1,2,5]thiadiazole] 1',1'-dioxide

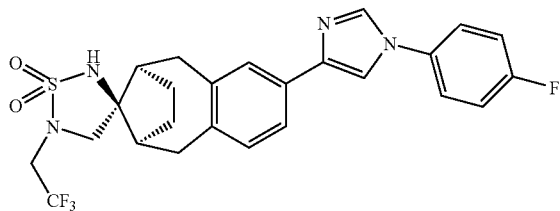

Step 1: 4-Bromo-1-(4-fluorophenyl)imidazole

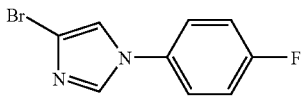

A mixture of 4-bromo-1H-imidazole (223 mg, 1.52 mmol), 4-fluorophenylboronic acid (425 mg, 3.03 mmol), copper(II) acetate (413 mg, 2.28 mmol), pyridine (0.25 mL) and powdered 4 Å molecular sieves (1 g) in 1,2-dichloroethane (7 mL) was stirred at room temperature under a slow stream of air for 44 hours. The reaction mixture was filtered through Celite®, washing with ethyl acetate. The filtrate was concentrated and the residue purified by flash column chromatography on silica eluting with 10 to 20% ethyl acetate/isohexane to give the product as a white solid (135 mg, 37%). δ ($^1$H, 400 MHz, CDCl$_3$) 7.16-7.22 (3H, m), 7.32-7.37 (2H, m), 7.65 (1H, d, J=1.5 Hz). MS (ES+) 241, 243 ([MH]$^+$).

Step 2: [6S,9R,11R] 2',3',4',5,5',6,7,8,9,10-Decahydro-2-(1-(4-fluorophenyl)-imidazol-4-yl)-5'-(2,2,2-trifluoroethyl)-spiro[6,9-methanobenzocyclooctene-11,3'-[1,2,5]thiadiazole] 1',1'-dioxide

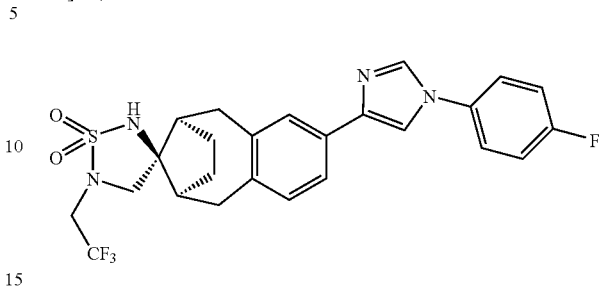

To a degassed solution of 4-bromo-1-(4-fluorophenyl)imidazole from Step 1 (50 mg, 0.21 mmol) and the homochiral boronate from Example 24 Step 1 (100 mg. 0.21 mmol) in N,N-dimethylformamide (3 mL) and water (1 mL) was added cesium carbonate (67 mg, 0.21 mmol) followed by tetrakis(triphenylphosphine) palladium (0) (24 mg, 0.02 mmol). The reaction was heated at 100° C. for 19 hours. The cooled reaction mixture was diluted with ethyl acetate. The organic layer was washed with water (×3) and brine, dried (MgSO$_4$) and concentrated. The residue was purified by flash chromatography on silica eluting with ethyl acetate/isohexane (gradient 20 to 30 to 50% to neat ethyl acetate) followed by recrystallisation from dichloromethane/diethyl ether to give the product (13 mg, 12%). δ ($^1$H, 500 MHz, CDCl$_3$) 1.34-1.42 (2H, m), 1.70-1.72 (2H, m), 2.43-2.48 (2H, m), 2.68-2.82 (2H, m), 3.21-3.25 (2H, m), 3.43 (2H, s), 3.68 (2H, q, J=8.7 Hz), 4.82 (1H, s), 7.12 (1H, d, J=7.8 Hz), 7.19-7.22 (2H, m), 7.40-7.43 (2H, m), 7.48 (1H, d, J=1.1 Hz), 7.54 (1H, d, J=7.8 Hz), 7.61 (1H, s), 7.82 (1H, d, J=1.1 Hz). MS (ES+) 521 ([MH]$^+$).

Example 77

[6S,9R,11R] 2',3',4',5,5',6,7,8,9,10-Decahydro-2-(1-(4-chlorophenyl)-imidazol-4-yl)-5'-(2,2,2-trifluoroethyl)-spiro[6,9-methanobenzocyclooctene-11,3'-[1,2,5]thiadiazole] 1',1'-dioxide

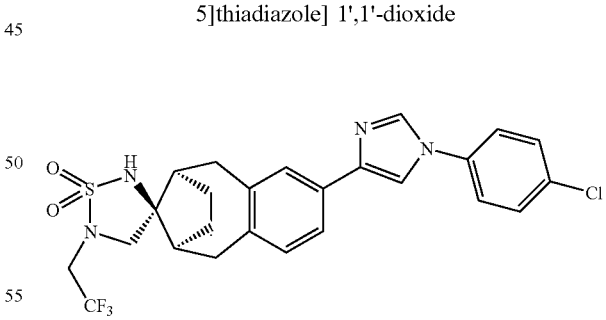

Prepared from 4-bromo-1H-imidazole, 4-chlorophenylboronic acid and homochiral boronate from Example 24 Step 1 following the procedures in Example 76 Steps 1 and 2. δ ($^1$H, 500 MHz, CDCl$_3$) 1.34-1.42 (2H, m), 1.68-1.75 (2H, m), 2.42-2.50 (2H, m), 2.70-2.82 (2H, m), 3.20-3.28 (2H, m), 3.44 (2H, s), 3.68 (2H, q, J=8.7 Hz), 4.68 (1H, s), 7.12 (1H, d, J=7.8 Hz), 7.38 (2H, d, J=8.7 Hz), 7.47-7.51 (3H, m), 7.56 (1H, d, J=7.8 Hz), 7.62 (1H, s), 7.86 (1H, s). MS (ES+) 537, 539 ([MH]$^+$).

Example 78

[6S,9R,11R] 2',3',4',5,5',6,7,8,9,10-Decahydro-2-(1-(3,4-difluorophenyl)-imidazol-4-yl)-5'-(2,2,2-trifluoroethyl)-spiro[6,9-methanobenzocyclooctene-11,3'-[1,2,5]thiadiazole] 1',1'-dioxide

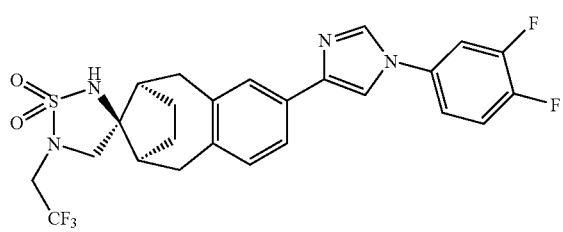

Prepared from 4-bromo-1H-imidazole, 3,4-difluorophenyl-boronic acid and homochiral boronate from Example 24 Step 1 following the procedures in Example 76 Steps 1 and 2. □ (1H, 400 MHz, CDCl$_3$) 1.18-1.24 (2H, m), 1.70-1.73 (2H, m), 2.43-2.49 (2H, m), 2.69-2.81 (2H, m), 3.20-3.26 (2H, m), 3.44 (2H, s), 3.68 (2H, q, J=8.7 Hz), 4.72 (1H, s), 7.13 (1H, d, J=7.8 Hz), 7.19-7.22 (1H, m) 7.28-7.35 (2H, m), 7.48 (1H, d, J=1 Hz), 7.54 (1H, dd, J=7.7, 2 Hz), 7.61 (1H, s), 7.83 (1H, d, J=1 Hz). MS (ES+) 539 ([MH]$^+$).

Example 79

[6S,9R,11R] 2',3',4',5,5',6,7,8,9,10-Decahydro-2-(1-(3,4-dichlorophenyl)-imidazol-4-yl)-5'-(2,2,2-trifluoroethyl)-spiro[6,9-methanobenzocyclooctene-11,3'-[1,2,5]thiadiazole] 1',1'-dioxide

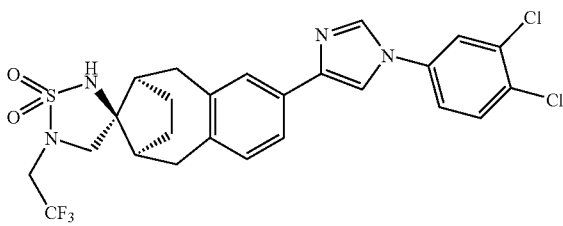

Prepared from 4-bromo-1H-imidazole, 3,4-dichlorophenyl-boronic acid and homochiral boronate from Example 24 Step 1 following the procedures in Example 76 Steps 1 and 2. δ ($^1$H, 400 MHz, CDCl$_3$) 1.24-1.28 (2H, m), 1.70-1.74 (2H, m), 2.42-2.49 (2H, m), 2.69-2.81 (2H, m), 3.20-3.26 (2H, m), 3.44 (2H, s), 3.68 (2H, q, J=8.7 Hz), 4.73 (1H, s), 7.13 (1H, d, J=7.8 Hz), 7.31 (1H, dd, J=8.6, 2.6 Hz), 7.50-7.61 (5H, m), 7.87 (1H, d, J=1 Hz). MS (ES+) 571, 573, 575 ([MH]$^+$).

Example 80

[6S,9R,11R] 2',3',4',5,5',6,7,8,9,10-Decahydro-2-(1-(2,4-difluorophenyl)-imidazol-4-yl)-5'-(2,2,2-trifluoroethyl)-spiro[6,9-methanobenzocyclooctene-11,3'-[1,2,5]thiadiazole] 1',1'-dioxide

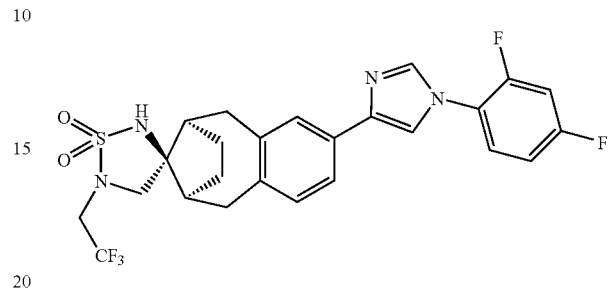

Prepared from 4-bromo-1H-imidazole, 2,4-difluorophenyl-boronic acid and homochiral boronate from Example 24 Step 1 following the procedures in Example 76 Steps 1 and 2. δ ($^1$H, 360 MHz, CDCl$_3$) 1.20-1.27 (2H, m), 1.69-1.73 (2H, m), 2.45-2.47 (2H, m), 2.68-2.82 (2H, m), 3.20-3.26 (2H, m), 3.43 (2H, s), 3.68 (2H, q, J=8.7 Hz), 4.71 (1H, s), 7.00-7.13 (3H, m), 7.40-7.45 (2H, m), 7.54 (1H, d, J=7.9 Hz), 7.61 (1H, s), 7.78 (1H, s). MS (ES+) 539 ([MH]$^+$).

Example 81

[6S,9R,11R] 2',3',4',5,5',6,7,8,9,10-Decahydro-2-(1-(3-fluorophenyl)-imidazol-4-yl)-5'-(2,2,2-trifluoroethyl)-spiro[6,9-methanobenzocyclooctene-11,3'-[1,2,5]thiadiazole] 1',1'-dioxide

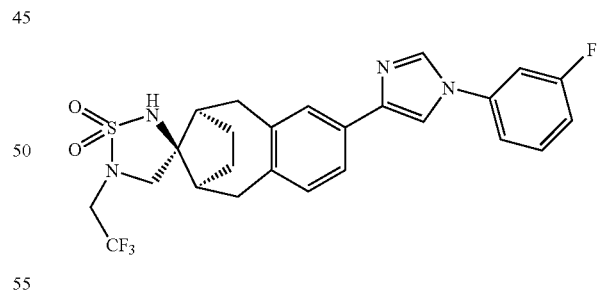

Prepared from 4-bromo-1H-imidazole, 3-fluorophenylboronic acid and homochiral boronate from Example 24 Step 1 following the procedures in Example 76 Steps 1 and 2. δ ($^1$H, 360 MHz, CDCl$_3$) 1.33-1.43 (2H, m), 1.69-1.73 (2H, m), 2.45-2.48 (2H, m), 2.68-2.82 (2H, m), 3.20-3.26 (2H, m), 3.44 (2H, s), 3.68 (2H, q, J=8.7 Hz), 4.75 (1H, s), 7.07-7.20 (3H, m), 7.24 (1H, s), 7.45-7.56 (3H, m), 7.61 (1H, s), 7.89 (1H, s). MS (ES+) 521 ([MH]$^+$).

Example 82

[6S,9R,11R] 2',3',4',5,5',6,7,8,9,10-Decahydro-2-(1-(2-fluorophenyl)-imidazol-4-yl)-5'-(2,2,2-trifluoroethyl)-spiro[6,9-methanobenzocyclooctene-11,3'-[1,2,5]thiadiazole] 1',1'-dioxide

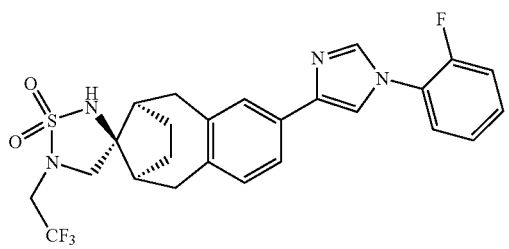

Prepared from 4-bromo-1H-imidazole, 2-fluorophenylboronic acid and homochiral boronate from Example 24 Step 1 following the procedures in Example 76 Steps 1 and 2. δ (¹H, 360 MHz, CDCl₃) 1.92-1.97 (2H, m), 2.26-2.29 (2H, m), 3.01-3.03 (2H, m), 3.29-3.36 (2H, m), 3.76-3.82 (2H, m), 4.00 (2H, s), 4.24 (2H, q, J=8.8 Hz), 5.28 (1H, s), 7.69 (1H, d, J=7.8 Hz), 7.84-7.88 (2H, m), 7.90-7.98 (1H, m), 7.99-8.05 (1H, m), 8.08-8.13 (2H, m), 8.19 (1H, s), 8.42 (1H, s). MS (ES+) 521 ([MH]⁺).

Example 83

[6S,9R,11R] 2',3',4',5,5',6,7,8,9,10-Decahydro-2-(1-(4-(trifluoromethyl)phenyl)-imidazol-4-yl)-5'-(2,2,2-trifluoroethyl)-spiro[6,9-methanobenzocyclooctene-11,3'-[1,2,5]thiadiazole] 1',1'-dioxide

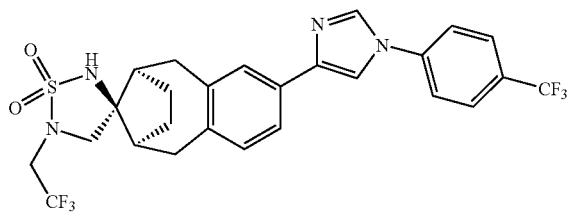

Prepared from 4-bromo-1H-imidazole, 4-(trifluoromethyl)phenylboronic acid and homochiral boronate from Example 24 Step 1 following the procedures in Example 76 Steps 1 and 2. δ (¹H, 360 MHz, DMSO) 1.08-1.11 (2H, m), 1.67-1.75 (2H, m), 2.35-2.38 (2H, m), 2.56-2.70 (2H, m), 3.15-3.20 (2H, m), 3.46 (2H, s), 4.00-4.05 (2H, m), 7.15 (1H, d, J=7.2 Hz), 7.56-7.62 (2H, m), 7.90-8.05 (4H, m), 8.36 (1H, s), 8.49 (1H, s). MS (ES+) 571 ([MH]⁺).

Example 84

[6S,9R,11R] 2',3',4',5,5',6,7,8,9,10-Decahydro-2-(1-isopropylimidazol-4-yl)-5'-(2,2,2-trifluoroethyl)-spiro[6,9-methanobenzocyclooctene-11,3'-[1,2,5] thiadiazole] 1',1'-dioxide

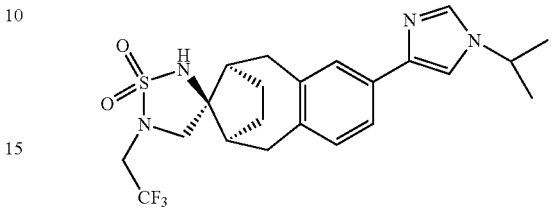

Step 1: 4-Bromo-1-isopropyl-1H-imidazole

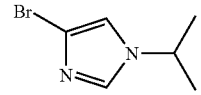

A mixture of 4-bromo-1H-imidazole (1.0 g, 6.80 mmol) in dimethylformamide (5 mL) was stirred at 0° C., to which was added sodium hydride, 60% suspension in oil, (326 mg, 8.20 mmol). The reaction mixture was warmed to room temperature and stirred for 30 minutes, followed by dropwise addition of 2-bromopropane (0.70 mL, 7.48 mmol). The reaction mixture was stirred at room temperature for 15 hours under nitrogen, then quenched with water (10 mL) and extracted with ethyl acetate (3×15 mL). The combined organic extracts were washed with water (20 mL) and extracted with 1M hydrochloric acid (3×20 mL). The combined acidic extracts were washed with ethyl acetate (20 mL), then basified with ammonium hydroxide (pH 12), and extracted with ethyl acetate (3×20 mL). The combined organic extracts were dried (Na₂SO₄), filtered and concentrated. Preparative HPLC, eluting with an ethyl acetate—isohexane gradient, gave the product as a pale brown oil (380 mg, 30%) δ (¹H, 400 MHz, CDCl₃) 1.47 (6H, d, J=6.8 Hz), 4.28-4.32 (1H, m), 6.92 1H, d, J=1.5 Hz), 7.40 (1H, d, J=1.5 Hz). MS (ES+) 189, 191 ([MH]⁺).

Step 2: [6S,9R,11R] 2',3',4',5,5',6,7,8,9,10-Decahydro-2-(1-isopropylimidazol-4-yl)-5'-(2,2,2-trifluoroethyl)-spiro[6,9-methanobenzocyclooctene-11,3'-[1,2,5]thiadiazole] 1',1'-dioxide

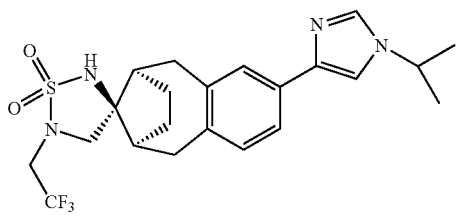

Prepared from 4-bromo-1-isopropyl-1H-imidazole (Step 1) and homochiral boronate from Example 24 Step 1 by the procedure described for Example 76 Step 2. δ (¹H, 400

MHz, CDCl$_3$) 1.30-1.40 (2H, m), 1.53 (6H, d, J=6.8 Hz), 1.67-1.75 (2H, m), 2.40-2.50 (2H, m), 2.66-2.80 (2H, m), 3.18-3.24 (2H, m), 3.42 (2H, s), 3.67 (2H, q, J=8.7 Hz), 4.32-4.42 (1H, m), 4.65 (1H, s), 7.10 (1H, d, J=8 Hz), 7.23 (1H, d, J=1.4 Hz), 7.45 (1H, d, J=8 Hz), 7.55-7.58 (2H, m). MS (ES+) 469 ([MH]$^+$).

Example 85

[6S,9R,11R] 2',3',4',5,5',6,7,8,9,10-Decahydro-2-(1-(4-fluorophenyl)-1,2,3-triazol-4-yl)-5'-(2,2,2-trifluoroethyl)-spiro[6,9-methanobenzocyclooctene-11,3'-[1,2,5]thiadiazole] 1',1'-dioxide

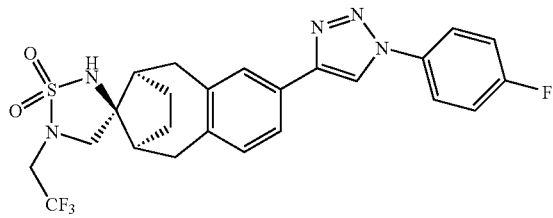

Step 1: [6S,9R,11R] 2',3',4',5,5',6,7,8,9,10-Decahydro-2-(1-trimethylsilylethyn-2-6,9-methanobenzocyclooctene-11,3'-[1,2,5]thiadiazole] 1',1'-dioxide

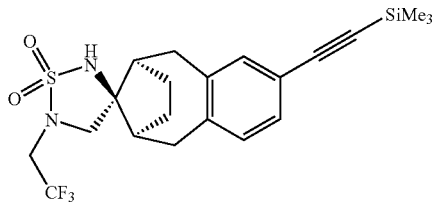

A solution of the homochiral triflate Intermediate E (0.25 g, 0.49 mmol), trimethylsilylacetylene (0.20 mL, 1.4 mmol), copper (I) iodide (0.01 g, 10 mol %), triphenylphosphine (0.025 g, 20 mol %) and tetrakis(triphenylphosphine) palladium (0) (0.03 g, 5 mol %) in piperidine (2 mL) and 1,4-dioxane (1 mL) was heated to 150° C. for 10 min in a microwave heater. The black solution was diluted with 1M hydrochloric acid (20 mL) and extracted with ethyl acetate (20 mL). The extract was dried (Na$_2$SO$_4$), and concentrated. Flash column chromatography on silica gel, eluting with 20% ethyl acetate—isohexane gave the trimethylsilylalkyne as a yellow glass (0.185 g, 83%). δ ($^1$H, 500 MHz, CDCl$_3$) 0.24 (9H, s), 1.24-1.34 (2H, m), 1.68-1.74 (2H, m), 2.42-2.46 (2H, m), 2.62-2.72 (2H, m), 3.15-3.21 (2H, m), 3.42 (2H, s), 3.67 (2H, q, J=8.7 Hz), 4.62 (1Hs s), 7.02 (1H, d, J=8 Hz), 7.20-7.26 (2H, m).

Step 2: [6S,9R,11R] 2',3',4',5,5',6,7,8,9,10-Decahydro-2-ethynyl-5'-(2,2,2-trifluoroethyl)-spiro[6,9-methanobenzocyclooctene-11,3'-[1,2,5]thiadiazole] 1',1'-dioxide

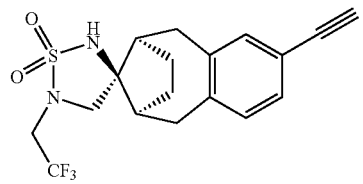

A mixture of the trimethylsilylalkyne from Step 1 (0.27 g, 0.592 mmol) and potassium carbonate (0.1 g, 0.72 mmol) in methanol (2 mL) and tetrahydrofuran (1 mL) was stirred at room temperature for 23 hr. The mixture was diluted with 1M hydrochloric acid (50 mL) and extracted with ethyl acetate (50 mL). The extract was dried (Na$_2$SO$_4$) and concentrated. Preparative HPLC on a normal phase column, eluting with an ethyl acetate—isohexane gradient, gave the alkyne as a brown foam (0.114 g, 51%). δ ($^1$H, 400 MHz, CDCl$_3$) 1.27-1.33 (2H, m), 1.68-1.73 (2H, m), 2.41-2.49 (2H, m), 2.62-2.73 (2H, m), 3.04 (1H, s), 3.16-3.23 (2H, m), 3.43 (2H, s), 3.67 (2H, q, J=8.7 Hz), 4.64 (1H, s), 7.05 (1H, d, J=8 Hz), 7.25-7.27 (2H, m).

Step 3: [6S,9R,11R] 2',3',4',5,5',6,7,8,9,10-Decahydro-2-(1-(4-fluorophenyl)-1,2,3-triazol-4-yl)-5'-(2,2,2-trifluoroethyl)-spiro[6,9-methanobenzocyclooctene-11,3'-[1,2,5]thiadiazole] 1',1'-dioxide

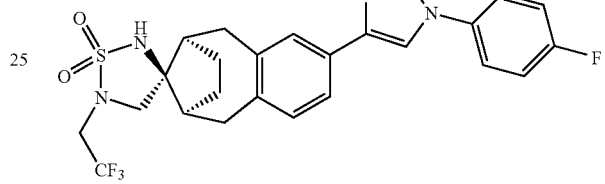

A solution of the alkyne from Step 2 (0.075 g, 0.195 mmol) and 4-fluorophenylazide (0.035 g, 0.25 mmol) in p-xylene (5 mL) was refluxed under nitrogen for 21 hr. The solution was evaporated to dryness. Preparative HPLC on a normal phase column, eluting with an ethyl acetate—isohexane gradient gave the major cycloadduct (0.022 g). Further purification by reverse phase HPLC, eluting with an acetonitrile—pH3 buffer gradient, gave the triazole as yellow solid, which was rinsed with diethyl ether and dried to give a pale yellow powder (0.010 g, 10%). δ ($^1$H, 400 MHz, CDCl$_3$) 1.35-1.42 (2H, m), 1.61-1.68 (2H, m), 2.45-2.52 (2H, m), 2.72-2.86 (2H, m), 3.22-3.30 (2H, m), 3.45 (2H, s), 3.69 (2H, q, J=8.7 Hz), 4.66 (1H, s), 7.21-7.27 (3H, m), 7.62 (1H, d, J=8 Hz), 7.70 (1H, s), 7.75-7.79 (2H, m), 8.12 (1H, s). MS (ES+) 522 ([MH]$^+$).

Example 86

[6S,9R,11R] 2',3',4',5,5',6,7,8,9,10-Decahydro-2-(1-(4-fluorophenyl)-1,2,4-triazol-3-yl)-5'-(2,2,2-trifluoroethyl)-spiro[6,9-methanobenzocyclooctene-11,3'-[1,2,5]thiadiazole] 1',1'-dioxide

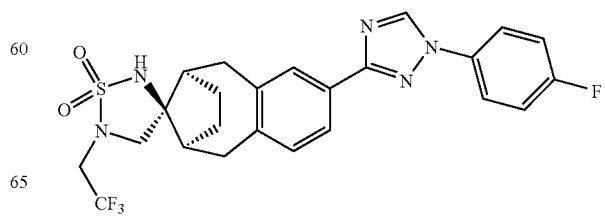

Step 1: 1-(4-Fluorophenyl)-3-bromo-1,2,4-1H-triazole

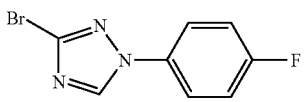

A mixture of 3-bromo-1,2,4-1H-triazole (prepared as described in Chemische Berichte 1967, 100, 2250) (1.0 g, 6.76 mmol), tri(4-fluorophenyl)bismuth diacetate (prepared by the method described in Synthetic Communications 1996, 4569) (4.53 g, 7.4 mmol), copper (II) acetate (0.25 g, 20 mol %) and N,N,N',N'-tetramethylguanidine (1.7 mL, 13.5 mmol) in dry tetrahydrofuran (30 mL) was stirred at 50° C. under a balloon of air for 16 hr. The suspension was poured into water (100 mL) and 1M citric acid (30 mL) to give a suspension of pH 3-4. Ethyl acetate (100 mL) was added and the mixture was filtered through Celite®, washing the filter cake with ethyl acetate (100 mL). The two phases of the filtrate were separated and the organic layer was dried (Na$_2$SO$_4$) and concentrated. Flash column chromatography on silica gel, eluting with 25% then 40% ethyl acetate—isohexane, gave 1-(4-fluorophenyl)-3-bromo-1,2,4-1H-triazole as an off-white solid (0.74 g, 45%). δ ($^1$H, 400 MHz, CDCl$_3$) 7.18-7.24 (2H, m), 7.60-7.65 (2H, m), 8.37 (1H, s). MS (ES+) 242, 244 ([MH]+).

Step 2: [6S,9R,11R] 2',3',4',5,5',6,7,8,9,10-Decahydro-2-(1-(4-fluorophenyl)-1,2,4-triazol-3-yl)-5'-(2,2,2-trifluoroethyl)-spiro[6,9-methanobenzocyclooctene-11,3'-[1,2,5]thiadiazole] 1',1'-dioxide

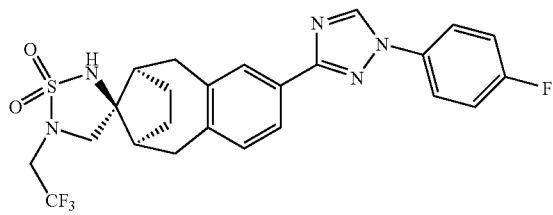

A solution of the bromotriazole from Step 1 (0.10 g, 0.41 mmol), homochiral boronate from Example 24 Step 1 (0.15 g, 0.32 mmol), cesium carbonate (0.25 g, 0.7 mmol) and tetrakis(triphenylphosphine) palladium (0) (0.045 g, 10 mol %) in 1,2-dimethoxyethane (2 mL) and water (1 mL) was refluxed under nitrogen for 15 hr. The mixture was diluted with 1M citric acid (10 mL) and extracted with ethyl acetate (20 mL). The extract was filtered through a plug of silica gel and concentrated. Preparative HPLC on a normal phase column, eluting with an ethyl acetate—isohexane gradient, gave the product as an oil. Trituration with diethyl ether gave the triazole as a white solid (0.084 g, 50%). δ ($^1$H, 500 MHz, CDCl$_3$) 1.33-1.43 (2H, m), 1.70-1.75 (2H, m), 2.45-2.51 (2H, m), 2.74-2.88 (2H, m), 3.24-3.28 (2H, m), 3.45 (2H, s), 3.68 (2H, q, J=8.7 Hz), 4.68 (1H, s), 7.20-7.25 (3H, m), 7.70-7.75 (2H, m), 7.93-7.95 (2H, m), 8.51 (1H, s). MS (ES+) 522 ([MH]$^+$).

Example 87

[6S,9R,11R] 2',3',4',5,5',6,7,8,9,10-Decahydro-2-(5-(4-fluorophenyl)-isoxazol-3-yl)-5'-(2,2,2-trifluoroethyl)-spiro[6,9-methanobenzocyclooctene-11,3'-[1,2,5]thiadiazole] 1',1'-dioxide

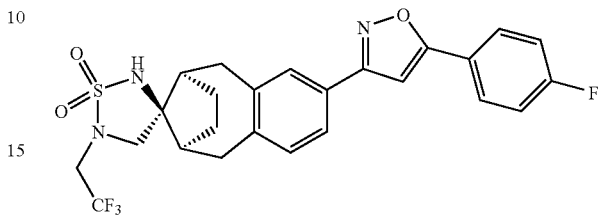

Step 1: [6S,9R,11R] 2',3',4',5,5',6,7,8,9,10-Decahydro-2-(carboxaldehyde oxime)-5'-(2,2,2-trifluoroethyl)-spiro[6,9-methanobenzocyclooctene-11,3'-[1,2,5]thiadiazole] 1',1'-dioxide

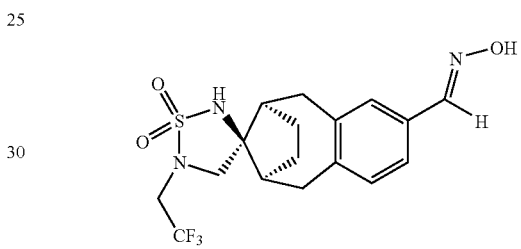

A mixture of the aldehyde Example 75, Step 3 (192 mg, 0.5 mmol), hydroxylamine hydrochloride (104 mg, 1.5 mmol) and sodium acetate (204 mg, 1.5 mmol) in dioxane (4 mL) was stirred at room temperature for 16 hours. The reaction was diluted with sodium hydrogen carbonate (half saturated 30 mL) and extracted with ethyl acetate (2×30 mL). The extracts were washed with brine, dried (MgSO$_4$) and evaporated in vacuo to a clear gum (200 mg, >99%). Λ ($^1$H, 400 MHz, CDCl$_3$) 1.23-1.32 (2H, m), 1.68-1.77 (2H, m), 2.40-2.50 (2H, m), 2.67-2.73 (2H, m), 3.19 (2H, d, J=16.1 Hz), 3.43 (2H, s), 3.67-3.72 (2H, m), 4.89 (1H, br s), 7.09 (1H, d, J=7.6 Hz); 7.29-7.31 (2H, m), 7.53 (1H, br s) and 8.09 (1H, s).

Step 2: [6S,9R,11R] 2',3',4',5,5',6,7,8,9,10-Decahydro-2-(5-(4-fluorophenyl)-isoxazol-3-yl)-5'-(2,2,2-trifluoroethyl)-spiro[6,9-methanobenzocyclooctene-11,3'-[1,2,5]thiadiazole] 1',1'-dioxide

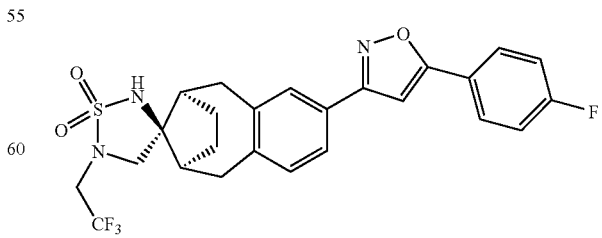

The title compound was prepared following the procedure of Moriya et al. (J C S Perkin 1, 1994, 413). A solution of sodium hypochlorite (13 mg, 0.12 mmol) in dichloromethane (1 mL) was added to a solution of the oxime from step 1 (50 mg, 0.12 mmol), bis(tributyl tin) oxide (31 TL, 0.06 mmol) and 4-fluorophenyl acetylene (55 TL, 0.24 mmol) in dichloromethane (1 mL), under a nitrogen atmosphere, at <−20° C. The reaction was allowed to warm to room temperature and was stirred for 16 hours. The reaction was treated with potassium fluoride in methanol (sat. 0.5 mL), diluted with water (20 mL) and extracted with ethyl acetate (2×15 mL). The extracts were washed with brine, dried (MgSO$_4$) and evaporated in vacuo to a clear gum which was purified by column chromatography on silica eluting with ethyl acetate:iso hexane (1:3) to give a white solid. The solid was dissolved in acetonitrile and washed with iso hexane (×3). The solvent was evaporated in vacuo to provide the title compound as a white solid 25 mg, 40%). Λ ($^1$H, 400 MHz CDCl$_3$) 1.33-1.40 (2H, m), 1.70-1.79 (2H, m), 2.46-2.54 (2H, m), 2.73-2.85 (2H, m), 3.27 (2H, d, J=16.1 Hz), 3.45 (2H, s), 3.69 (2H, q, J=8.7 Hz), 4.69 (1H, br s), 6.76 (1H, s), 7.19 (3H, q, J=8.6 Hz), 7.58-7.63 (2H, m) and 7.81-7.85 (2H, m). M/Z (ES+) 522 ([MH]$^+$).

Example 88

[6S,9R,11R] 2',3',4',5,5',6,7,8,9,10-Decahydro-2-5-(2-pyridyl)-isoxazol-3-yl)-5'-(2,2,2-trifluoroethyl)-spiro[6,9-methanobenzocyclooctene-11,3'-[1,2,5]thiadiazole] 1',1'-dioxide

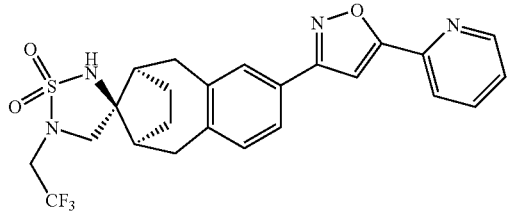

The title compound was prepared in a manner analogous to example 87. The crude product was purified by column chromatography on silica eluting with ethyl acetate:isohexane (1:2) to give a white solid 13 mg, 22%). M/Z (ES+) 505 ([MH]$^+$).

What is claimed is:

1. A compound of formula X(a):

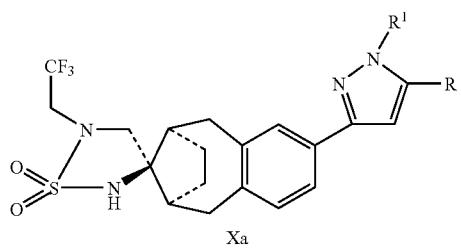

wherein R$^1$ is H or a hydrocarbon group of up to 5 carbon atoms optionally substituted with up to 3 halogen atoms; and R is selected from:

(i) CF$_3$ or a non-aromatic hydrocarbon group of up to 10 carbon atoms, optionally substituted with halogen, CF$_3$, CHF$_2$, CN, OH, CO$_2$H, C$_{2-6}$acyl, C$_{1-4}$alkoxy or C$_{1-4}$alkoxycarbonyl;

(ii) a non-aromatic heterocyclic group consisting of up to 7 ring atoms of which up to 3 are chosen from N, O and S and the remainder are carbon, bearing 0-3 substituents independently selected from oxo, halogen, CN, C$_{1-6}$alkyl, OH, CF$_3$, CHF$_2$, CH$_2$F, C$_{2-6}$acyl, CO$_2$H, C$_{1-4}$alkoxy and C$_{1-4}$alkoxycarbonyl;

(iii) phenyl or 6-membered heteroaryl, either of which bears 0-3 substituents independently selected from halogen, CF$_3$, CHF$_2$, CH$_2$F, NO$_2$, CN, OCF$_3$, C$_{1-6}$alkyl and C$_{1-6}$alkoxy; and (iv) N(R$^a$)$_2$ where each R$^a$ independently represents H or C$_{1-6}$alkyl which is optionally substituted with halogen, CF$_3$, CHF$_2$, CN, OH, CO$_2$H, C$_{2-6}$acyl, C$_{1-4}$alkoxy or C$_{1-4}$alkoxycarbonyl; or a pharmaceutically acceptable salt thereof.

2. A compound of claim 1 wherein R is phenyl or 6-membered heteroaryl, either of which bears 0-3 substituents independently selected from halogen, CF$_3$, CHF$_2$, CH$_2$F, NO$_2$, CN, OCF$_3$, C$_{1-6}$alkyl and C$_{1-6}$alkoxy.

3. A compound of claim 2 wherein R is monohalophenyl or dihalophenyl.

4. A compound of claim 1 wherein R$^1$ is methyl.

5. A compound of claim 1 selected from the group consisting of [6S,9R,11R] 2',3',4',5,5',6,7,8,9,10-Decahydro-2-(5-(4-fluorophenyl)-1-methyl-pyrazol-3-yl)-5'-(2,2,2-trifluoroethyl)-spiro[6,9-methanobenzocyclooctene-11,3'-[1,2,5]thiadiazole] 1',1'-dioxide; [6S,9R,11R] 2',3',4',5,5',6,7,8,9,10-Decahydro-2-(5-(3,4-difluorophenyl)-1-methyl-pyrazol-3-yl)-5'-(2,2,2-trifluoroethyl)-spiro[6,9-methanobenzocyclooctene-11,3'-[1,2,5]thiadiazole] 1',1'-dioxide; [6S,9R,11R] 2',3',4',5,5',6,7,8,9,10-Decahydro-2-(5-(4-chlorophenyl)-1-methyl-pyrazol-3-yl)-5'-(2,2,2-trifluoroethyl)-spiro[6,9-methanobenzocyclooctene-11,3'-[1,2,5]thiadiazole] 1',1'-dioxide; [6S,9R,11R] 2',3',4',5,5',6,7,8,9,10-Decahydro-2-(5-(2,4-difluorophenyl)-1-methyl-pyrazol-3-yl)-5'-(2,2,2-trifluoroethyl)-spiro[6,9-methanobenzocyclooctene-11,3'-[1,2,5]thiadiazole] 1',1'-dioxide; [6S,9R,11R] 2',3',4',5,5',6,7,8,9,10-Decahydro-2-(5-(3-chloro-4-fluorophenyl)-1-methyl-pyrazol-3-yl)-5'-(2,2,2-trifluoroethyl)-spiro[6,9-methanobenzocyclooctene-11,3'-[1,2,5]thiadiazole] 1',1'-dioxide; and [6S,9R,11R] 2',3',4',5,5',6,7,8,9,10-Decahydro-2-(5-(3,4-dichlorophenyl)-1-methyl-pyrazol-3-yl)-5'-(2,2,2-trifluoroethyl)-spiro[6,9-methanobenzocyclooctene-11,3'-[1,2,5]thiadiazole] 1',1'-dioxide; or a pharmaceutically salt thereof.

6. A pharmaceutical composition comprising a compound of claim 1 and a pharmaceutically acceptable carrier.

7. A method of treatment of a subject suffering from Alzheimer's disease which comprises administering to that subject an effective amount of a compound of claim 1.

8. The compound [6S,9R,11R] 2',3',4',5,5',6,7,8,9,10-Decahydro-2-(5-(4-fluorophenyl)-1-methyl-pyrazol-3-yl)-5'-(2,2,2-trifluoroethyl)-spiro[6,9-methanobenzocyclooctene-11,3'-[1,2,5]thiadiazole] 1',1'-dioxide; or a pharmaceutically acceptable salt thereof.

9. A pharmaceutical composition comprising a compound of claim 8 and a pharmaceutically acceptable carrier.

10. A method of treatment of a subject suffering from Alzheimer's disease which comprises administering to that subject an effective amount of a compound of claim 8.

* * * * *